US008369936B2

(12) United States Patent
Farringdon et al.

(10) Patent No.: US 8,369,936 B2
(45) Date of Patent: Feb. 5, 2013

(54) WEARABLE APPARATUS FOR MEASURING HEART-RELATED PARAMETERS AND DERIVING HUMAN STATUS PARAMETERS FROM SENSED PHYSIOLOGICAL AND CONTEXTUAL PARAMETERS

(75) Inventors: Jonathan Farringdon, Pittsburgh, PA (US); John M. Stivoric, Pittsburgh, PA (US); Eric Teller, San Francisco, CA (US); David Andre, San Francisco, CA (US); Scott Boehmke, Wexford, PA (US); James Gasbarro, Pittsburgh, PA (US); Gregory Kovacs, Palo Alto, CA (US); Raymond Pelletier, Pittsburgh, PA (US); Christopher Kasabach, Pittsburgh, PA (US)

(73) Assignee: BodyMedia, Inc., Pittsburgh, PA (US)

( * ) Notice: Subject to any disclaimer, the term of this patent is extended or adjusted under 35 U.S.C. 154(b) by 0 days.

(21) Appl. No.: 12/840,109

(22) Filed: Jul. 20, 2010

(65) Prior Publication Data

US 2010/0286532 A1 Nov. 11, 2010

Related U.S. Application Data

(63) Continuation of application No. 11/928,302, filed on Oct. 30, 2007, now abandoned, which is a continuation of application No. 10/940,889, filed on Sep. 13, 2004, now Pat. No. 7,502,643.

(60) Provisional application No. 60/502,764, filed on Sep. 12, 2003, provisional application No. 60/510,013, (Continued)

(51) Int. Cl.
*A61B 5/04* (2006.01)

(52) U.S. Cl. ......... 600/509; 600/508; 600/513; 600/519

(58) Field of Classification Search .................. 600/508, 600/509, 513, 519
See application file for complete search history.

(56) References Cited

U.S. PATENT DOCUMENTS

| 4,031,365 A | 6/1977 | Raggiotti et al. |
| 4,052,979 A | 10/1977 | Scherr et al. |
| 4,129,125 A | 12/1978 | Lester et al. |
| 4,148,304 A | 4/1979 | Mull |

(Continued)

FOREIGN PATENT DOCUMENTS

| DE | 19832361 A1 | 2/2000 |
| DE | 19911766 A1 | 9/2000 |

(Continued)

OTHER PUBLICATIONS

Georgia Tech. "Smart T-shirt", Nov. 14, 1997, Georgia Institute of Technology Press Release.

(Continued)

*Primary Examiner* — Carl H Layno
*Assistant Examiner* — Natasha Patel
(74) *Attorney, Agent, or Firm* — GTC Law Group LLP & Affiliates

(57) ABSTRACT

A monitor device and associated methodology are disclosed which provide a self contained, relatively small and continuously wearable package for the monitoring of heart related parameters, including ECG. The detection of heart related parameters is predicated on the location of inequipotential signals located within regions of the human body conventionally defined as equivalent for the purpose of detection of heart related electrical activity, such as on single limbs. Amplification, filtering and processing methods and apparatus are described in conjunction with analytical tools for beat detection and display.

10 Claims, 43 Drawing Sheets

Related U.S. Application Data filed on Oct. 9, 2003, provisional application No. 60/555,280, filed on Mar. 22, 2004.

(56) References Cited

U.S. PATENT DOCUMENTS

| | | | |
|---|---|---|---|
| 4,151,831 A | 5/1979 | Lester |
| 4,192,000 A | 3/1980 | Lipsey |
| 4,364,398 A | 12/1982 | Sassi et al. |
| 4,377,171 A | 3/1983 | Wada |
| 4,387,724 A | 6/1983 | Zartmann |
| 4,407,295 A | 10/1983 | Steuer et al. |
| 4,425,920 A | 1/1984 | Bourland et al. |
| 4,488,558 A | 12/1984 | Simbruner et al. |
| 4,509,531 A | 4/1985 | Ward |
| 4,531,527 A | 7/1985 | Reinhold, Jr. et al. |
| 4,539,994 A | 9/1985 | Baumbach et al. |
| 4,557,273 A | 12/1985 | Stoller et al. |
| 4,576,179 A | 3/1986 | Manus et al. |
| 4,608,987 A | 9/1986 | Mills |
| 4,622,979 A | 11/1986 | Katchis et al. |
| 4,672,977 A | 6/1987 | Kroll |
| 4,676,254 A | 6/1987 | Frohn |
| 4,757,453 A | 7/1988 | Nasiff |
| 4,784,162 A | 11/1988 | Ricks et al. |
| 4,803,625 A | 2/1989 | Fu et al. |
| 4,819,860 A | 4/1989 | Hargrove et al. |
| 4,827,943 A | 5/1989 | Bornn et al. |
| 4,828,257 A | 5/1989 | Dyer et al. |
| 4,883,063 A | 11/1989 | Bernard et al. |
| 4,891,756 A | 1/1990 | Williams et al. |
| 4,917,108 A | 4/1990 | Mault |
| 4,958,645 A | 9/1990 | Cadell et al. |
| 4,966,154 A | 10/1990 | Cooper et al. |
| 4,981,139 A | 1/1991 | Pfohl |
| 5,007,427 A | 4/1991 | Suzuki et al. |
| 5,012,411 A | 4/1991 | Policastro |
| 5,027,824 A | 7/1991 | Dougherty et al. |
| 5,038,792 A | 8/1991 | Mault |
| 5,040,541 A | 8/1991 | Poppendiek |
| 5,050,612 A | 9/1991 | Matsumura |
| 5,072,458 A | 12/1991 | Suzuki |
| 5,111,818 A | 5/1992 | Suzuki et al. |
| 5,135,311 A | 8/1992 | Alpert |
| 5,148,002 A | 9/1992 | Kuo et al. |
| 5,178,155 A | 1/1993 | Mault |
| 5,179,958 A | 1/1993 | Mault |
| 5,216,599 A | 6/1993 | Uebe et al. |
| 5,224,479 A | 7/1993 | Sekine |
| 5,263,491 A | 11/1993 | Thornton |
| 5,285,398 A | 2/1994 | Janik |
| 5,305,244 A | 4/1994 | Newman et al. |
| 5,335,664 A | 8/1994 | Nagashima |
| 5,353,793 A | 10/1994 | Bornn |
| 5,410,471 A | 4/1995 | Alyfuku et al. |
| 5,435,315 A | 7/1995 | McPhee et al. |
| 5,445,149 A | 8/1995 | Rotolo et al. |
| 5,458,123 A | 10/1995 | Unger |
| 5,469,861 A * | 11/1995 | Piscopo et al. ............. 600/594 |
| 5,474,090 A | 12/1995 | Begun et al. |
| 5,476,103 A | 12/1995 | Nashner |
| 5,484,389 A | 1/1996 | Stark et al. |
| 5,491,651 A | 2/1996 | Janik |
| 5,511,553 A | 4/1996 | Segalowitz et al. |
| 5,515,858 A | 5/1996 | Myllymaki |
| 5,515,865 A | 5/1996 | Scanlon |
| 5,524,618 A | 6/1996 | Pottgen et al. |
| 5,555,490 A | 9/1996 | Carroll |
| 5,559,497 A | 9/1996 | Hong |
| 5,566,679 A | 10/1996 | Herriott |
| 5,581,238 A | 12/1996 | Chang et al. |
| 5,581,492 A | 12/1996 | Janik |
| 5,583,758 A | 12/1996 | McIlroy et al. |
| 5,611,085 A | 3/1997 | Rasmussen |
| 5,617,477 A | 4/1997 | Boyden |
| 5,622,180 A | 4/1997 | Tammi et al. |
| 5,645,068 A | 7/1997 | Mezack et al. |
| 5,652,570 A | 7/1997 | Lepkofker et al. |
| 5,663,703 A | 9/1997 | Pearlman et al. |
| 5,666,096 A | 9/1997 | Van Zeeland |
| 5,670,944 A | 9/1997 | Myllymaki |
| 5,673,691 A | 10/1997 | Abrams et al. |
| 5,673,692 A | 10/1997 | Schulze et al. |
| 5,686,516 A | 11/1997 | Tzur |
| 5,687,734 A | 11/1997 | Dempsey et al. |
| 5,697,791 A | 12/1997 | Nashner et al. |
| 5,701,894 A | 12/1997 | Cherry et al. |
| 5,704,350 A | 1/1998 | Williams, III |
| 5,719,743 A | 2/1998 | Jenkins et al. |
| 5,724,025 A | 3/1998 | Tavori |
| 5,726,631 A | 3/1998 | Lin |
| 5,729,203 A | 3/1998 | Oka et al. |
| 5,730,140 A | 3/1998 | Fitch |
| 5,738,104 A | 4/1998 | Lo et al. |
| 5,741,217 A | 4/1998 | Gero |
| 5,752,976 A | 5/1998 | Duffin et al. |
| 5,771,001 A | 6/1998 | Cobb |
| 5,778,345 A | 7/1998 | McCartney et al. |
| 5,778,882 A | 7/1998 | Raymond et al. |
| 5,798,907 A | 8/1998 | Janik |
| 5,803,915 A | 9/1998 | Kremenchugsky et al. |
| 5,813,766 A | 9/1998 | Chen |
| 5,813,994 A | 9/1998 | Pottgen et al. |
| 5,823,975 A | 10/1998 | Stark et al. |
| 5,827,180 A | 10/1998 | Goodman |
| 5,828,943 A | 10/1998 | Brown |
| 5,832,296 A | 11/1998 | Wang et al. |
| 5,832,448 A | 11/1998 | Brown |
| 5,836,300 A | 11/1998 | Mault |
| 5,839,901 A | 11/1998 | Karkanen et al. |
| 5,853,005 A | 12/1998 | Scanlon |
| 5,855,550 A | 1/1999 | Lai et al. |
| 5,857,939 A | 1/1999 | Kaufman |
| 5,857,967 A | 1/1999 | Frid et al. |
| 5,862,803 A | 1/1999 | Besson et al. |
| 5,865,733 A | 2/1999 | Malinouskas et al. |
| 5,868,669 A | 2/1999 | Iliff |
| 5,868,671 A | 2/1999 | Mahoney |
| 5,871,451 A | 2/1999 | Unger et al. |
| 5,876,350 A | 3/1999 | Lo et al. |
| 5,879,163 A | 3/1999 | Brown et al. |
| 5,879,309 A | 3/1999 | Johnson et al. |
| 5,884,198 A | 3/1999 | Kese et al. |
| 5,888,172 A | 3/1999 | Andrus et al. |
| 5,897,493 A | 4/1999 | Brown |
| 5,899,855 A | 5/1999 | Brown |
| 5,902,250 A | 5/1999 | Verrier et al. |
| 5,908,396 A | 6/1999 | Hayakawa et al. |
| 5,912,865 A | 6/1999 | Ortega |
| 5,913,310 A | 6/1999 | Brown |
| 5,919,141 A | 7/1999 | Money et al. |
| 5,929,782 A | 7/1999 | Stark et al. |
| 5,931,791 A | 8/1999 | Saltzstein et al. |
| 5,933,136 A | 8/1999 | Brown |
| 5,941,837 A | 8/1999 | Amano et al. |
| 5,951,300 A | 9/1999 | Brown |
| 5,956,501 A | 9/1999 | Brown |
| 5,959,529 A | 9/1999 | Kail et al. |
| 5,959,611 A | 9/1999 | Smailagic et al. |
| 5,960,403 A | 9/1999 | Brown |
| 5,976,083 A | 11/1999 | Richardson et al. |
| 6,032,119 A | 2/2000 | Brown et al. |
| 6,047,203 A | 4/2000 | Sackner et al. |
| 6,053,872 A | 4/2000 | Mohler |
| 6,059,692 A | 5/2000 | Hickman |
| 6,067,468 A | 5/2000 | Korenman et al. |
| 6,091,973 A | 7/2000 | Colla et al. |
| 6,095,949 A | 8/2000 | Arai et al. |
| 6,101,407 A | 8/2000 | Groezinger |
| 6,101,478 A | 8/2000 | Brown |
| 6,135,107 A | 10/2000 | Mault |
| 6,138,079 A | 10/2000 | Putnam |
| 6,154,668 A | 11/2000 | Pederson et al. |
| 6,168,563 B1 | 1/2001 | Brown |
| 6,184,797 B1 | 2/2001 | Stark et al. |

| | | |
|---|---|---|
| 6,190,314 B1 | 2/2001 | Ark et al. |
| 6,198,394 B1 | 3/2001 | Jacobson et al. |
| 6,208,900 B1 | 3/2001 | Ecker et al. |
| 6,221,011 B1 | 4/2001 | Bardy et al. |
| 6,225,901 B1 | 5/2001 | Kail, IV |
| 6,225,980 B1 | 5/2001 | Weiss et al. |
| 6,240,323 B1 | 5/2001 | Calenzo et al. |
| 6,247,647 B1 | 6/2001 | Courtney et al. |
| 6,248,065 B1 | 6/2001 | Brown |
| 6,251,048 B1 | 6/2001 | Kaufman |
| 6,254,536 B1 | 7/2001 | DeVito |
| 6,265,978 B1 | 7/2001 | Atlas |
| 6,285,897 B1 | 9/2001 | Kilcoyne et al. |
| 6,287,252 B1 | 9/2001 | Lugo |
| 6,290,646 B1 | 9/2001 | Cosentino et al. |
| 6,290,650 B1 | 9/2001 | Butterfield et al. |
| 6,292,698 B1 | 9/2001 | Duffin et al. |
| 6,298,218 B1 | 10/2001 | Lowe et al. |
| 6,302,844 B1 | 10/2001 | Walker et al. |
| 6,306,088 B1 | 10/2001 | Krausman et al. |
| 6,312,363 B1 | 11/2001 | Watterson et al. |
| 6,315,719 B1 | 11/2001 | Rode et al. |
| 6,327,495 B1 | 12/2001 | Iwabuchi |
| 6,336,900 B1 | 1/2002 | Alleckson et al. |
| 6,339,720 B1 | 1/2002 | Anzellini et al. |
| 6,341,229 B1 | 1/2002 | Akiva |
| 6,364,834 B1 | 4/2002 | Reuss et al. |
| 6,366,871 B1 | 4/2002 | Geva |
| 6,368,287 B1 | 4/2002 | Hadas |
| 6,371,123 B1 | 4/2002 | Stark et al. |
| 6,377,162 B1 | 4/2002 | Delestienne et al. |
| 6,385,473 B1 | 5/2002 | Haines et al. |
| 6,416,471 B1 | 7/2002 | Kumar et al. |
| 6,450,922 B1 | 9/2002 | Henderson et al. |
| 6,450,953 B1 | 9/2002 | Place et al. |
| 6,454,708 B1 | 9/2002 | Ferguson et al. |
| 6,466,232 B1 | 10/2002 | Newell et al. |
| 6,468,222 B1 | 10/2002 | Mault et al. |
| 6,478,736 B1 | 11/2002 | Mault |
| 6,494,829 B1 | 12/2002 | New, Jr. et al. |
| 6,513,532 B2 | 2/2003 | Mault et al. |
| 6,514,200 B1 | 2/2003 | Khouri et al. |
| 6,516,289 B2 * | 2/2003 | David ........................ 600/384 |
| 6,527,711 B1 | 3/2003 | Stivoric et al. |
| 6,532,381 B2 | 3/2003 | Bayer et al. |
| 6,533,731 B2 | 3/2003 | Pottgen et al. |
| 6,547,745 B1 | 4/2003 | Rubinstein et al. |
| 6,551,251 B2 | 4/2003 | Zuckerwar et al. |
| 6,553,251 B1 | 4/2003 | Lähdesmäki |
| 6,571,200 B1 | 5/2003 | Mault |
| 6,584,344 B2 | 6/2003 | Hannula |
| 6,595,929 B2 | 7/2003 | Stivoric et al. |
| 6,597,944 B1 | 7/2003 | Hadas |
| 6,605,038 B1 | 8/2003 | Teller et al. |
| 6,610,012 B2 | 8/2003 | Mault |
| 6,611,206 B2 | 8/2003 | Eshelman et al. |
| 6,616,613 B1 | 9/2003 | Goodman et al. |
| 6,656,125 B2 | 12/2003 | Misczynski et al. |
| 6,665,559 B2 | 12/2003 | Rowlandson |
| 6,690,959 B2 | 2/2004 | Thompson |
| 6,712,615 B2 | 3/2004 | Martin |
| 6,734,802 B2 | 5/2004 | Halleck et al. |
| 6,755,795 B2 | 6/2004 | Mammaropoulos et al. |
| 6,790,178 B1 | 9/2004 | Mault et al. |
| 6,808,473 B2 | 10/2004 | Hisano et al. |
| 6,842,877 B2 | 1/2005 | Robarts et al. |
| 6,852,085 B2 | 2/2005 | Rubinstein et al. |
| 6,874,127 B2 | 3/2005 | Newell et al. |
| 6,886,978 B2 | 5/2005 | Tokita et al. |
| 6,920,348 B2 | 7/2005 | Vasin et al. |
| 6,968,375 B1 | 11/2005 | Brown |
| 7,330,818 B1 | 2/2008 | Ladocsi et al. |
| 7,502,643 B2 | 3/2009 | Farringdon et al. |
| 7,676,384 B2 | 3/2010 | Baker et al. |
| 2001/0029340 A1 | 10/2001 | Mault et al. |
| 2001/0032059 A1 | 10/2001 | Kelly, Jr. et al. |
| 2001/0044581 A1 | 11/2001 | Mault |
| 2001/0044588 A1 | 11/2001 | Mault et al. |
| 2001/0049470 A1 | 12/2001 | Mault et al. |
| 2001/0056229 A1 | 12/2001 | Cosentino et al. |
| 2002/0019296 A1 | 2/2002 | Freeman et al. |
| 2002/0019586 A1 | 2/2002 | Teller et al. |
| 2002/0028995 A1 | 3/2002 | Mault |
| 2002/0032386 A1 | 3/2002 | Sackner et al. |
| 2002/0055857 A1 | 5/2002 | Mault et al. |
| 2002/0107450 A1 | 8/2002 | Ogura |
| 2002/0111539 A1 | 8/2002 | Cosentino et al. |
| 2002/0128804 A1 | 9/2002 | Geva |
| 2002/0133378 A1 | 9/2002 | Mault et al. |
| 2002/0183646 A1 * | 12/2002 | Stivoric et al. ............ 600/549 |
| 2003/0040002 A1 | 2/2003 | Ledley et al. |
| 2003/0055460 A1 | 3/2003 | Owen et al. |
| 2003/0069510 A1 | 4/2003 | Semler |
| 2003/0083559 A1 | 5/2003 | Thompson et al. |
| 2003/0092975 A1 | 5/2003 | Casscells et al. |
| 2003/0176797 A1 | 9/2003 | Anzellini |
| 2003/0208113 A1 | 11/2003 | Mault et al. |
| 2004/0102931 A1 | 5/2004 | Ellis et al. |
| 2005/0070778 A1 | 3/2005 | Lackey et al. |
| 2005/0099294 A1 | 5/2005 | Bogner et al. |
| 2005/0226310 A1 | 10/2005 | Nakazawa et al. |
| 2006/0235280 A1 | 10/2006 | Vonk et al. |
| 2006/0293921 A1 | 12/2006 | McCarthy et al. |

FOREIGN PATENT DOCUMENTS

| | | |
|---|---|---|
| EP | 0670064 B1 | 11/1993 |
| EP | 0707825 A2 | 4/1996 |
| EP | 0880936 A3 | 3/1999 |
| GB | 2322952 A | 5/1997 |
| JP | 4341243 | 11/1992 |
| JP | 2002095637 | 4/2002 |
| WO | 9301574 | 1/1993 |
| WO | 9425841 | 10/1994 |
| WO | 9706499 | 2/1997 |
| WO | 9927483 | 6/1999 |
| WO | 0011578 | 3/2000 |
| WO | 0026882 | 5/2000 |
| WO | 0032098 | 6/2000 |
| WO | 0047108 | 8/2000 |
| WO | 0051543 | 9/2000 |
| WO | 0052604 | 9/2000 |
| WO | 0054650 | 9/2000 |
| WO | 0108554 | 2/2001 |
| WO | 0126535 | 4/2001 |
| WO | 0126547 | 4/2001 |
| WO | 0128416 | 4/2001 |
| WO | 0128495 | 4/2001 |
| WO | 0139089 | 5/2001 |
| WO | 0152718 | 7/2001 |
| WO | 0156454 | 8/2001 |
| WO | 0182783 | 11/2001 |
| WO | 0182789 | 11/2001 |
| WO | 0189365 | 11/2001 |
| WO | 0189368 | 11/2001 |
| WO | 0269798 | 11/2002 |
| WO | 2005046433 | 5/2005 |

OTHER PUBLICATIONS

Personal Health Monitor for Homes, Apr. 1997, Timo Tuomisto & Vesa Pentikainen, ERCIM News, No. 29.
CYBeR-CARE Internet Healthcare Technologies, Oct. 7, 1999, BW Health Wire.
Nearer to the Heart, Jan. 7, 1999, Brianna Krebs Washington Post.
Portable Sensor Provides Re-mote Monitor-ing of Heart, Oct. 27, 1998, Nikkei Weekly.
FDA Clears Datex-Ohmeda Pulse Oximeter, Dec. 3, 1998, BW Health Wire.
Estee Soft New Version of LifeConnect, Jan. 20, 1999, Business Wire.
Matsushita Home Health Check System, Dec. 17, 1998, The Nihon Keizai Shimbun.
Thermal Gap Fillers, Feb. 6, 2001, Kent Young, (article downloaded from www.chomerics.com).
THERM-A-GAP, Feb. 6, 2001, Chomerics Technical Bulletin 70.
CoolPoly, the Original Ther-mally Conduc-tive Polymer, Feb. 7, 2001, Article downloaded from www.coolpolymers.com.

Micro-Foil Heat Flux Sensors, Oct. 1995, RdF Corporation Catalog No. HFS-A.

Industrial Micro-Foil Heat Flux Sensor, Oct. 1995, RdF Corporation Catalog No. HFS-B.

Industrial/Commercial Micro-Foil Heat Flux Sensor, Dec. 1999, RdF Corporation Catalog No. HFS-C.

Warfighter Physiological Status Monitoring, 1999, MOMRP Fact Sheet No. 6, USAMRMC—(downloaded from www.momrp.

The H.J. Andrews Climatological Field Measurement Program, Aug. 9, 1997, Henshaw, D. (downloaded from www.fsl.orst.edu).

Weight Watchers TurnAround, 2004, Weight Watchers (downloaded from www.weightwatchers.com).

Jenny Craig Weight Loss Programs, 2004, Jenny Craig (downloaded from www.jennycraig.com).

The Complete Nutrition & Weight Management Solution Based on Your Unique Metabolic Fingerprint & Goals, 2004, BalanceLog (downloaded from www.healthetech.com).

What is FitDay?, 2004, FitDay (downloaded from www.fitday.com).

A combined heart rate and movement sensor: proof of concept and preliminary testing study, 2000, K. Rennie, T. Rowsell, S.A. Jebb, D. Holburn & N.J. Wareham.

Ironman Speed and Distance System, Oct. 4, 2002, Timex (downloaded from www.timex.com).

Ironman Speed Distance System—Once Again Timex Revolutionizes the Sportwatch, Oct. 4, 2002, Timex (downloaded from www.timex.com).

Polar USA—Product Detail S-610, Oct. 4, 2002, PolarUSA (downloaded from www.polarusa.com).

Polar USA—Product Detail M91ti, Oct. 4, 2002, PolarUSA (downloaded from www.polarusa.com).

* cited by examiner

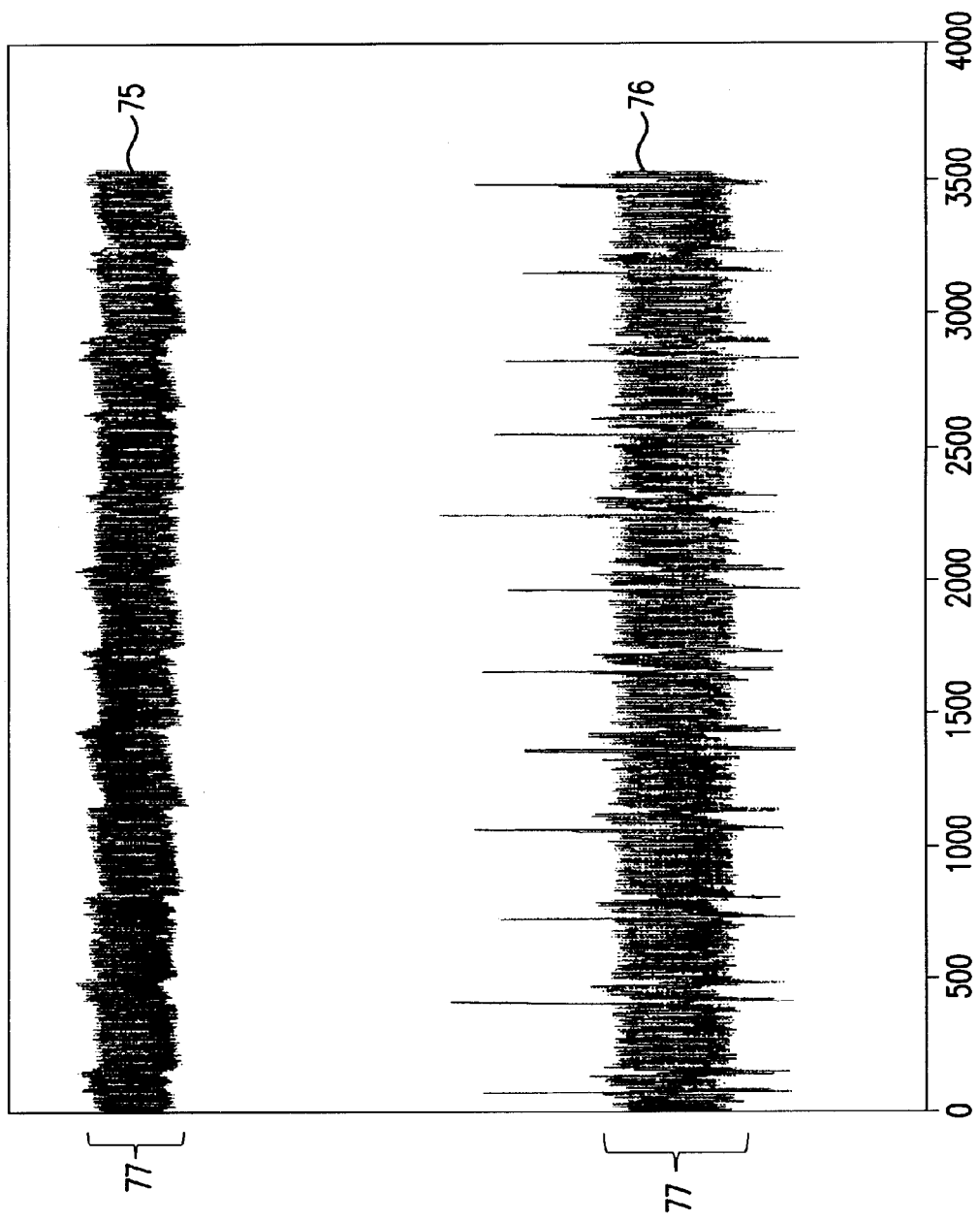

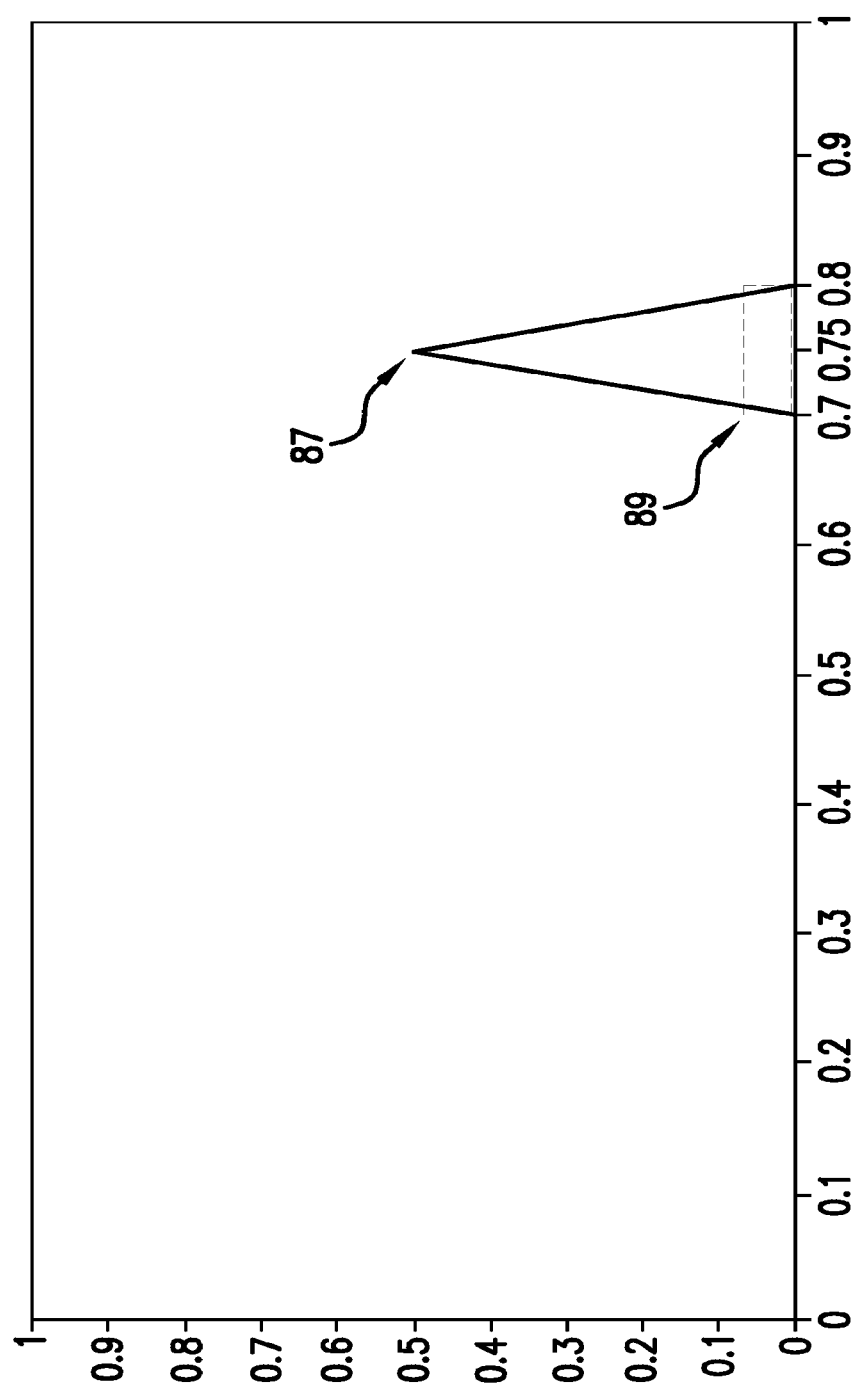

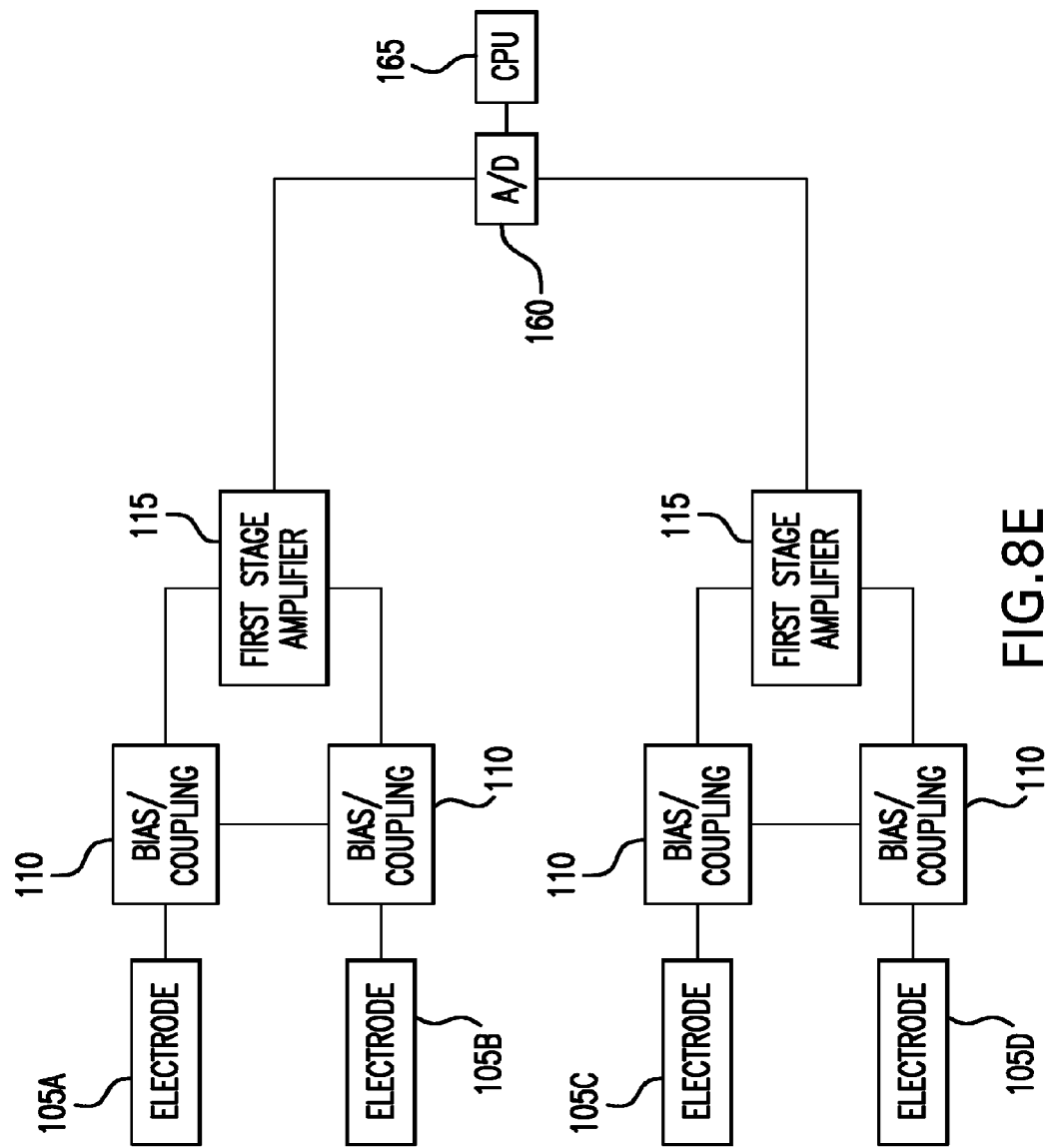

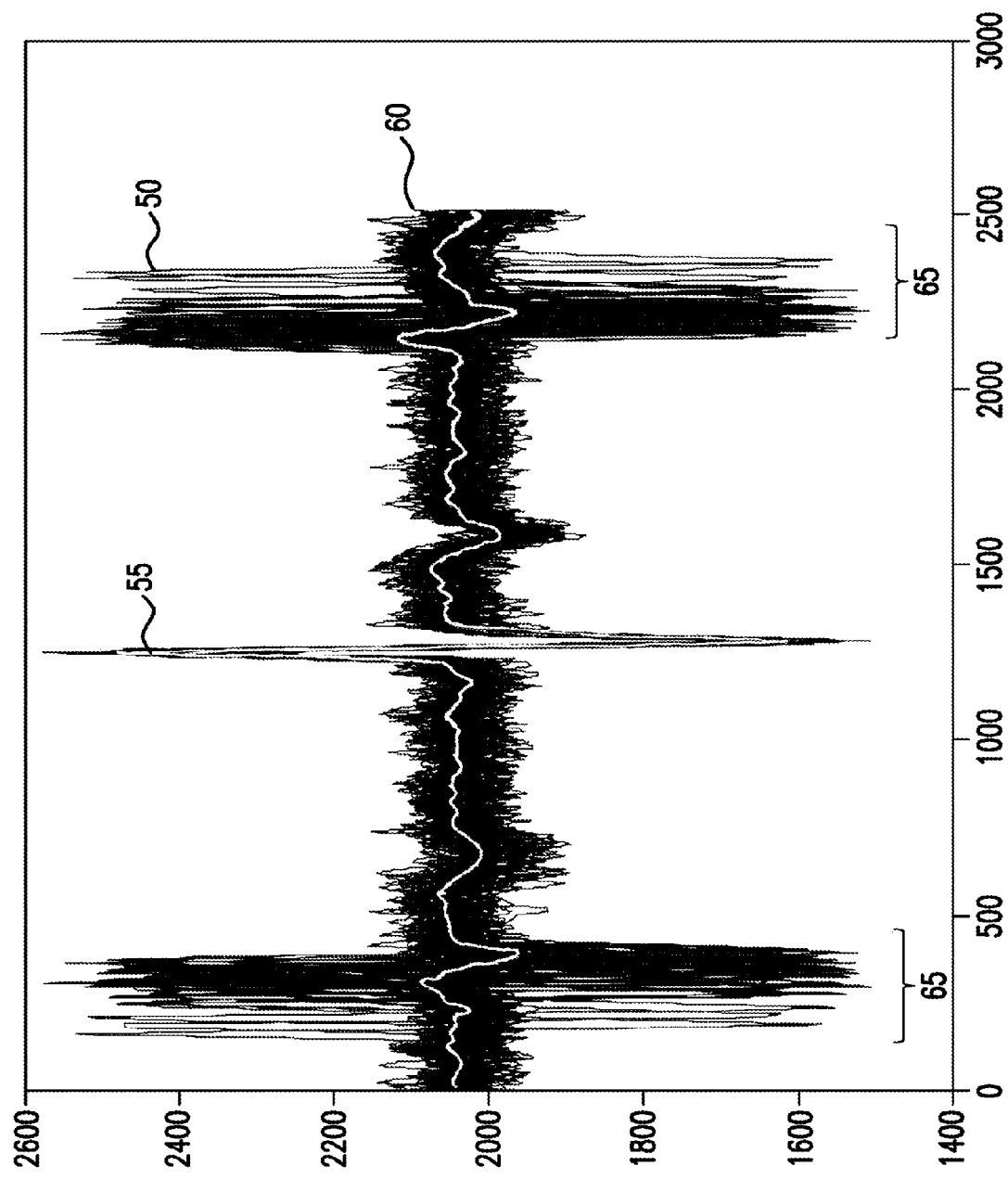

WEARABLE APPARATUS FOR MEASURING HEART-RELATED PARAMETERS AND DERIVING HUMAN STATUS PARAMETERS FROM SENSED PHYSIOLOGICAL AND CONTEXTUAL PARAMETERS

CROSS-REFERENCE TO RELATED APPLICATIONS

This application is a continuation of co-pending U.S. Application 11/928,302 entitled Method And Apparatus For Measuring Heart-Related Parameters And Deriving Human Status Parameters From Sensed Physiological And Contextual Parameters, filed Oct. 30, 2007, which is incorporated herein by reference in its entirety. U.S. Application No. 11/928,302 is a continuation of co-pending U.S. Application 10/940,889 entitled Method and Apparatus for Measuring Heart Related Parameters filed Sep. 13, 2004, which claims the benefit of U.S. Provisional Application Ser. No. 60/502,764, Sep. 12, 2003; U.S. Provisional Application Ser. No. 60/510,013, filed Oct. 9, 2003; and U.S. Provisional Application Ser. No. 60/555,280, filed Mar. 22, 2004, each of which are incorporated herein by reference in their entirety.

BACKGROUND

1. Field

The present invention relates to a method and apparatus for accurately measuring heart related parameters from within a conventionally defined equivalence region of the human body. More particularly, a method and apparatus is disclosed for measuring an ECG signal and other heart related parameters such as heart beats or heart rate from a single limb of the human body. Most specifically, the heart related parameters are taken from the upper left or right arm.

2. Description of the Related Art

The heart is a muscular pump that is controlled by a natural electrical system that causes the heart muscle to contract and pump blood through the heart to the lungs and the rest of the body, carrying oxygen as well as other needed nutrients. The heart can be characterized by a set of parameters that describe the state of the heart, including the frequency and timing of the contractions of the four chambers of the heart, and the pattern of electrical signals causing those contractions. There are many methods of detecting these parameters that are well known in the art, including: sensing the electrical impulses of the heart, sensing the pulse of blood as it moves through arteries, Doppler and other acoustic based methods, capacitance, micro-impulse radar, pressure- and/or motion-based methods such as by utilizing piezo-electric elements or strain gauges, and optical methods in areas where the pulsing of blood can be externally viewed, such as in a pulse-oximeter.

The most well-known and conventional method utilized today for measuring heart-related parameters is the electrocardiogram. An electrocardiogram, or ECG, signal is a surface measurement of the electrical potential of the heart generated by electrical activity in cardiac tissue. This measurement can be made using electrodes placed on the surface of the skin because the entire body is capable of conducting electricity.

FIG. 1 shows a typical ECG signal generated by one heart beat. Signal strength is shown on the Y axis and time is shown on the X axis. The individual spikes and dips in the signal are called waves. The P wave shown in FIG. 1 represents the contraction of the atria. The Q, R, and S waves, referred to as the QRS complex, represent the contraction of the ventricles. The T wave represents the recovery, or repolarization, of the ventricles. The amplitude of a typical ECG signal is approximately 1 to 2 mV when measured from the chest using good electrode contacts.

ECG measurements may be used to provide information about a number of heart related parameters, including, but not limited to, the heart beat rate, or heart rate, for a number of applications, such as medical diagnostic, health awareness and sports performance applications. The most reliable heart rate calculation based upon ECG is performed by detecting each QRS complex, and thus each heart beat, because the QRS complex contains the highest amount of energy and its spectrum differs sufficiently from the spectrum of movement artifacts. Beats are typically counted at each R point (the peak), and the distance between a first R point and a subsequent R point is known as the R-R interval, which, when inverted, yields the instantaneous heart rate. Other parameters such as the heart-rate variability are also computable from the set of R-R intervals.

As discussed above, the heart is a source of a voltage potential difference resulting from the electrical activity that causes the heart muscles to contract. This potential difference is known in the art as the heart's action potential. An ECG signal is a measurement of this action potential. In addition, the heart is positioned in the left chest area and is oriented at an angle slightly off of vertical. The traditional model of ECG measurement indicates that ECG measurements must be taken across the heart, meaning using electrodes placed on either side of an imaginary line running through the center of the heart. Many different researchers have identified the various sections of the surface of the body in different ways with respect to placing electrodes for measuring different aspects of the heart's electrical activity.

Generally, these placements are identified in two ways. First, pairs of electrodes are often used to measure the electrical potential difference between two points. If two points show an electrical potential signal that varies with the activity of the heart they are said to be not equipotential or therefore inequipotential with respect to one another. Inequipotential therefore refers solely to the difference in the heart's action potential rather than other sources of voltage difference such as EMG. Furthermore, locations are described herein as measuring a different aspect of the heart's electrical activity from other locations when those two locations are inequipotential. The electrodes are conventionally placed in a manner as to obtain maximum differentiation between the electrodes. Conventionally, therefore, the body is divided into quadrants I, II, III and IV, as illustrated in FIG. 1A. Electrodes are conventionally placed in two different quadrants on the body, where the body 1 is divided into four sections, or quadrants, by two planes running through the heart. The location of these planes has been modified over time as knowledge in this field has progressed, but has remained fairly constant in that sagittal plane 2 runs roughly vertically through the heart and the transverse plane 3 roughly horizontally. These two planes are orthogonal to one another when viewed from the two-dimensional perspective from in front of the patient. It is important, for the purposes of this application, to assess the location of these imaginary planes through the heart. Sagittal plane 2, is sometimes considered to be coincident with the medial line of the body. Other views, however, direct the vector along a more canted axis coincident with the slightly asymmetric orientation of the heart within the chest cavity. Transverse plane 3, is orthogonal to sagittal plane 2. For bipolar electrode placements, the two electrodes are conventionally placed in two different quadrants, allowing the measurement of the heart's action potential. The other method of reading ECG signals from the heart is to take single pole readings that utilize a single electrode at one point and then utilize an average of multiple electrodes for the other point. This allows a view of the heart from different directions, and allows the creation of views of the heart not achievable with only two electrodes. The precordial, or chest placements in the standard 12-lead ECG are examples of this sort of placement.

Other models include the Einthoven triangle, which describes a roughly inverted equilateral triangular region on the chest having a base extending between the left and right shoulder joints and an apex approximately located at the base of the ribcage, below the sternum. The model contemplates the angle formed at the right shoulder having a first aspect of the ECG signal, the abdominal angle having a second such aspect and the left shoulder angle having a third aspect. The Bayley triaxial system and the Hexaxial system each divide the chest and abdominal area into a larger number of sections or regions, each of which is assigned a single aspect or mixed aspect of the ECG signal.

All of the prior art location identification systems require electrodes placed in at least two of the quadrants of the body. The surface area of each quadrant is defined herein, therefore, as an equivalence region on the body, the portions of the body near the boundaries of the quadrants are further eliminated from such equivalence regions, as it is commonly understood that the boundary can move slightly as the heart beats, the person moves, and that the boundaries can be different between different individuals due to minor difference in heart orientation within the body. The equivalence regions are thus defined as the quadrants illustrated in FIG. 1A. Previous systems for measuring ECG all require having electrodes in at least two of the equivalence regions. These equivalence regions as well as the plethora of different mappings applied to the surface of the body utilized in the prior art can also be understood as following the principle that the signals obtainable within these quadrants are homogeneous as it is assumed that the body is composed of a homogeneous material.

Several prior art devices exist for measuring ECG based on the traditional model. For example, clinical or medical ECG devices use several electrodes placed on the chest, arms and legs to measure a number of different ECG signals from selected electrode pairs wherein in each pair, one electrode is located in one equivalence region and the other electrode is located in a different equivalence region. The different readings together allow a clinician to get a view of the function of the three dimensional electrical activity of the heart from a number of different angles. In many cases, the devices which provide the ability to detect and monitor the heart related parameters is stationary and is intended to monitor a stationary patient.

Such devices, while highly accurate, are very expensive and cumbersome and thus do not lend themselves well to ambulatory or long term uses such as in a free living environment. Holter monitors are devices that may be used for continuous, ambulatory ECG measurement, typically over a 24-48 hour time period. These Holter devices collect raw electrical data according to a preset schedule, or frequency, typically 128 hz or 256 hz. These devices must therefore contain a significant amount of memory and/or recording media in order to collect this data. The physical bulk and inconvenient accessories of this device restricts its continuous use to a relatively short time frame. Each device comprises at least two electrodes for clinical or monitoring data detection and typically a third electrode for ground. The leads are designed to be attached to the chest across the heart, or at least across the conventionally understood sagittal plane 2, and a monitoring device connected to the electrodes is carried or worn by the patient, which is typically a heavy rectangular box clipped to the patient's waist or placed in a shoulder bag. The sensors utilized in conjunction with the device are affixed according to a clinical procedure, wherein the skin under the electrode or sensor is shaved and/or sanded and cleaned with skin preparation liquids such as alcohol prior to application to improve signal quality. Consequently, the sensors are not easily interchanged and may limit physical or hygienic activity. Holter monitors are relatively expensive and for the reasons listed above, are not comfortable for long term and/or active wear situations.

Loop monitors are configured and worn similarly, yet are designed to work for longer periods of time. These systems are designed to record shorter segments or loops of raw data or morphology when the wearer signifies, by pressing a time stamp button that they are doing an activity of interest or feeling a chest or heart related pain. The device will typically record 30 seconds before and 30 seconds after the time stamp. While some success with respect to longer term wearability and comfort is achieved, these loop monitor devices are still inconvenient for everyday use, and include lead wires from the device, snap on sensors affixed to the body by adhesives which require daily skin preparation and periodic re-alignment of the sensors to the original positions.

More recently, a few monitors have also been provided with some automated features to allow the device, without human intervention, to record certain loops when certain preset conditions or measurement thresholds are achieved by the detected heart related activity, such as an abnormal beat to beat interval or a spike in heart rate. Implantable loop recorders have also been developed, which provide similar functionality, with the attendant inconvenience and risks associated with an invasive implant.

Another diagnostic device is known as an event recorder, and this device is a hand held product, with two electrodes on the back, some desired distance apart with recording capabilities where a patient is instructed to place this device against the skin, over the heart or across the sides of the body in order to record a segment of data when the patient is feeling a heart related symptom. This device is not utilized for continuous monitoring, and has memory capability for only a limited number of event records. Once the media storage is filled, there is a facility on the device to communicate the data back to a clinic, clinician, service, or doctor for their analysis, usually by telephone.

While not designed for medial or clinical applications per se, a number of chest strap heart rate monitors have been developed that may be used to measure heart rate from ECG, with some recent devices being capable of recording each detected heart beat, recorded in conjunction with a time stamp in the data. Examples of such conventional monitors commercially available include Polar Electro Oy, located in Oulu, Finland and Acumen, Inc. located in Sterling, Va. These chest strap monitors are designed to be wrapped around the torso beneath the chest and include two electrodes positioned on either side of the heart's conventionally understood transverse plane 3 for measuring an ECG signal. The device is placed just below the pectorals, with conventional electrode positioning. The device is placed at this location because noise and motion signal artifacts from muscle activity is minimal and the signal amplitude is quite robust, consistent and discernable by a circuit or software application. Chest strap monitors of this type, while promoted for use in exercise situations, are not particularly comfortable to wear and are prone to lift off of the body during use, particularly when the wearer lies on his or her back.

Finally, a number of watch-type ECG based heart rate monitors are commercially available, such as the MIO watch sold by Physi-Cal Enterprises LP, located in Vancouver, British Columbia. Such watches include a first electrode attached to the back of the watch that, when worn, contacts one arm of the wearer, and one or more second electrodes provided on the front surface of the watch. To get an ECG signal, and thus a heart rate, a wearer must touch the second electrode(s) with a finger or fingers on the opposite hand, that is, the hand of the arm not wearing the watch. Thus, despite being worn on one arm, the watch measures ECG according to the conventional method, being across the heart, again on either side of the heart's conventionally understood sagittal plane 2, because the two electrodes are contacting both arms. Such watches, while comfortable to wear, only make measurements when touched in this particular manner and thus are not suitable for monitoring ECG and heart rate continuously over long periods of time or while conducting everyday activities such as eating, sleeping, exercising or even keyboarding at a computer.

Matsumara, U.S. Pat. No. 5,050,612, issued Sep. 24, 1991, discloses the use of a multi-electrode sensing watch device, identified as the HeartWatch, manufactured by Computer Instruments Corporation, Hampstead, N.Y., for certain types of heart parameter detection. While Matsumara discloses that the conventional use of the HeartWatch device is in conjunction with a chest strap, he also identifies an alternative use which relies solely on the multisensor watch device itself. The device has two electrodes at different distances along the arm from the heart, and the detected waveform from one electrode is subtracted from the other to obtain a resultant signal. Matsumura identifies this signal as not resembling an ECG, but states that it is useful for detecting ST segment depression. No teaching or suggestion of the efficacy of this method for the identification of heart rate or other heart related parameters is made.

As described above, the traditional models of ECG measurement do not contemplate the action potential of the heart, and thus ECG, being detected and measured from two points within a single quadrant or within a single equivalence region. Moreover, the traditional model rejects the measurement of the action potential from two locations on the same limb. The prior art does contemplate some sensor placements which take advantage of the three dimensional nature of the human body and allow for measuring the heart's action potential between electrodes placed on the front and back of the body, or between spots high on the torso and low on the torso, but on the same side of the body. One skilled in the art would recognize that the prior art only utilized sensor placements that included two or more electrodes in multiple quadrants or equivalence regions.

Another significant shortcoming of ambulatory devices is electrical noise. Noise is detected from both ambient sources surrounding the body, movement and organ noise within the body, and most significantly, the movement of the body itself, including muscle artifacts, motion artifacts, skin stretching and motion between the electrode and the skin. A variety of patents and other references relate to the filtering of noise in many systems, including heart rate detection. In Zahorian, et al., U.S. Pat. No. 5,524,631, issued Jun. 11, 1996, a system is disclosed for detecting fetal heart rates. A significant noise problem exists in that environment, including the heart action of the mother, as well as the significant noise and distortion caused by the fetus' location within a liquid sac inside the mother's abdomen. Zahorian utilizes multiple parallel non linear filtering to eliminate such noise and distortion in order to reveal the fetus' heart rate. The system, like many of the prior art, is unconcerned with the wearability of the monitoring device or the ability to continuously monitor the subject over a long period of time.

None of the above systems identified above combine wearability and accuracy in a compact device. What is lacking in the art, therefore, is a device which provides the ability to measure ECG from two locations in a single equivalence region, such as within a single quadrant as shown in FIG. 1A or on a single limb. Although there are some examples in the prior art that recognize the possibility of inequipotential pairs within a single equivalence region, that the teachings of the prior art fail to utilize these pairs for obtaining a viable signal. There are several barriers to the ability to utilize these signals from unconventional locations, including the small amplitude of the signal, which can be less than one tenth of the signal measured at most conventionally placed electrode locations, the high amount of noise with respect to that signal, as well as the significant effort and risk required to overcome limitations in accuracy, amplitude, and noise obtained from unconventional placements. What is further lacking in the art is such a device which is relatively small in size and adapted for longer periods of continuous wear and monitoring, in conjunction with sensors which minimize the requirement of clinical observation, application or preparation. Such a device provides new opportunities for continuous heart monitoring, including improved comfort, less complex products, and improved compliance with monitoring. Additionally, what is lacking in the art is the ability to combine the continuous monitoring of the heart related parameters with a device which can detect, identify and record the physical activities of the wearer and correlate the same to the heart related parameters.

SUMMARY

A monitor device and associated methodology are disclosed which provide a self contained, relatively small and wearable package for the monitoring of heart related parameters, including ECG. The monitor device is primarily a simple, unobtrusive housing which is wearable in the sense that it is temporarily affixed to the user's body, but also wearable in the sense described in Stivoric, et al., U.S. Pat. No. 6,527,711, issued Mar. 4, 2003, the disclosure of which is incorporated by reference hereto. Stivoric teaches that the sizing, flexibility and location of items attached to the body significantly affect the ability of the wearer to recognize the item as part of the body, reducing the irritation factor associated with wearing such an item for extended periods of time. Furthermore, the use of the appropriate shapes, materials and locations reduces the interference of the item with normal body movement and activity. Each of these factors increases the wearability of the item and therefore increases the compliance of the wearer with the need for long term and continuous wear.

More specifically, the monitor device may be of a type described in Teller, et al., U.S. Pat. No. 6,605,038, issued Aug. 12, 2003, the specification of which is incorporated herein by reference. The primary focus of the monitor device itself is to provide the functionality described below in a housing or other package which is comfortable for long term wear, remains in place during normal daily activity so as to continuously provide a quality signal or data record and also reduces the noise or other interference to that signal or record created by the device itself. One focus of the device is to provide a self-contained housing which incorporates all or at least the majority of the operating hardware. The monitor device, in addition to the Teller device, may further include, as an accessory or rigid housing substitute, a large sized adhesive strip, similar to that used for cuts and abrasions which contains the sensor package within the current location of the absorbent material. Reduction of weight and bulk is very important to increasing the ability for the device to remain affixed in both the right location and with proper contact to the body, especially under rigorous conditions, such as exercise. The device is easy to put on and take off without need for extensive or clinical skin preparation, if any. The device is provided with an appropriate type and strength of adhesive required to keep the weight of the device from disconnecting any snaps or other connections, or pulling the electrode off of the skin. One primary advantage of the device is the elimination of long lead wires which, in addition to being unsightly and inconvenient, act as large antennas for creating noise input to the system. Reduction in the amount of snap connections also reduces these noises, which are common for Holter and loop devices. While not necessarily possible with the current state of processor and sensor size, it is clearly contemplated that the instant system, given the appropriate miniaturization of hardware, could be as simple as sliding on a watch or pair of glasses, utilizing the same basic methodology and equipment identified herein.

Specifically, a monitoring device is disclosed which includes at least one or more types or categories of sensors adapted to be worn on an individual's body. The sensor or sensors, which may include multiple electrodes or other subordinate sensing devices of equivalent type, may be drawn from the categories of contextual and physiological sensors. The physiological sensors may be selected from the group consisting of: respiration sensors, temperature sensors, heat flux sensors, body conductance sensors, body resistance sensors, body potential sensors, brain activity sensors, blood pressure sensors, body impedance sensors, body motion sensors, oxygen consumption sensors, body chemistry sensors, blood chemistry sensors, interstitial fluid sensors, body position sensors, body pressure sensors, light absorption sensors, body sound sensors, piezoelectric sensors, electrochemical sensors, strain gauges, and optical sensors. Sensors are incorporated to generate data indicative of detected parameters of the individual. There may be one or more such parameters of the individual, with at least one such parameter being a physiological parameter. The apparatus also includes a processor that receives at least a portion of the data indicative of at least one physiological parameter. Preferably, the device is specifically directed to the detection of a single heart related parameter, heart beats. It is to be specifically understood that additional parameters may be detected with or without additional sensors. The processor may be adapted to generate derived data from at least a portion of the data indicative of such detected parameters, wherein the derived data comprises an additional parameter of the individual. The additional parameter is an individual status parameter that cannot be directly detected by any of the sensors.

The sensors may be physiological sensors, or may be at least one physiological sensor and one or more optional contextual sensors. The monitoring device may further include a housing adapted to be worn on the individual's body, wherein the housing supports the sensors or wherein at least one of the sensors is separately located from the housing. The apparatus may further include a flexible body supporting the housing having first and second members that are adapted to wrap around a portion of the individual's body. The flexible body may support one or more of the sensors. The apparatus may further include wrapping means coupled to the housing for maintaining contact between the housing and the individual's body, and the wrapping means may support one or more of the sensors.

The monitoring device may include, or, optionally, be utilized in conjunction with an external a central monitoring unit remote from the at least two sensors that includes a data storage device. The data storage device receives the derived data from the processor and retrievably stores the derived data therein. The apparatus also includes means for transmitting information based on the derived data from the central monitoring unit to a recipient, which recipient may include the individual or a third party authorized by the individual. The processor may be supported by a housing adapted to be worn on the individual's body, or alternatively may be part of the central monitoring unit.

As a further alternative embodiment, rather than the processor provided in the monitoring device being programmed and/or otherwise adapted to generate the derived or other calculated data, a separate computing device, such as a personal computer, could be so programmed In this embodiment, the monitoring device collects and/or generates the data indicative of various physiological and/or contextual parameters of the user, which is stored in the memory provided. This data is then periodically uploaded to a computing device which in turn generates derived data and/or other calculated data. Alternatively, the processor of the monitoring device could be programmed to generate the derived data with the separate computer being programmed and/or otherwise adapted to include the utilities and algorithms necessary to create further or secondary derivations based on the physiological and/or contextual data, the first level data derived therefrom, data manually input by the user and/or data input as a result of device-to-device interaction uploaded from the monitoring device or a cooperative third device. The computing device in these alternative embodiments may be connected to an electronic network, such as the Internet, to enable it to communicate with a central monitoring unit or the like.

The apparatus may be further adapted to obtain or detect life activities data of the individual, wherein the information transmitted from the central monitoring unit is also based on the life activities data. The central monitoring unit may also be adapted to generate and provide feedback relating to the degree to which the individual has followed a suggested routine. The feedback may be generated from at least a portion of at least one of the data indicative of a physiological parameter, the derived data and the life activities data.

The central monitoring unit may also be adapted to generate and provide feedback to a recipient relating to management of an aspect of at least one of the individual's health and lifestyle. This feedback may be generated from at least one of the data indicative of a first parameter, the data indicative of a second parameter and the derived data. The feedback may include suggestions for modifying the individual's behavior.

The system is designed to collect data continuously, with no interaction of the wearer necessary, but such interaction is permitted for additional functionality such as particular time stamping capabilities, as necessary. The ability to continuously monitor the heart related parameters limits the need for a manual trigger at the time of an event or the detection of a threshold condition based upon the status of the derived data, as described above. While the system is designed to collect data continuously, in some embodiments the user may utilize the timestamp button to signal that certain heart rate parameters should be collected for the time period around the timestamp. An additional functionality of the device is context and activity detection. Through the use of both the physiological and contextual sensors provided in the device, the ability to learn, model, or ascertain what combinations of data parameters relate to certain activities can be achieved. The ability to detect and discern the type of activity in which the user is engaged relieves the user of the need to manually log these activities to correlate with the heart output data during subsequent review.

The functionality of the monitoring devices is predicated upon the detection of multiple inequipotential heart parameter signals within a single equivalence region of the body and more particularly, multiple detectable action potential signals on a single limb. The device and methods identify and monitor certain pairs of points on the body to obtain inequipotential signals with respect to the heart's action potential. The location of the sensors is therefore determined by their relationship to these detectable inequipotential action potential signals, which may be arranged about the planes illustrated in FIG. 1A which separate the various quadrants of the human body.

It is specifically contemplated that the physical form and/or housing for the device is not limited to those embodiments illustrated herein. Additional embodiments which require more flexibility, or are intended to be disposable in nature may eliminate the housing entirely and include the electronic and other functionality in a more temporary or flexible container, such as a patch, which may have tentacle-like extensions or separately wired sensors attached thereto. Preferred locations for the device itself include, the deltoid and tricep upper arm locations identified specifically herein, the back of the base of the neck and adjacent medial shoulder area, the sides of the chest adjacent to the upper arms when at rest along the sides of the body and the femoral areas of the left and right lower front abdomen adjacent the pelvis.

Additionally, the device may be combined with other like devices in a cooperative array, which may be utilized to further process or analyze the signals derived therefrom. For example, in the case of a pregnant woman, a first such device may be positioned to detect the mother's heart related parameters in a location unlikely to detect the fetal heart related parameters and a second such device, especially in the form of an adhesive or other patch, might be located immediately adjacent the fetus on the mother's abdomen. The signals from the mother's device could be utilized to eliminate the noise of the mother's heart related parameters from the fetus' data stream.

Feedback from the system can take many forms, including the standard visual graphical methods, but a preferred embodiment would include audio feedback as well. This audio component may be in the form of a sound that resonates/conducts through the body, like a bone phone or other variant, to make this feeling more intimate and body like, even if the sound is manufactured digitally to represent the beat. A digital or analog stethoscope could be included in the system to assist in the production of an appropriate sound. Such a device on the abdomen could alternatively be made up of an array of Doppler or ECG electrodes to reduce the need to search for the most appropriate signal location. The device may also be adapted to work in conjunction with an implantable device or other consumed data detector.

Further features and advantages of the present invention will be apparent upon consideration of the following detailed description of the present invention, taken in conjunction with the following drawings.

BRIEF DESCRIPTION OF THE FIGURES

The invention and the following detailed description of certain embodiments thereof may be understood by reference to the following figures:

FIGS. 7A through 7D are diagrammatic representations of detected ECG signals through various stages of processing;

FIGS. 7E through 7H are diagrammatic representations of detected ECG signals through various stages of beat detection;

FIGS. 8A through 8F are block diagrams of alternative circuits for detecting an ECG signal from according to an alternate embodiment of the present invention;

DETAILED DESCRIPTION

Conventional thinking in the field of cardiology/ECG is that an ECG signal must be measured across the heart, meaning with electrodes placed in two different quadrants of the heart's conventionally defined sagittal and transverse planes. A device and methodology are disclosed herein which permits the measurement of an ECG signal from certain pairs of points located within regions or areas of the human body previously considered inappropriate for such measurement. The device and methodology disclosed herein focus on the identification of certain locations on the body within the previously defined equivalence regions utilized for electrode location. Many of these electrode locations are within a single quadrant, i.e., when the electrode locations are connected geometrically directly through tissue, the line described thereby does not cross into another quadrant.

In other words, certain points within one quadrant are correlated with the electropotential of the ECG signal conventionally associated with a different quadrant because the potential from the opposite side has been transported to that point internally through what appear to be low impedance non-homogeneous electropotential or electrical pathways through the body, which may be analogized as internal signal leads within the tissue. This methodology therefore focuses on two different aspects of the ECG signal, rather than more narrowly defining these aspects as emanating from certain quadrants of the body. Thus, contrary to the teachings of the prior art, an ECG signal may be detected and measured using pairs of electrodes placed within a single quadrant, but detecting a significant electrical potential difference between the two points. In other words, the two points are inequipotential with respect to one another. In most instances, it is more helpful to envision the electrode locations being located within independent regions of skin surface, separated by a boundary which may be planar or irregular.

Figure 1:
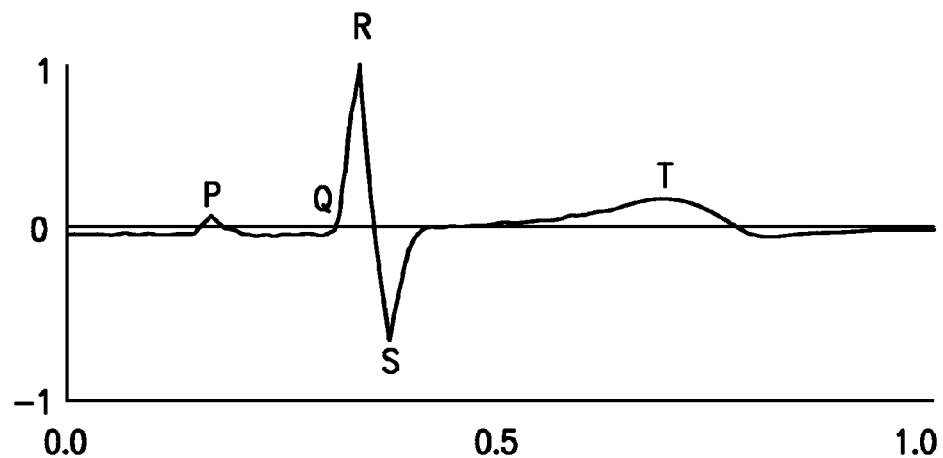
FIG. 1 is a representation of a typical ECG signal.
Figure 1A:
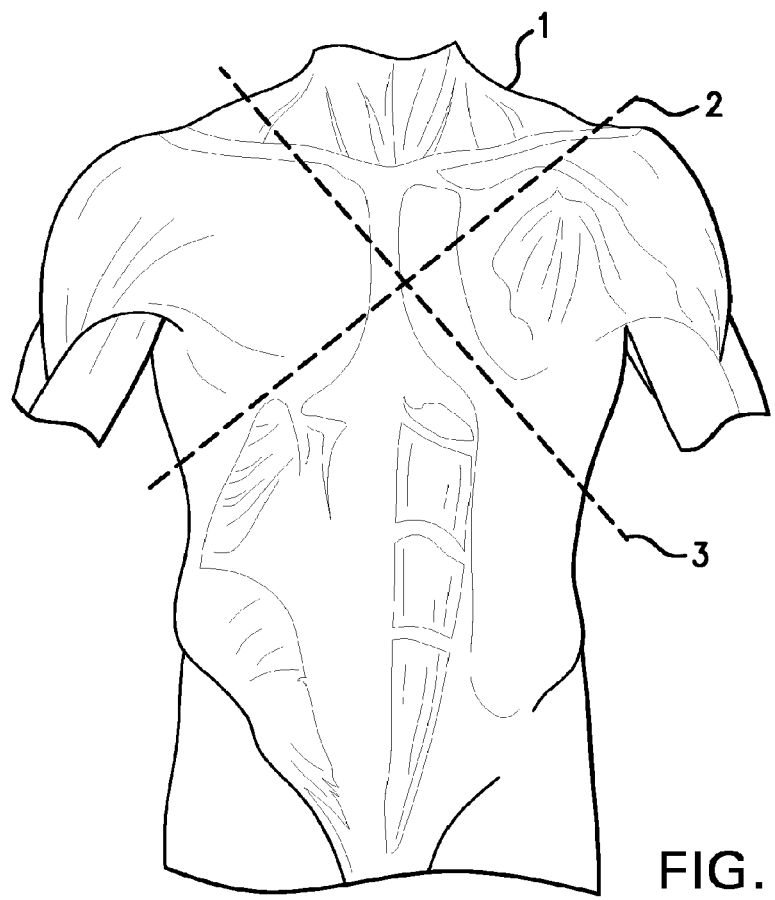
FIG. 1A is a diagrammatic representation of the upper section of the human body showing equivalence quadrants.
Figures 2A, 2B:
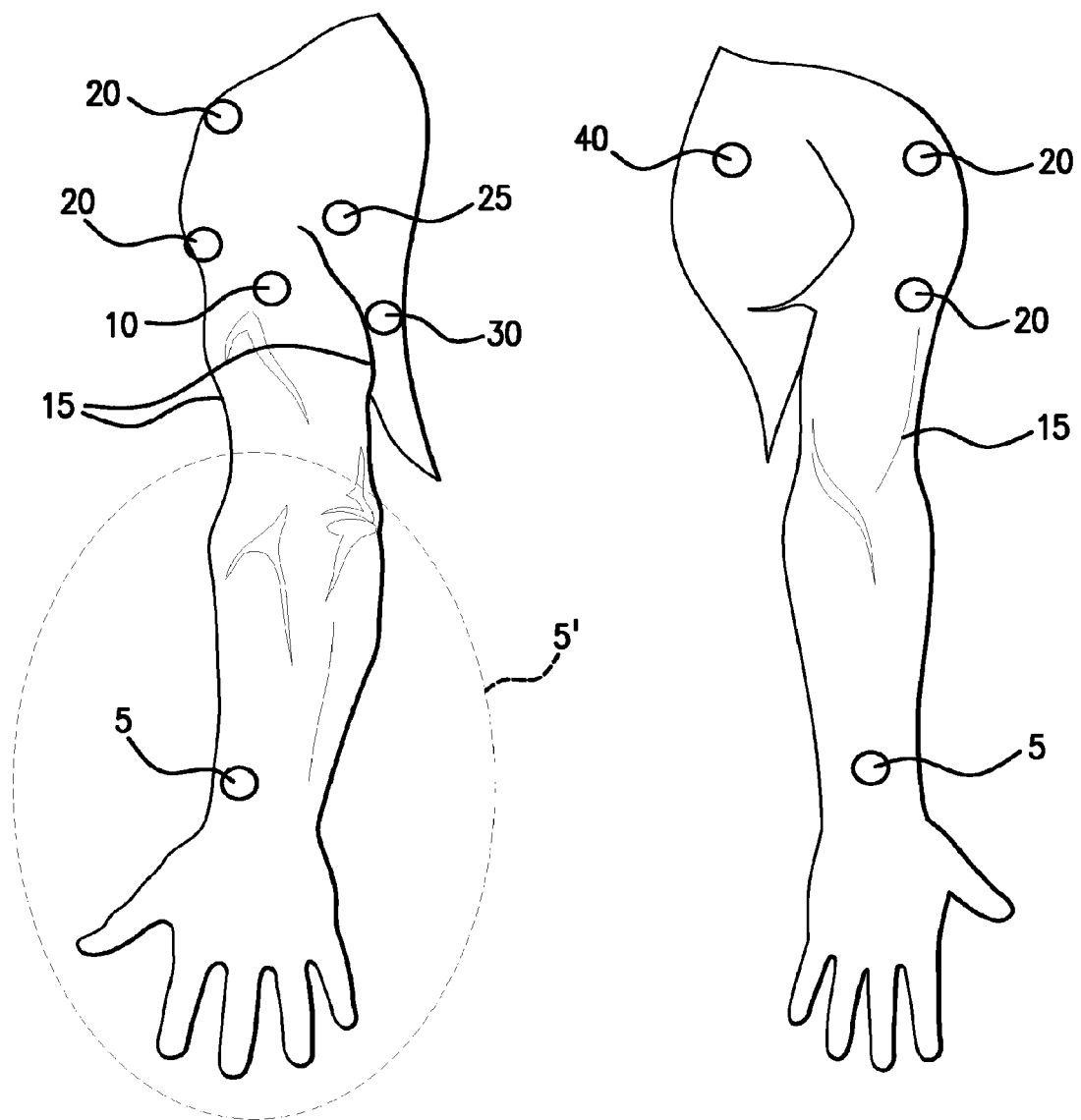
FIGS. 2A, 2B and 2C are back, front and back views, respectively, of the left arm showing electrode placement locations according to an aspect of the present invention.

In the preferred embodiment of the present invention, pairs of locations on or near the left arm have been identified for placement of electrodes to detect the different aspects of the ECG signal. It is to be noted that similar sites within equivalence regions are found at a myriad of locations on the human body, including the right and left arms, the axillary area under the arms, the anterior femoral area adjacent the pelvis, the back of the base of the neck and the base of the spine. More specifically, certain locations on the left arm carry an aspect of the ECG signal and certain locations on or near the left arm carry a different aspect of the ECG signal. It is also to be specifically noted that anatomical names, especially names of muscles or muscle groups, are used to identify or reference locations on the body, though placement of the electrodes need only be applied to the skin surface directly adjacent these locational references and are not intended to be invasive. Referring now to FIGS. 2A and 2B, which are drawings of the back and front of the left arm, respectively, the inventors have found that the left wrist 5, left triceps muscle 10, and the left brachialis muscle 15 are locations that, when paired with locations surrounding the deltoid muscle 20, the teres major muscle 25 and the latissimus dorsi muscle 30, can produce an electrical potential signal that is related to the conventional signal measured between two quadrants. More specifically, the signal from these pairs of points on the left arm correlates with the QRS complex associated with the contraction of the ventricles.

Figure 2C:
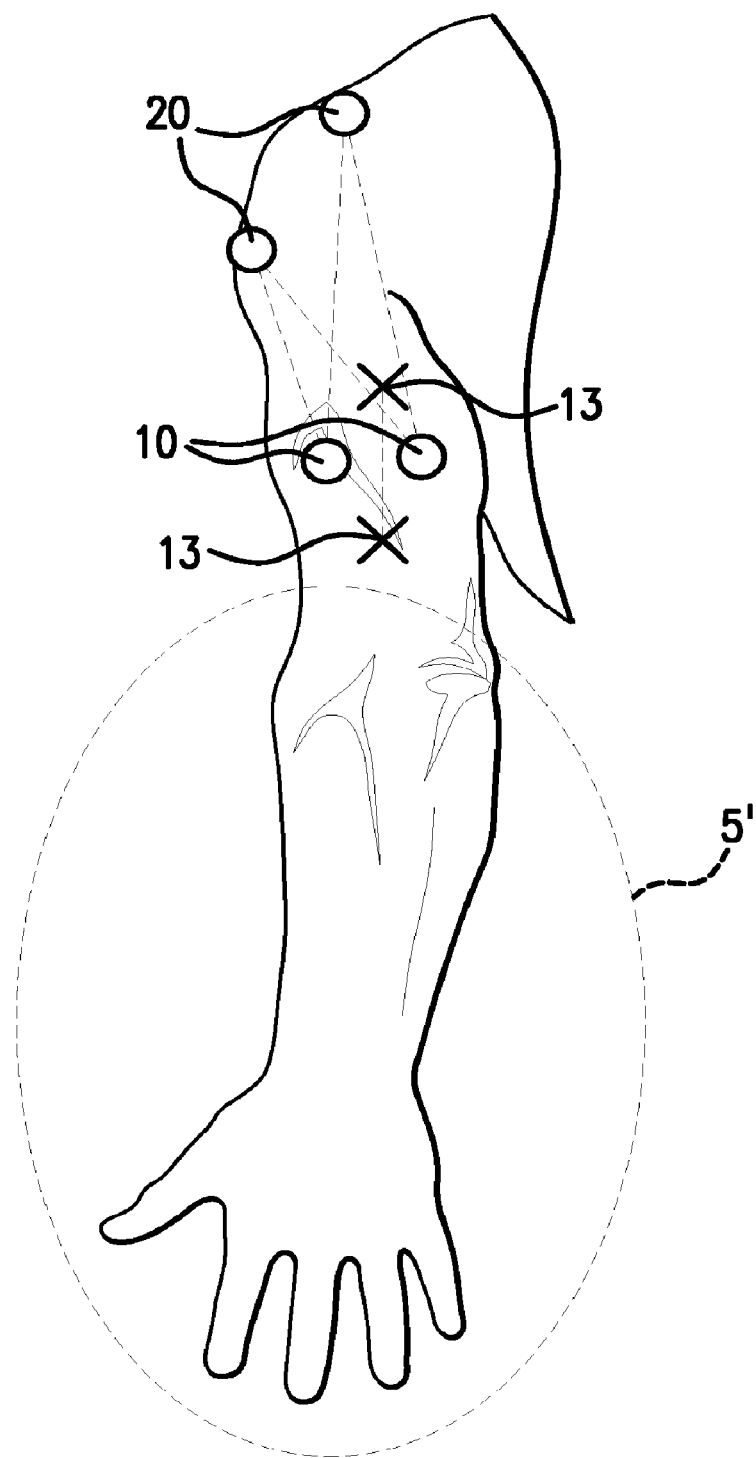

Thus, by placing one electrode on the wrist 5, triceps muscle 10 or the brachialis muscle 15 and a second electrode on the deltoid muscle 20, the teres major muscle 25 or the latissimus dorsi muscle 30, it is possible to detect the action potential of the heart and thus an ECG signal. The electrodes are preferably located near the central point of the deltoid and tricep muscles, are spaced approximately 130 mm and more particularly 70-80 mm apart and tilted at approximately 30-45 degrees toward the posterior of the arm from the medial line, with 30 degrees being most preferred. While certain specific preferred locations on or near the left arm have been described herein as being related to the electropotential of the second aspect of the ECG signal, it should be appreciated those locations are merely exemplary and that other locations on or near the left arm that are related to the electropotential of the second aspect of the ECG signal may also be identified by making potential measurements. It is further to be specifically noted that the entire lower arm section 5' is identified as providing the same signal as wrist 5. Referring now to FIG. 2C, four specific pairs of operative locations are illustrated, having two locations on the deltoid 20 and two locations on the various aspects of the tricep 10. It is to be noted that the dashed lines between the locations indicate the operative pairings and that the solid and white dots represent the relative aspects of the ECG signal obtainable at those locations. Four possible combinations are shown which provide two aspects of the ECG signal. An inoperative pair, 13 is illustrated to indicate that merely selecting particular muscles or muscle groups is not sufficient to obtain an appropriate signal, but that careful selection of particular locations is required.

Figures 3A, 3B:
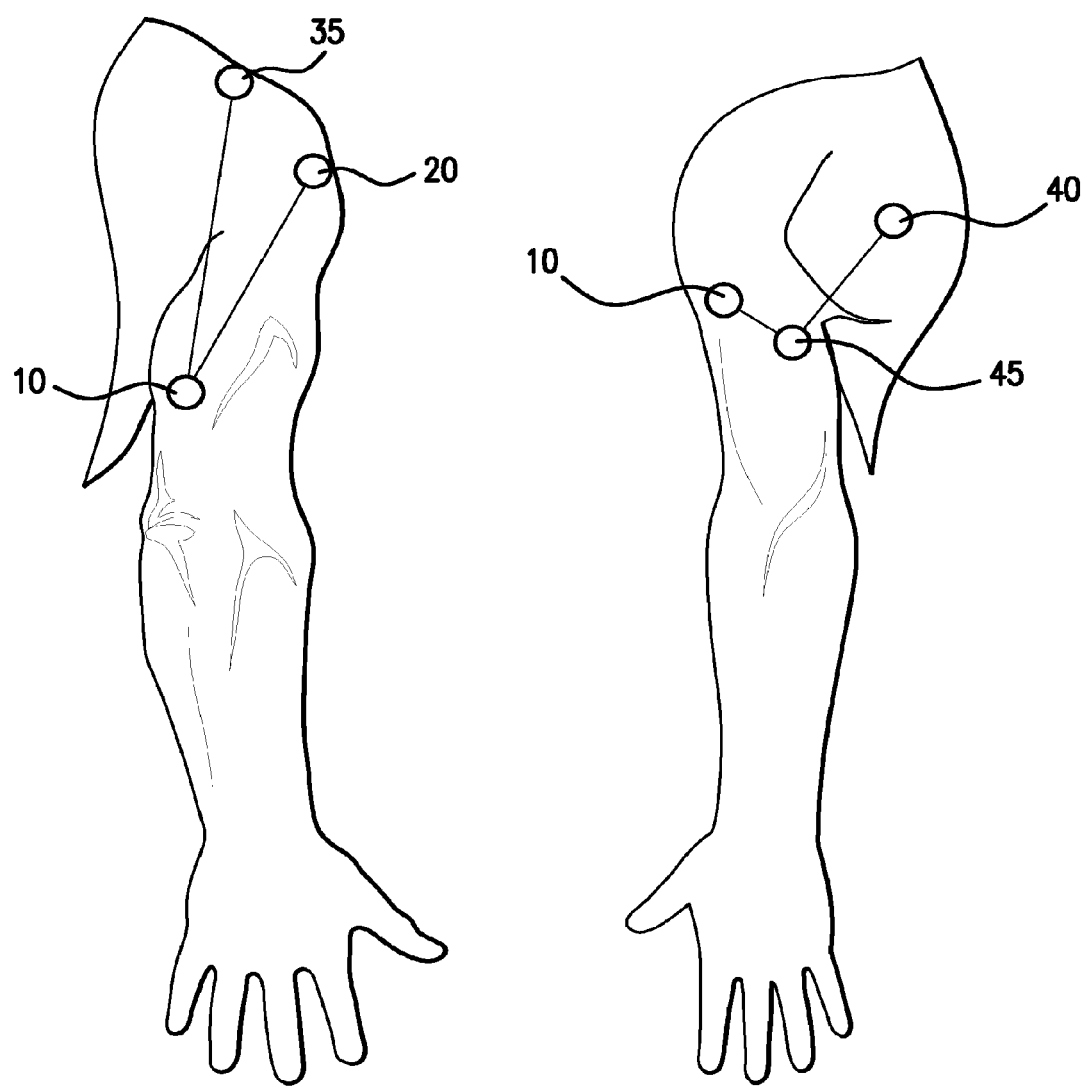
FIGS. 3A and 3B are back and front views, respectively, of the right arm showing electrode placement locations according to an aspect of the present invention.

In another embodiment, pairs of locations on or near the right arm for placing electrodes to detect an ECG signal are identified. Referring to FIGS. 3A and 3B, the base of the trapezius 35, pectoralis 40 and deltoid 20 are locations that are related to the electropotential of the second aspect of the ECG signal, meaning that those locations are at a potential related to the heart's conventionally defined right side action potential. Tricep 10, especially the lateral head area thereof, and bicep 45 are locations that are related to the electropotential of a first aspect of the ECG signal, meaning that those locations are at a potential related to the heart's conventionally defined left side action potential, even though those locations are in quadrant III. Thus, as was the case with the left arm embodiment described above, by placing one electrode on the tricep 10 and a second electrode on the deltoid 20, it is possible to detect the action potential of the heart and thus an ECG signal. Again, while certain specific preferred locations on or near the right arm have been described herein as being related to the electropotential of the first aspect of the ECG signal, it should be appreciated that those locations are merely exemplary and that other locations on or near the right arm that are related to the electropotential of the first aspect of the ECG signal may also be identified by making potential measurements.

Figure 3C:
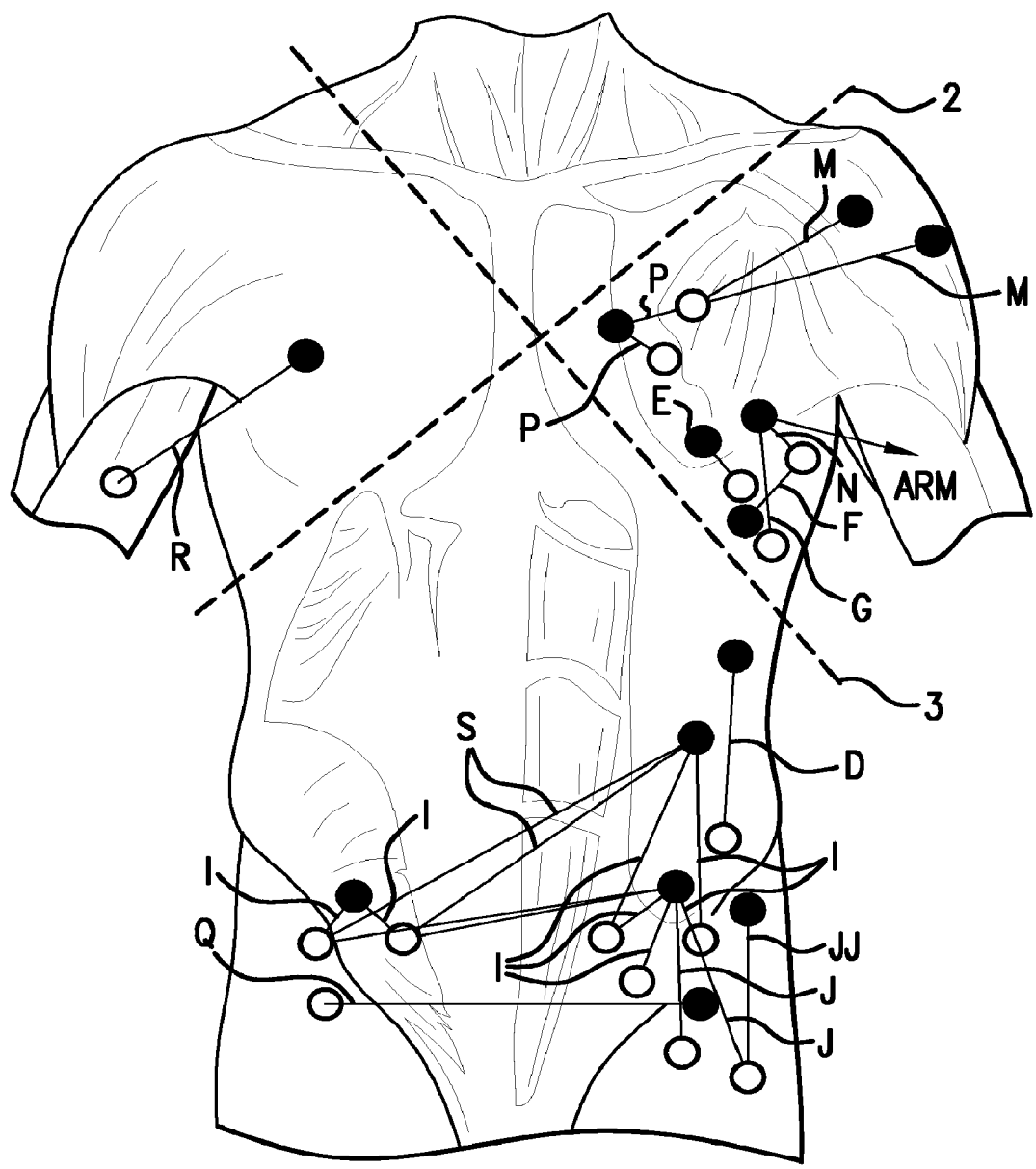
FIGS. 3C, 3D and 3E are front, back and front views, respectively of the torso showing electrode placement locations according to an aspect of the present invention.
Figure 3D:
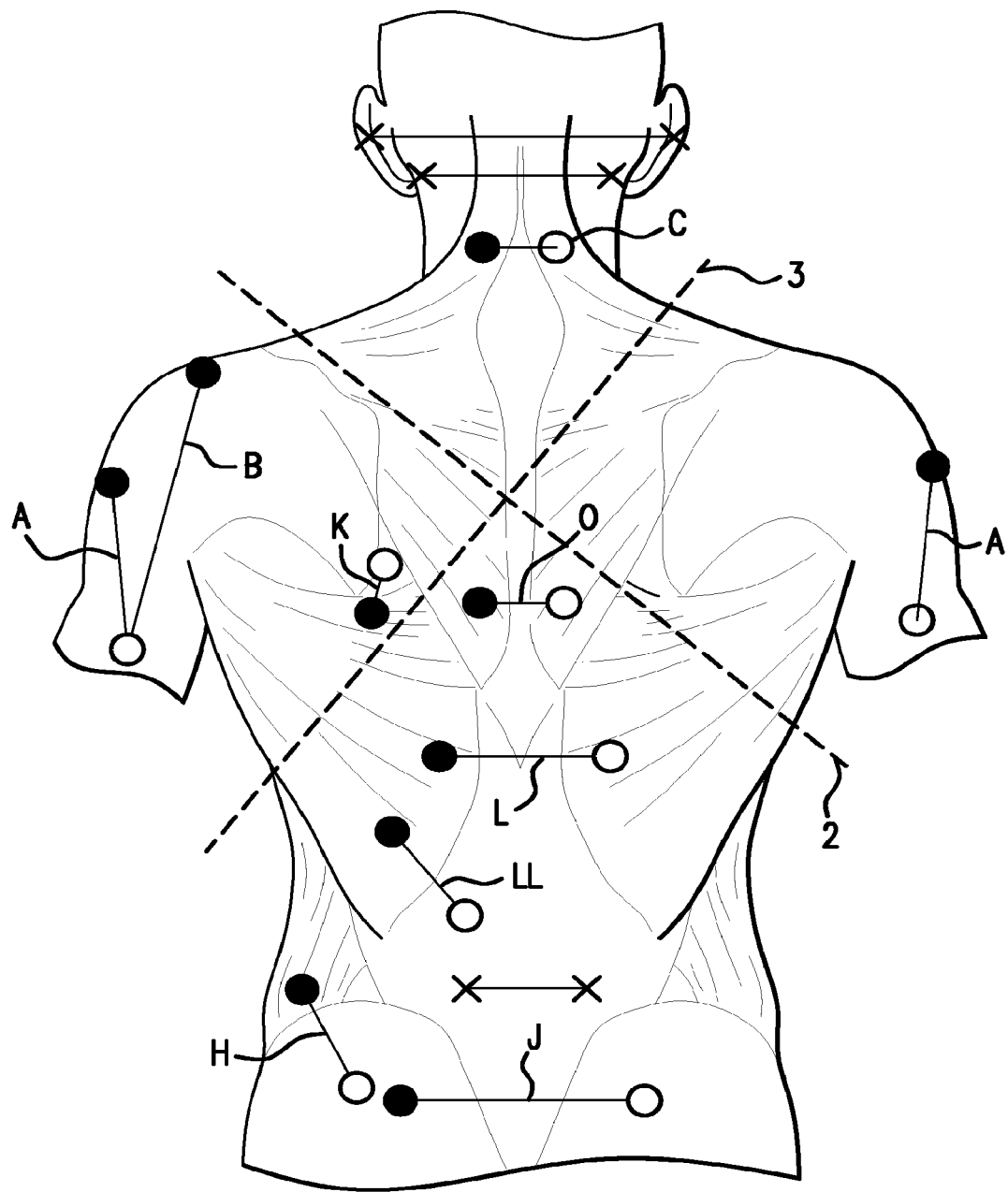
Figure 3E:
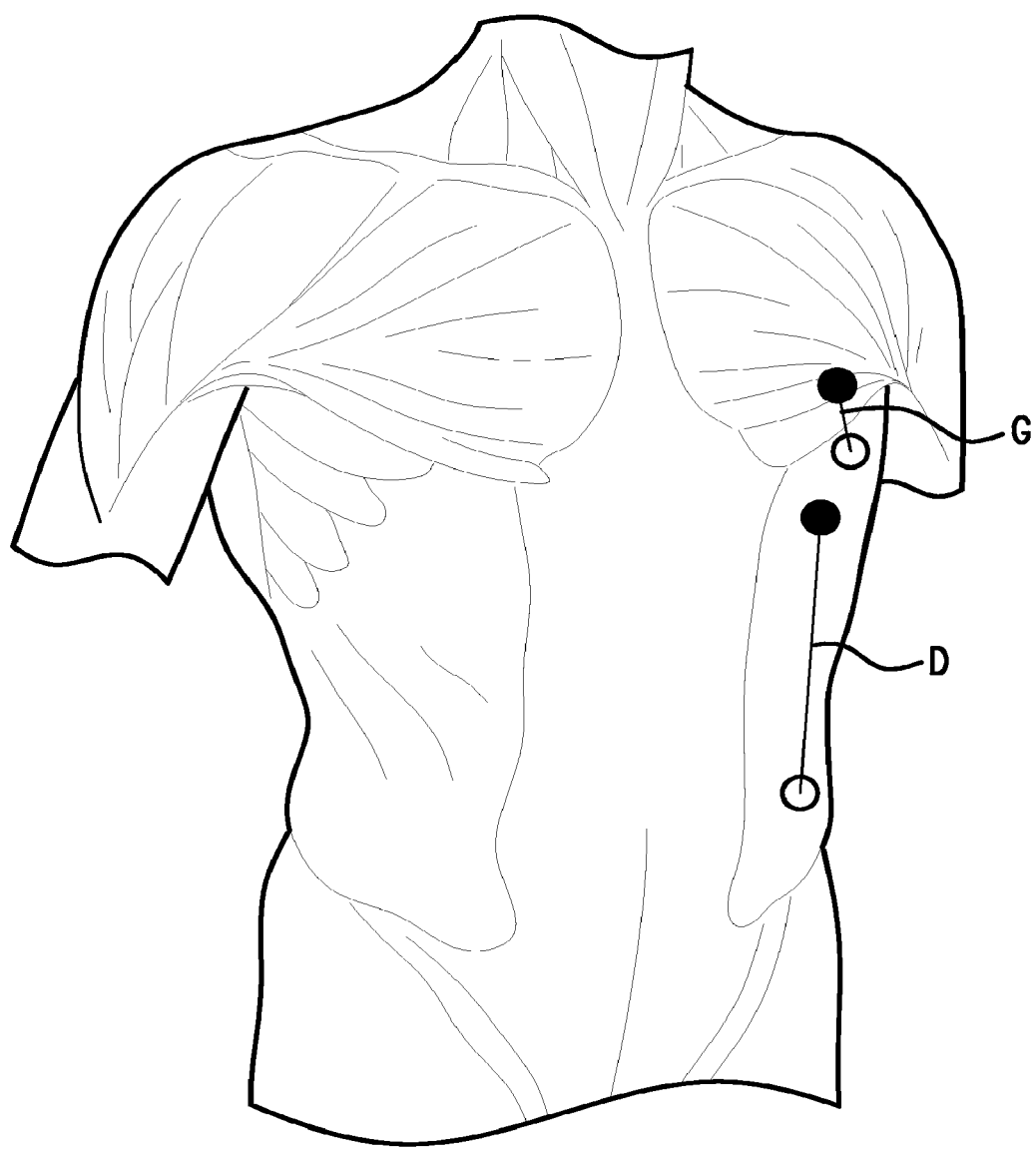

Referring now to FIGS. 3C, 3D and 3E, a series of electrode pair locations are illustrated. In FIGS. 3C and 3D, the conventionally defined sagittal plane 2 and transverse plane 3 are shown in chain line generally bisecting the torso. Each of the operative pairs are identified, as in FIG. 2C by solid and white dots and chain line. Inoperative pairs are illustrated by X indicators and chain line. As previously stated, inoperative pairs are illustrated to indicate that mere random selection of locations, or selection of independent muscle or muscle groups is insufficient to locate an operative pair of locations.

The specific locations identified as within the known operative and preferred embodiments are identified in Table 4 as follows:

| Reference Letter | First Location (White) | Second Location (Solid) |
|---|---|---|
| A | Tricep | Deltoid |
| B | Tricep | Deltoid (top) |
| C | Right Trapezius | Left Trapezius |
| D | Lower External Oblique | Upper External Oblique |
| E | Upper External Oblique | Lower Pectoralis |
| F | Latissimus Dorsi | Upper External Oblique |
| G | Upper External Oblique | Upper External Oblique |
| H | Gluteus Maximus | Lower External Oblique |
| I | Inguinal Ligament | Lower External Oblique |
| J | Lower Lateral Oblique | Rectus Femoris |
| JJ | Inguinal Ligament | Rectus Femoris |
| K | Rhomboid Major | Latissimus Dorsi |
| L | Latissimus Dorsi | Latissimus Dorsi |
| LL | Thoracumbular Fascia | Latissimus Dorsi |
| M | Left Pectoralis | Deltoid |
| N | Latissimus Dorsi | Upper External Oblique |
| O | Lower Trapezius Right | Lower Trapezius Left |
| P | Pectoralis Left | Pectoralis Left |
| Q | Right Thigh | Left Thigh |
| R | Right Bicep | Right Pectoralis |
| S | Right Inguinal Ligament | Left External Oblique |
| T | Upper External Oblique | Left Arm |
| U | Gluteus Maximus Right | Gluteus Maximus Left |

Similarly, it should be understood that the present invention is not limited to placement of pairs of electrodes on the left arm or the right arm for measurement of ECG from within quadrants I or III, as such locations are merely intended to be exemplary. Instead, it is possible to locate other locations within a single quadrant. Such locations may include, without limitation, pairs of locations on the neck, chest side and pelvic regions, as previously described, that are inequipotential with respect to one another Thus, the present invention should not be viewed as being limited to any particular location, but instead has application to any two inequipotential locations within a single quadrant.

One of the primary challenges in the detection of these signals is the relatively small amplitudes or differences between the two locations. Additionally, these low amplitude signals are more significantly masked and/or distorted by the electrical noise produced by a moving body, as well as the noise produced by the device itself. Noise, in this context, refers to both contact noise created by such movement and interaction of the body and device, as well as electronic noise detected as part of the signal reaching the sensors. An important consideration for eliminating noise is increasing the differentiation between the desired signal and the noise. One method involves increasing signal strength by extending one sensor or sensor array beyond the arm, to the chest or just past the shoulder joint. Consideration must be given with sensor placement to two competing desirable outcomes: increased signal strength/differentiation and compactness of the sensor array or footprint. The compactness is, of course, closely related to the ultimate size of the device which houses or supports the sensors. Alternative embodiments, as described more particularly herein, include arrangements of sensors which strive to maintain a compact housing for the device while increasing distance between the sensors by incorporating a fly-lead going to a sensor location point located some short distance from the device itself, such as on the left shoulder, which is still within quadrant I, or even to the other arm. The system further includes an electronic amplification circuit to address the low amplitude signal.

Figure 4:
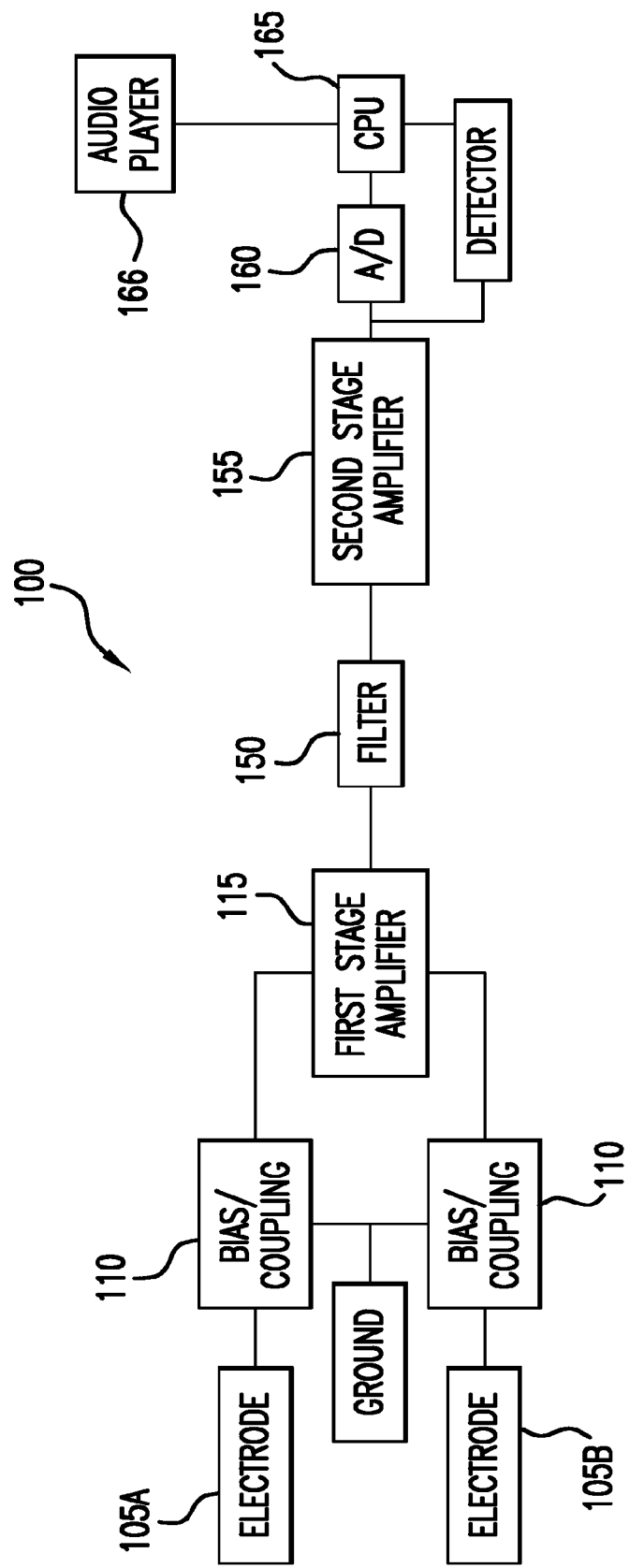
FIG. 4 is a block diagram of a circuit for detecting an ECG signal from according to an embodiment of the present invention.

Referring to FIG. 4, a block diagram of circuit 100 for detecting an ECG signal and for calculating other heart parameters such as heart rate therefrom is shown. Circuit 100 may be implemented and embodied in a wearable body monitoring device such as the armband body monitoring device described in U.S. Pat. No. 6,605,038 and U.S. application Ser. No. 10/682,293, owned by the assignee of the present invention, the disclosures of which are incorporated herein by reference. Addressing FIG. 4 from left to right, circuit 100 includes electrodes 105A and 105B, one of which is connected to a location as described herein that is related to the electropotential of the first aspect of the ECG signal, the other of which is connected to a location on the body that is related to the electropotential of the second aspect of the ECG signal, even if electrodes 105A and 105B are placed within a single quadrant. The interface between the skin and first stage amplifier 115 is critical as this determines how well the heart rate signal is detected. Electrode contact impedance and galvanic potential are important design consideration when designing the first stage amplifier block and the associated bias/coupling networks.

Electrodes 105A and 105B are held against the skin to sense the relatively small voltages, in this case on the order of 20 µV, indicative of heart muscle activity. Suitable electrodes include Red Dot™ adhesive electrodes sold by 3M, which are disposable, one-time use electrodes, or known reusable electrodes made of, for example, stainless steel, conductive carbonized rubber, or some other conductive substrate, such as certain products from Advanced Bioelectric in Canada. It should be noted that unlike the Advanced Bioelectric development, most current reusable electrodes typically have higher coupling impedances that can impact the performance of circuit 100. Thus, to counteract this problem, a gel or lotion, such as Buh-Bump, manufactured by Get Rhythm, Inc. of Jersey City, N.J., may be used in conjunction with electrodes 105A and 105B when placed in contact with the skin to lower the skin's contact impedance. In addition, the electrodes 105 may be provided with a plurality of microneedles for, among other things, enhancing electrical contact with the skin and providing real time access to interstitial fluid in and below the epidermis. Microneedles enhance electrical contact by penetrating the stratum corneum of the skin to reach the epidermis. It is beneficial to make the ECG signal measurements at a position located below the epidermis because, as noted above, the voltages are small, on the order of 20 µV, and the passage of the signal through the epidermis often introduces noise artifacts. Use of microneedles thus provides a better signal to noise ratio for the measured signal and minimizes skin preparation. Such microneedles are well known in the art and may be made of a metal, silicon or plastic material. Prior art microneedles are described in, for example, in U.S. Pat. No. 6,312,612 owned by the Procter and Gamble Company. Based on the particular application, the number, density, length, width at the point or base, distribution and spacing of the microneedles will vary. The microneedles could also be plated for electrical conductivity, hypoallergenic qualities, and even coated biochemically to also probe/sense other physiological electro-chemical signal or parameters while still enhancing the electrical potential for ECG measurement. The microneedles may also be adapted to simultaneously sample the interstitial fluid through channels that communicate with micro level capillary tubes for transferring fluid in the epidermis for sensing electrically, chemically, or electro chemically. Microneedles further enhance the ability of the electrodes to remain properly positioned on the skin during movement of the user. The use of microneedles, however, may limit the ability of the sensors to be mounted on a larger device or housing, as the weight of the larger device may cause the microneedles to shear during movement. In such instances, the microneedle-enhanced sensor may be separately affixed to the body as shown in several embodiments herein. Use of adhesives to supplement the use of microneedles, or alone on a basic sensor is also contemplated. As will be discussed further herein, the use of materials of different flexibilities or incorporating a elastomeric or spring-like responsiveness or memory may further improve sensor contact and locational stability.

In certain circumstances, it is important for a clinician or other observer of the user to determine whether the device has remained in place during the entire time of use, for the purposes of compliance with a protocol or other directive. The use of certain adhesives, or adhesives coupled with plastic or cloth in the nature of an adhesive bandage may be utilized to affix the device to the skin and which would be destroyed or otherwise indicate that removal of the device had occurred or been attempted.

For a wearer to accurately or most affectively place the system on their arm, it may be at least necessary to check that the device is situated in a proper orientation and location, even if the desired location of the electrodes includes an area with significant tolerance with respect to position. In one particular embodiment of the present invention, a device having an array of electrodes 105, such as armband monitoring device 300 described above, is placed in an initial position on the body of the wearer, with each of the electrodes 105 is in an initial body contact position. The device then makes a heart rate or other heart related parameter measurement as described above, and compares the measured signal to a what would be an expected signal measurement for a person having the physical characteristics of the wearer, which had been previously input into the system as more fully described herein, such as height, age, weight and sex. If the measured signal is meaningfully more degraded, as determined by signal to noise ratio or ratio of beat height to noise height, than the expected signal, which would be a preset threshold value, the device gives a signal, such as a haptic, acoustic, visual or other signal, to the wearer to try a new placement position for the device, and thus a new contact position for the electrodes 105. A second measurement is then made at the new position, and the measured signal is compared to the expected signal. If the measured signal is meaningfully more degraded than the expected signal, the new position signal is given once again to the wearer. This process is repeated until the measured signal is determined by the device to be acceptable. When the measured signal is determined to be acceptable, the device generates a second success signal that instructs the wearer to leave the device in the current placement location. The device may initiate this operation automatically or upon manual request.

Circuit 100 also includes bias/coupling network 110, shown as two boxes in FIG. 4 for convenience, and first stage amplifier 115. As will be appreciated by those of skill in the art, the approximately 20 µV potential difference signal that is detected by electrodes 105A and 105B will, when detected, be biased too close to the limits of first stage amplifier 115, described below. Thus, bias/coupling network 110 is provided to increase the biasing of this signal to bring it within the allowable input range for first stage amplifier 115.

Figure 5A:
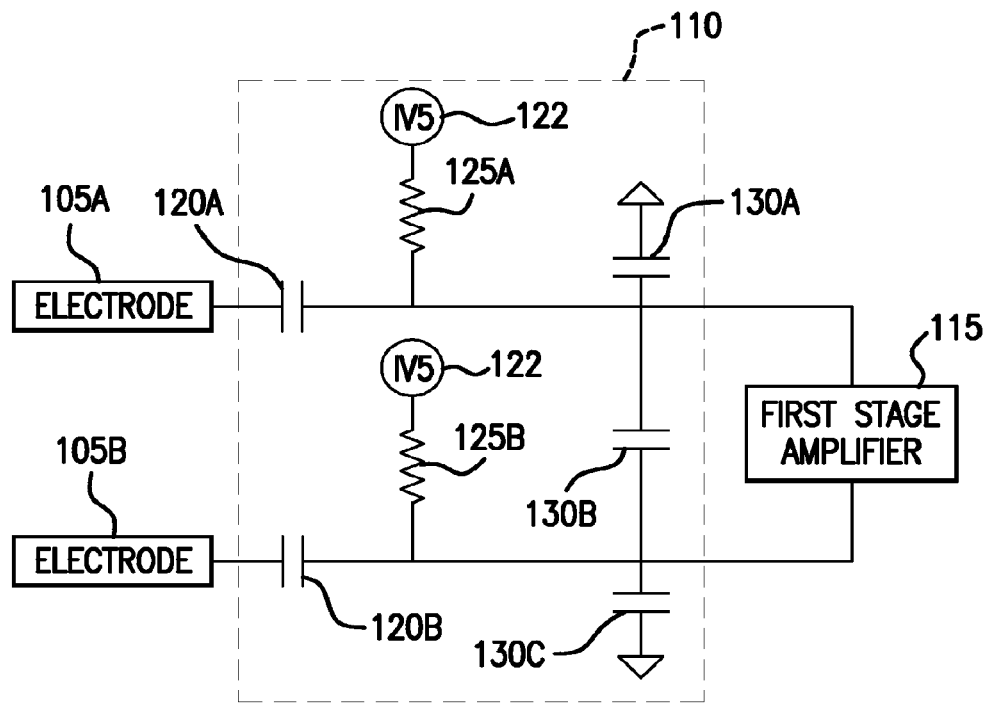
FIGS. 5A and 5B are circuit diagrams of first and second embodiments of the bias/coupling network shown in FIGS. 4 and 7.
Figure 5B:
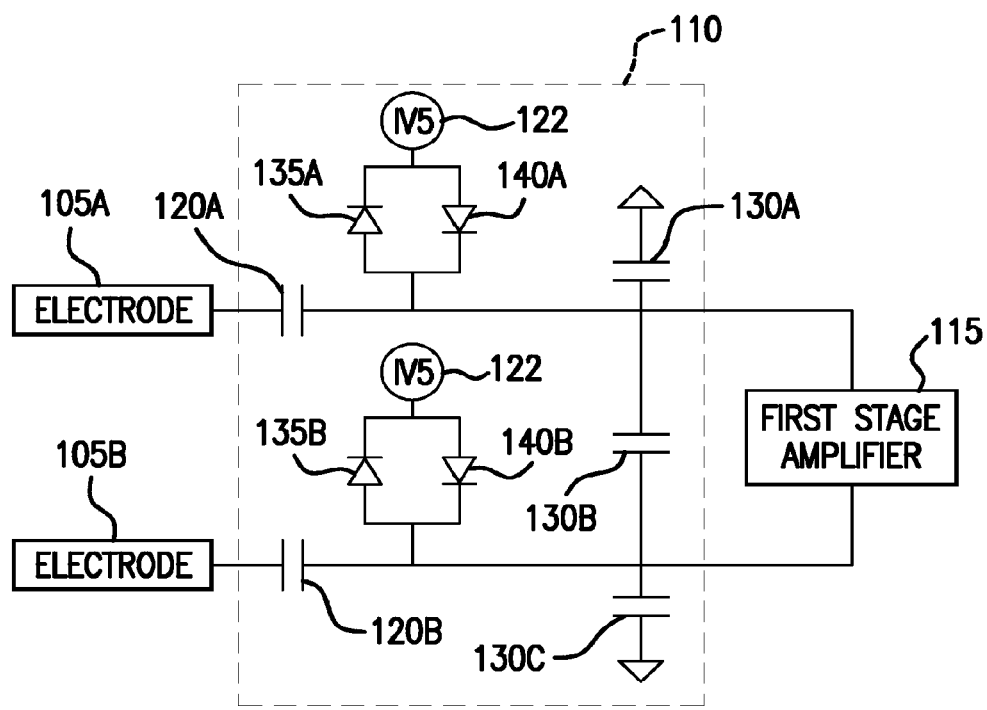

Two approaches to providing bias current for the amplifier inputs are shown in FIGS. 5A and 5B, as will be described more fully herein. Preferably, bias/coupling network 110 will move the bias of the signal up to the middle range of first stage amplifier 115. In the preferred embodiment, as described below, first stage amplifier 115 is a rail to rail amplifier having rails equal to 0 V and 3 V. Thus, bias/coupling network 110 will preferably increase the bias of the voltage potential difference signal of electrodes 105A and 105B to be approximately 1.5 V.

Although not specifically described, the bias/coupling network can be dynamic, in that adjustments can be made based upon the signals being produced when the device is first engaged, or under changing context conditions. This dynamic capability would also accommodate individual differences in amplitude for different placements of similar devices because of user size or other physical characteristics. Experimentation has shown some degree of variation on signal strength based upon distance. Furthermore, changes in signal are expected based on the amount of motion the device is doing relative to the arm, the flexing of the electrodes and their contact with the skin, contractions and relaxations of the muscles below or around the skin contact points and the movement of the body.

Preferably, bias/coupling network 110 employs capacitive input coupling to remove any galvanic potential (DC voltage) across electrodes 105A and 105B when placed on the body that would force the output of first stage amplifier 115 outside of its useful operating range. In addition, the non-zero input bias current of first stage amplifier 115 requires a current source/sink to prevent the inputs from floating to the power supply rails. In one embodiment, bias/coupling network 110 may take the form shown in FIG. 5A. In the embodiment shown in FIG. 5A, bias-coupling network 110 includes capacitors 120A and 120B connected to electrodes 105A and 105B, respectively, which are in the range of 0.1 µF to 1.0 µF and resistors 125A and 125B connected as shown, which have a value of between 2 MΩ to 20 MΩ. As will be appreciated, resistors 125A and 125B provide the bias current for first stage amplifier 115 following Ohm's law, V=IR. In addition, bias/coupling network 110 includes capacitors 130A, 130B and 130C, the purpose of which is to filter out ambient RF that may couple to the high impedance lines prior to the amplifier in the circuit. Preferably, capacitors 130A, 130B and 130C are on the order of 1000 pF. A 1.5 volt mid-supply reference voltage 122 is further provided to keep the signals centered in the useful input range of the amplifiers.

Referring to FIG. 5B, an alternative embodiment of bias/coupling network 110 is shown in which resistors 125A and 125B have each been replaced with two diodes connected back to back, shown as diodes 135A and 140A and 135B and 140B, respectively. In this configuration, with no input signal applied from electrodes 105A and 105B, diodes 135A, 135B, 140A and 140B provide the currents required by first stage amplifier 115 and bias each input slightly away from the 1.5 V reference 122. When a signal is applied to electrodes 105A and 105B, the very small change in voltage, typically 20 µV, results in very small changes in current through the diodes, thereby maintaining a high input impedance. This configuration permits exponentially higher currents to bias first stage amplifier 115 quickly when a large adjustment is necessary, such as is the case during initial application of electrodes 105A and 105B to the body. An added benefit of such a configuration is the increased electro-static discharge protection path provided through the diodes to a substantial capacitor (not shown) on the 1.5 V reference voltage 122. In practice, this capacitor has a value between 4.7 and 10 µF and is capable of absorbing significant electro-static discharges.

Referring again to FIG. 4, the purpose of first stage amplifier 115 is to amplify the signal received from bias/coupling network 110 before it is filtered using filter 150. The main purpose of filter 150 is to eliminate the ambient 50/60 Hz noise picked up by electrodes 105A and 105B when in contact with the body of the user. This noise is often referred to as mains hum. The filter 150 will add some noise, typically in the range of 1 μV, to the signal that is filtered. Therefore, the purpose of first stage amplifier 115 is to amplify the signal received from bias/coupling network 110 before it is filtered using filter 150 so that any noise added by the filtering process will not overwhelm the signal. As will be appreciated, since the signal output by bias/coupling network 110 is on the order of 20 μV, filtering with filter 150 without first amplifying the signal using first stage amplifier 115 will result in a signal that is overwhelmed by the noise added by filter 150. Thus, first stage amplifier 115 is used to amplify the signal with a gain preferably between 100 and 10,000, most preferably 255.

Figure 5C:
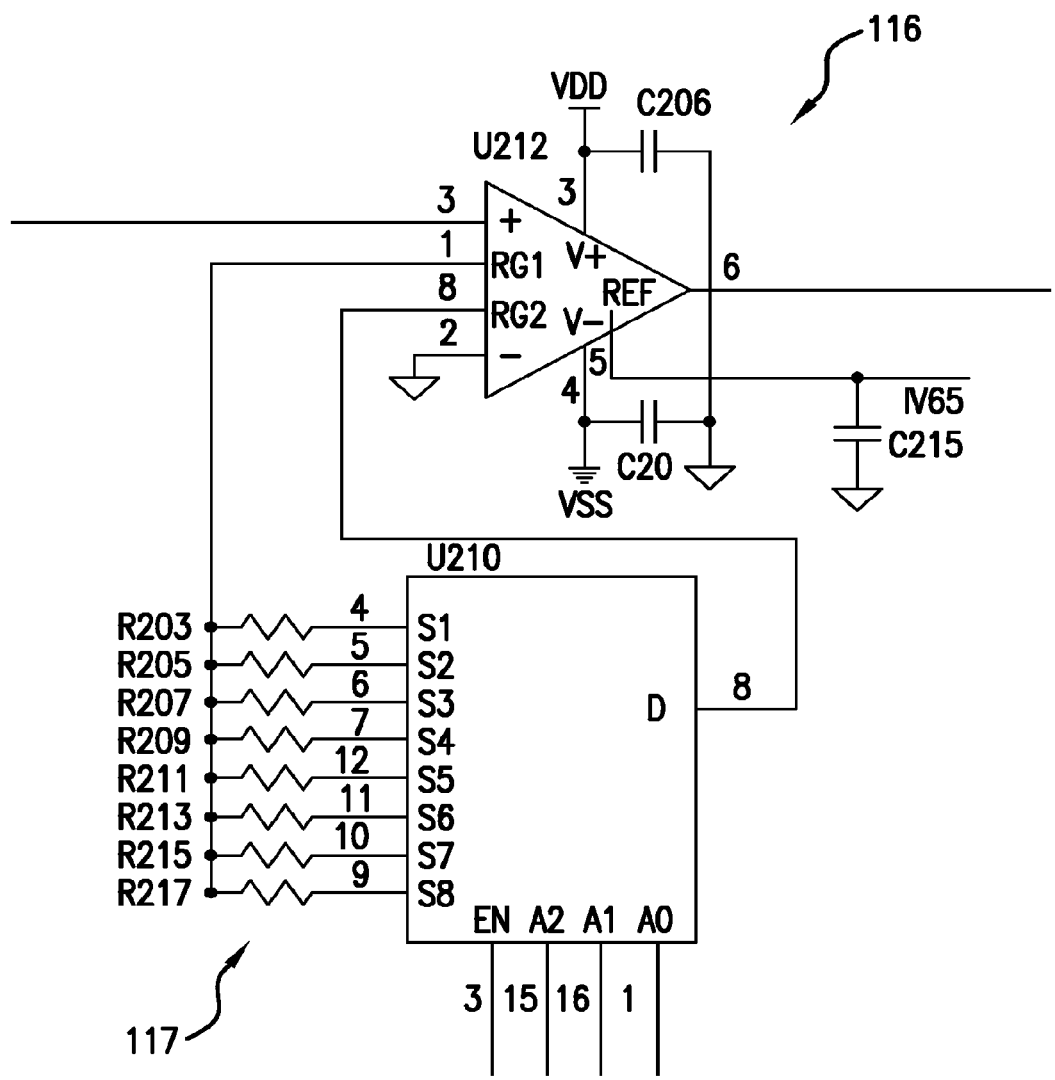
FIG. 5C is a circuit diagram of a first stage amplifier design.

A suitable example of first stage amplifier 115 is shown in FIG. 5C, which includes programmable gain amplifier 116, which is preferably model AD627 sold by Analog Devices, Inc. of Norwood, Mass. or model LT1168 sold by Linear Technology Corporation of Milpitas, Calif. The gain of these amplifiers is determined by a gain select resistor coupled to appropriate inputs of the amplifier. Thus, an input multiplexer 117, such as the model ADG608 multiplexer sold by Analog Devices, Inc. may be used to selectively switch in and out one of a number, preferably 8, of gain select resistors for the programmable gain amplifier used for first stage amplifier 115 during a testing period to determine an appropriate gain select resistor for the amplifier. Once a candidate gain is determined using the input multiplexer in a testing mode, a single fixed resistor for gain can be selected for use in connection with the programmable gain amplifier used as first stage amplifier 115.

Key parameters in selecting an amplifier for first stage amplifier 115 are input bias current, input offset current, and input offset voltage. Input bias current multiplied by the input impedance of the bias/coupling network gives the common-mode input offset voltage of the positive and negative inputs to first stage amplifier 115. Care must be taken to keep the inputs of first stage amplifier 115 far enough from the power supply rails to prevent clipping the desired output signal. As with the bias/coupling network, an alternative design might include a circuit which was able to dynamically limit the input voltage based upon the type of activity, such as power on, initial attachment to the arm, or certain high-motion activities so that the input voltage under normal conditions would be optimum. As one skilled in the art would appreciate, some clipping can be acceptable. Algorithms for detecting heart rate or other heart parameters can work in the presence of some amount of clipping, assuming that the signal to noise ratio remains relatively high.

The input offset current parameter multiplied by the bias impedance gives the differential input voltage that is applied to first stage amplifier 115. This differential voltage is in addition to the input offset voltage parameter that is inherent in the amplifier, and the total input offset is simply the sum of the two. The total differential input voltage multiplied by the gain determines the output offset. Again, care must be taken to keep the output signal far enough from the power supply rails to prevent saturation of the amplifier output. As an example, a bipolar amplifier such as the model AD627 described above has an input bias current of 10 nA, an input offset current maximum of 1 nA, and an input offset voltage of 150 μV (all values are worst case maximums at 25° C.). In order to keep the common-mode input offset to less than 0.5 V, the bias impedance must be no more than 0.5 V/10 nA=50 MΩ. However, the input offset current dictates that in order to maintain a maximum 0.5 V output offset voltage, one must provide an input impedance of no more than 0.5 V/gain/1 nA. For a gain of 100, this resolves to 5 MΩ. For a gain of 500, this resolves to 1 MΩ. Another candidate amplifier for use as first stage amplifier 115 is the Texas Instruments Model INA321 programmable gain amplifier, which has FET inputs. This amplifier has an input bias current of 10 pA and an input offset current of 10 pA (max). In order to keep the common-mode input offset to less than 0.5 V, one must provide an impedance of no more than 0.5 V/10 pA=50 GΩ. However, the input offset current dictates that in order to maintain a maximum 0.5 V output offset, one must provide an input impedance of no more than 0.5 V/gain/10 pA. For a gain of 100, this resolves to 500 MΩ. For a gain of 1,000, this resolves to 50 MΩ.

As an alternative, as will be appreciated by those of skill in the art, first stage amplifier 115 may be implemented in a network of low cost discrete op-amps. Such an implementation will likely reduce the cost and power consumption associated with first stage amplifier 115. As will also be appreciated by those of skill in the art, the same analysis of amplifier input bias current, output saturation, and input bias/coupling applies to such an alternative implementation.

Referring again to FIG. 4, filter 150 is a bandpass network preferably including separate low-pass and high-pass filter sections. The purpose of the low-pass filter section is to eliminate the ambient 50/60 Hz noise picked up by electrodes 105A and 105B when in contact with the body. Preferably, a multi-pole filter is used to achieve a high degree of attenuation. The high-pass filter section eliminates the DC wander of the signal baseline due to galvanic effects in electrodes 105A and 105B, allowing the heart beat spikes forming a part of the measured ECG signal to be more easily detected by hardware or software means.

In one embodiment, filter 150 includes switched capacitor low-pass and high-pass filters with adjustable cutoff frequencies to allow for experimentation. Such a filter 150 may be constructed using the model LTC1164_6 low-pass filter chip sold by Linear Technology Corporation followed by a model LTC1164 high-pass filter chip also sold by Linear Technology Corporation, which chips provide an eighth order elliptical filter with very sharp cutoff characteristics. Experimentation with this implementation has shown that a low-pass cutoff frequency of 30 Hz and a high-pass cutoff frequency of between 0.1 Hz and 3 Hz worked well. Although allowing for flexibility, this implementation is relatively expensive and was found to consume a significant amount of power.

Figure 6:
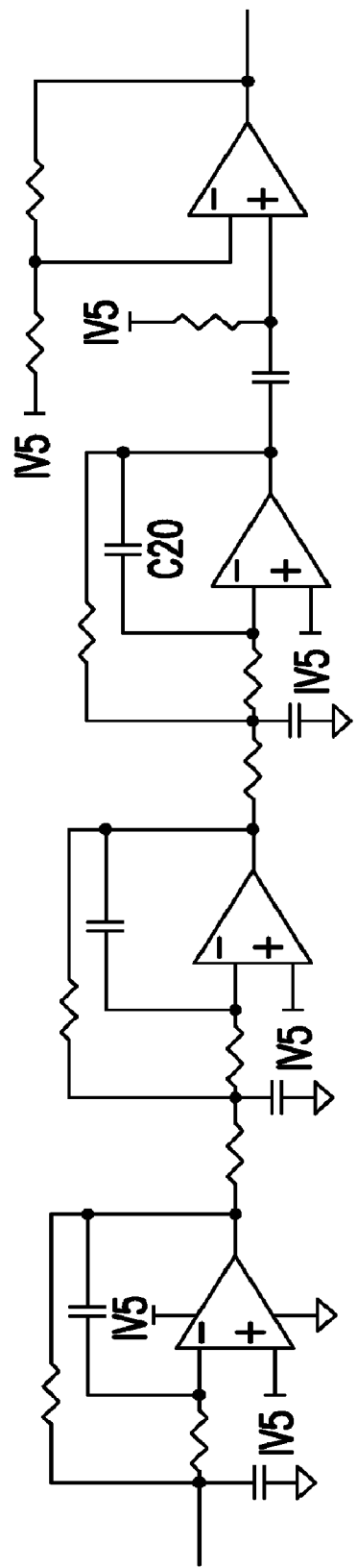
FIG. 6 is a circuit diagram of one embodiment of the filter shown in FIGS. 4 and 7.

An alternative implementation for filter 150 is shown in FIG. 6. The circuit shown in FIG. 6 implements a sixth order active filter using discrete op-amps in a multiple feedback topology. The circuit shown in FIG. 6 consumes less current and costs significantly less than the switched capacitor design described above. Values for the resistors and capacitors shown in FIG. 6 may be selected using a software tree package such as the FilterPro package provided by Texas Instruments. As will be appreciated by those of skill in the art, the different filter styles, such as Butterworth, Bessel, and Elliptic, may be implemented simply by changing component values. The FilterPro package also provides information that is useful in selecting the amplifiers shown in FIG. 6, including necessary bandwidth for each stage. Suitable amplifiers include the models TLV2764 and OPA4347 quad amplifiers sold by Texas Instruments Incorporated of Dallas, Tex. The three-stage (first three op-amps) sixth order filter forming part of the circuit shown in FIG. 6 provides adequate 60 Hz filtering, thereby allowing the fourth op-amp in the circuit to be used for second stage amplifier 155 shown in FIG. 4 and described below. In addition, the R-C Network shown in FIG. 6 that couples the third stage op-amp of the low-pass filter to the fourth op-amp (the gain stage) provides a high-pass network which eliminates DC drift as described above.

Referring again to FIG. 4, circuit 100 includes second stage amplifier 155 for amplifying the signal output by filter 150 to a level that can be directly sampled by analog to digital converter 160. Specifically, if the gain of first stage amplifier 115 is between 100 and 10,000, the amplitude of the signal output by filter 150 will be in the range of 2 mV to 200 mV. Preferably, the gain of first stage amplifier 115 is 500, and therefore the amplitude of the signal output by filter 150 will be on the order of 10 mV. In order to allow for a higher sampling resolution by analog to digital converter 160, second stage amplifier 155 is used to further amplify the signal. Preferably, second stage amplifier has a gain on the order of 30, and therefore would amplify the 10 mV signal in the preferred embodiment to a 300 mV signal. However, the gain of second stage amplifier 155 may also be on the order of 10 to 100. As was the case with first stage amplifier 115, a programmable gain amplifier may be used for second stage amplifier 155. Alternatively, as described above, the unused (fourth) op-amp in the filter 150 implementation shown in FIG. 6 may be used for second stage amplifier 155.

Analog to digital converter 160 converts the analog waveform output by second stage amplifier 155 into a digital representation that can then be processed by one or more algorithms, as described more fully herein, to determine heart related parameters, such as heart rate, therefrom. Analog to digital converter 160 may be implemented using a 12 bit analog to digital converter with a 3 V reference at 32-256 samples per second. Such a device is integrated into the Texas Instruments MSP430F135 processor. Analog to digital converter 160 is connected to central processing unit 165, which reads the converted digital signal and performs one of the following functions: (i) it stores the raw digital signal to memory, such as flash or SRAM, for subsequent analysis; (ii) it stores a number of raw digital signals to memory and subsequently transmits them, wired or wirelessly, to a remote computer for analysis as described herein and/or display, such as display in real time; or (iii) it processes the raw digital signals using algorithms described herein provided on central processing unit 165 to determine heart related parameters, such as the timing and various sizes of heart beats, heart rate, and/or beat-to-beat variability. With respect to this last function, central processing unit 165 may, once heart beats and/or heart rate has been determined, perform a variety of tasks such as blink an LED for each beat or store heart rate information to memory. Optionally, central processing unit may provide operational control or, at a minimum, selection of an audio player device 166. As will be apparent to those skilled in the art, audio player 166 is of the type which either stores and plays or plays separately stored audio media. The device may control the output of audio player 166, as described in more detail below, or may merely furnish a user interface to permit control of audio player 166 by the wearer.

These functions can also be performed independently in sequence. For example, the data can be stored in real time in a data storage medium while being simultaneously analyzed and output. Subsequent processes can allow the system to retrieve earlier stored data and attempt to retrieve different information utilizing alternative algorithmic techniques or filters. Additionally, data from different points in the filtration process, described above, can be simultaneously stored and compared or individually analyzed to detect signal information which is lost at certain points in the process.

Figure 7:
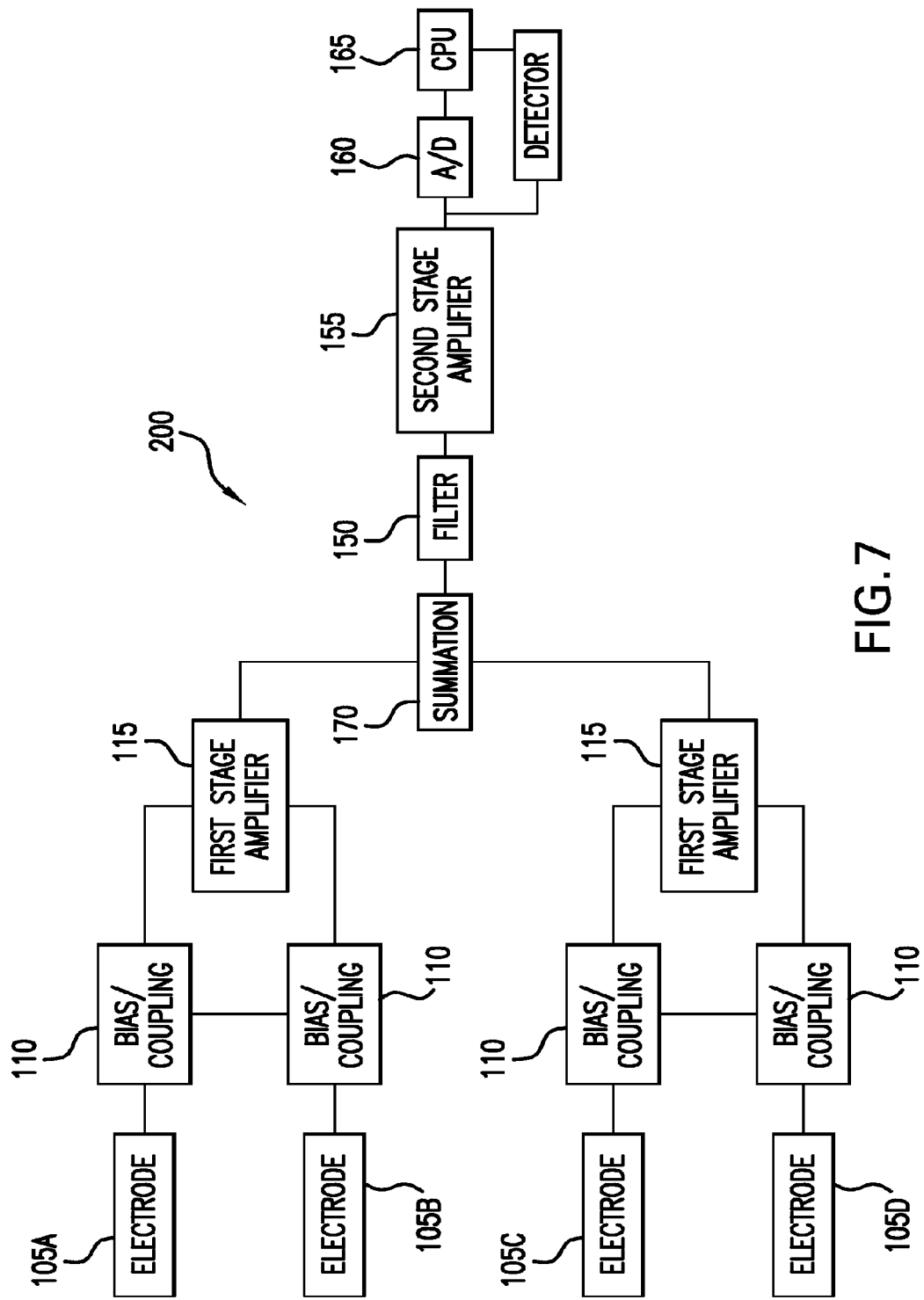
FIG. 7 is a block diagram of a circuit for detecting an ECG signal from according to an alternate embodiment of the present invention.

Referring to FIG. 7, alternate circuit 200 for measuring an ECG signal is shown in which an array of multiple electrodes 105, for example four electrodes 105A through 105D, are used. The electrodes 105 in this embodiment are grouped in pairs and, as was the case with circuit 100 shown in FIG. 4, one electrode of each pair is placed in a location that is related to the electropotential of the right side of the ECG signal and the other electrode in each pair is placed in a location that is related to the electropotential of the left side of the ECG signal. The first electrodes in each pair may be placed in locations close to one another to attempt to get a good signal form a particular general location, or may be placed in locations removed from one another, as illustrated in the particular embodiments described with more detail below, to pick up signals from different locations. The second electrodes in each pair may be similarly placed. Each pair of electrodes 105 is connected to bias/coupling network 110 as described above, and the output is connected to a first stage amplifier 115 as described above. In the embodiment shown in FIGS. 7, 8A-D and 8F, the output of each first stage amplifier 115 is fed into summation circuit 170, which for example may be a resistor network Summation circuit 170 adds the outputs of the first stage amplifiers 115 together. The summed signal is then passed through filter 150, second stage amplifier 155, and to analog to digital converter 160 and central processing unit 165 as described above.

It is to be specifically noted that the circuitry may be implemented in a minimal cost and component embodiment, which may be most applicable to a disposable application of the device. In this embodiment, the apparatus is not provided with a processor, only electrically separated electrodes for picking up a voltage difference, a gating mechanism for differentially passing current associated with voltage spikes, such as QRS signals and a mechanism for displaying characteristics of the passed through current. This apparatus may be powered by motion, battery, or solar power. Another option is to power the apparatus directly from the voltage potentials being measured. The display mechanism may be chemical, LCD or other low power consumption device. The voltage spikes charge up a capacitor with a very slow trickle release; a simple LED display shows off the charge in the capacitor. In another embodiment, a simple analog display is powered by the battery. The simple apparatus utilizes digital processing but no explicit processor; instead a simple collection of gates, threshold circuitry and accumulator circuitry, as would be apparent to one skilled in the art, based upon the descriptions above, controls the necessary preprogrammed logic.

The implementation shown in FIGS. 7 and 8A-F, which utilize an array of electrodes 105, is particularly useful and advantageous due to the fact that the signals detected by electrodes 105 can at times be saturated by muscle activity of the body, such as muscle activity in the arm in an embodiment where electrodes 105 are placed on locations of the arm. The heart beat related portion of the signals detected by electrodes 105 are coherent, meaning highly correlated, while the muscle activity noise portions of the signals tend to be incoherent, meaning not correlated. Thus, because of this coherent/incoherent nature of the different portions of signals, when the signals generated by electrodes 105 are summed, subtracted, averaged, multiplied or the like, by summation circuit 170, the heart beat related components will add to one another thereby producing better heart beat spikes having a higher signal to noise ratio, while the muscle noise related components will tend to wash or cancel one another out because the "hills" and "valleys" in those signals tend to be off phase from one another. The result is a stronger heart beat related signal with less muscle related noise.

Figure 8A:
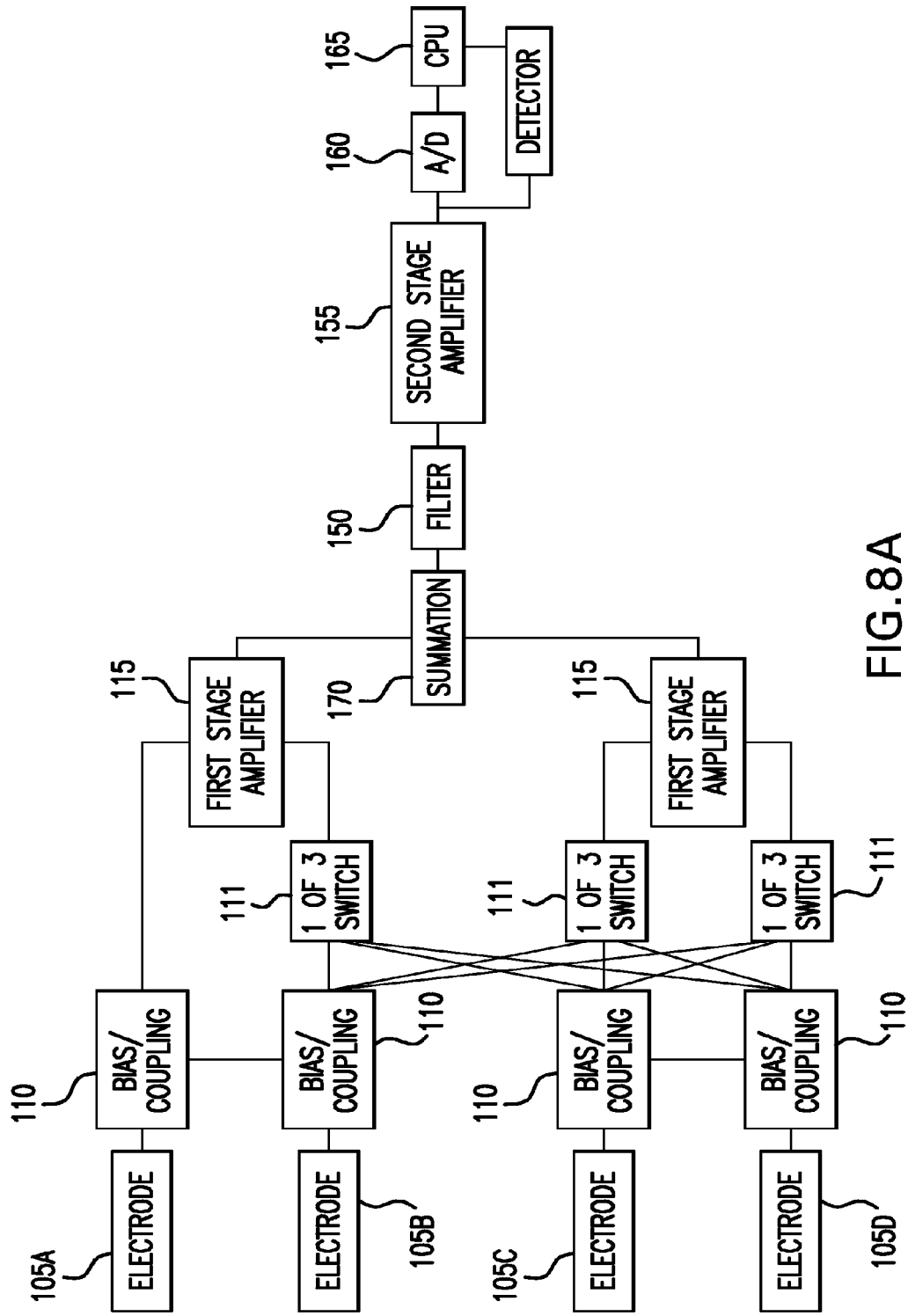
Figure 8B:
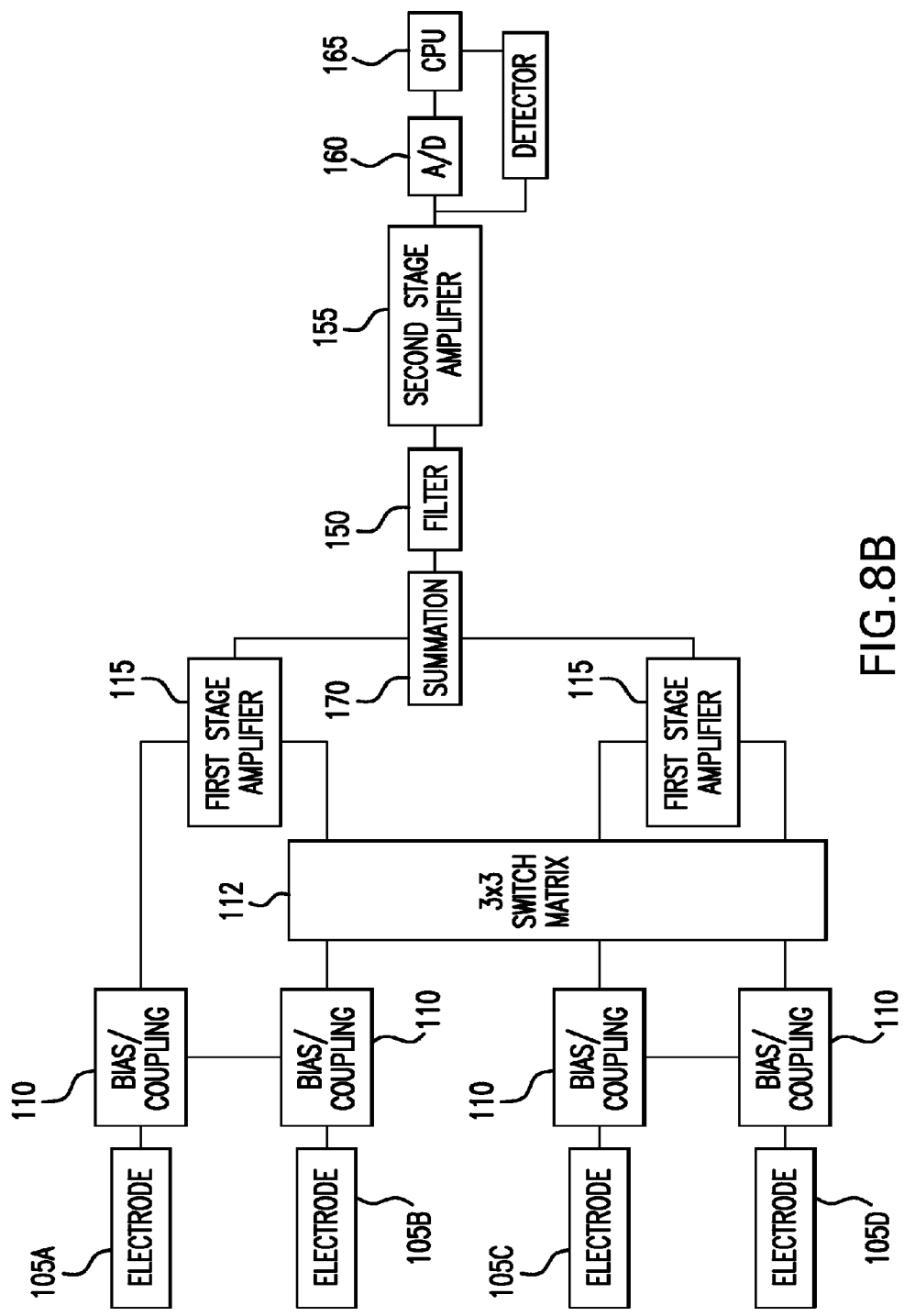
Figure 8C:
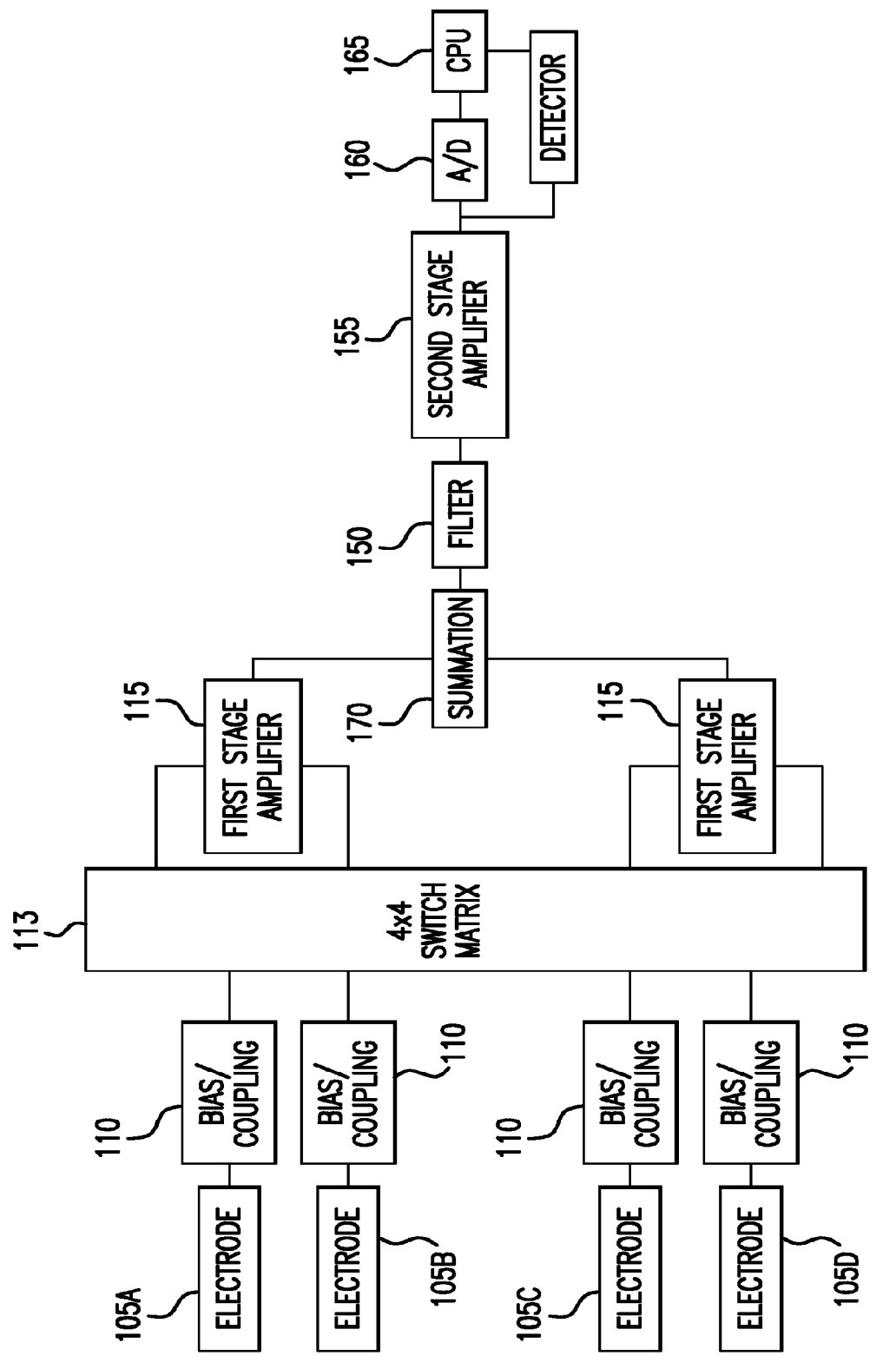
Figure 8D:
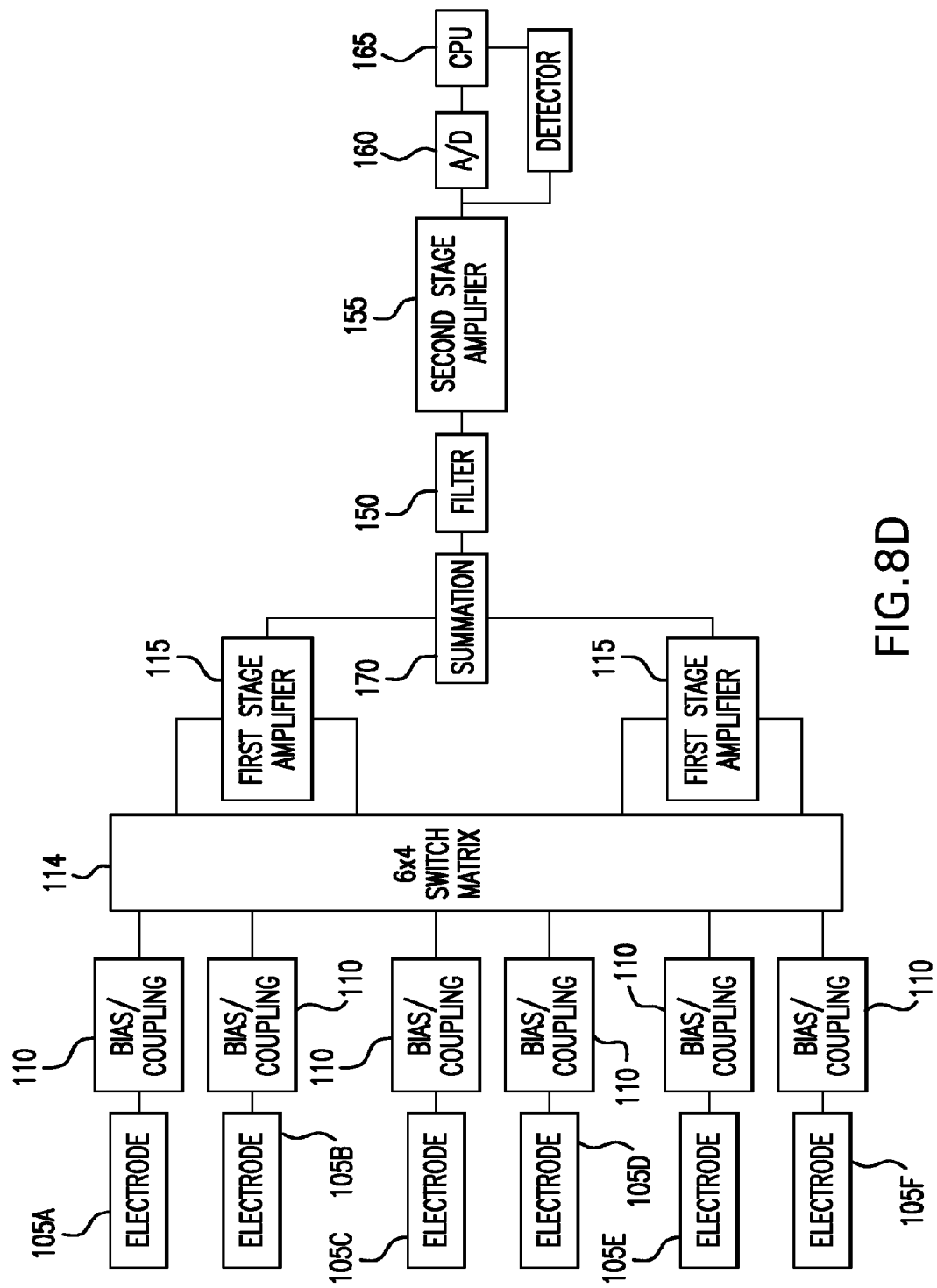
Figure 8F:
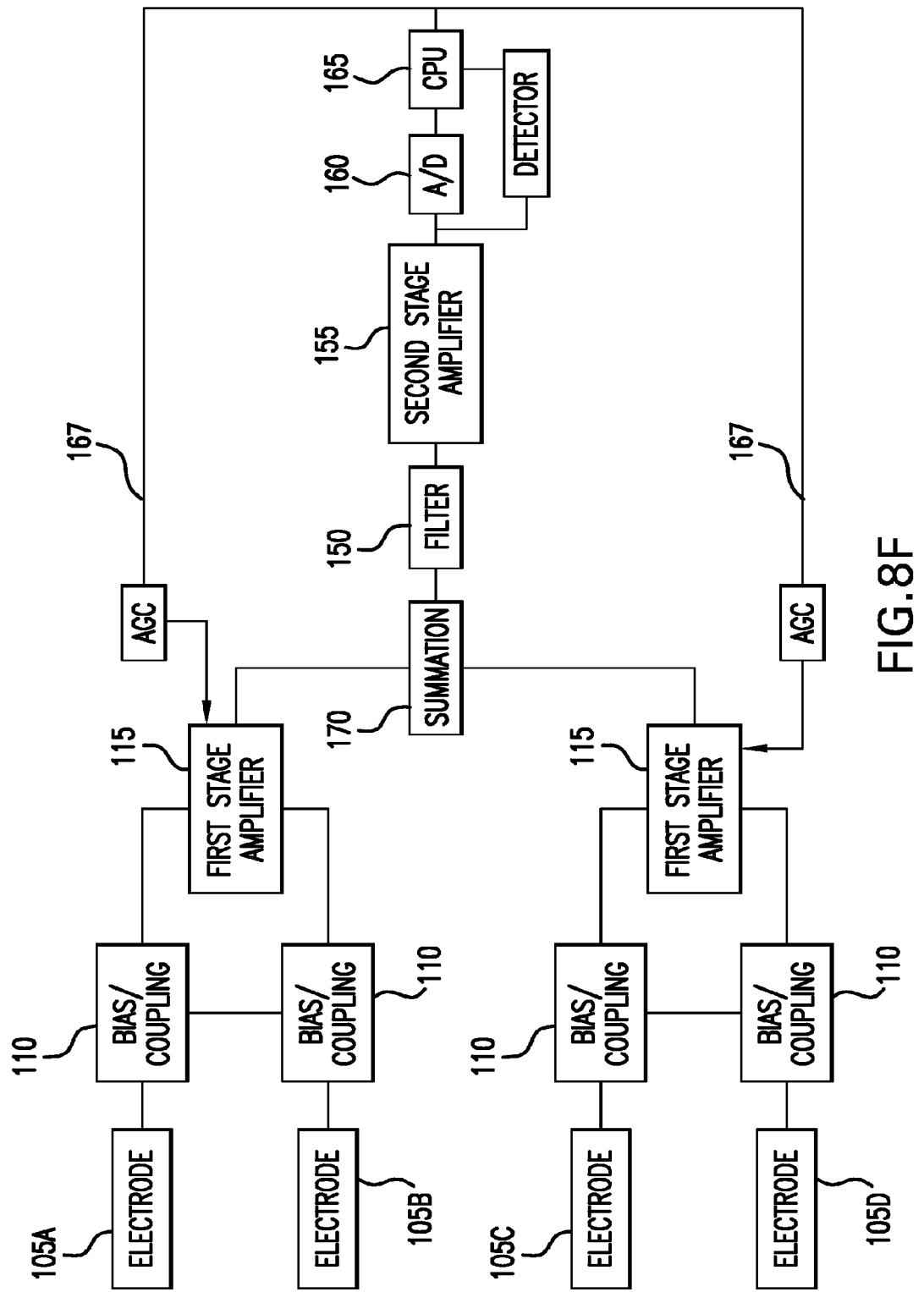

FIGS. 8A through 8F illustrate alternative embodiments of the system incorporating multiple electrodes shown in FIG. 7. FIG. 8A illustrates, three electrodes 105B-F interchangeably routed by switches 111 to any of the first stage differential amplifier 115 inputs to allow various combinations of electrode subtractions and additions. This arrangement assumes that one electrode will always be treated in the positive sense. FIG. 8B illustrates an arrangement similar to FIG. 8A, however, a 3×3 switch matrix 112 is utilized rather than the discrete switches shown in FIG. 8A. FIG. 8C illustrates a 4×4 switch matrix 113, which allows full control of electrode pair addition/subtraction and is the most simple conceptually. In some embodiments, the functionality of the switch matrix 113 may be reduced to permit only certain pairings in order to obtain a cleaner signal. FIG. 8D illustrates a 6×4 switch matrix 114, which allows full control of electrode pair addition/subtraction and permits the selection of two pairs from the full suite of electrodes. FIG. 8D includes additional electrodes 105E-F to illustrate the selectability of three full pairs of such electrodes. As with the embodiment shown in FIG. 8C, the functionality of the switch may be reduced to permit only certain pairings. This could conceptually be expanded to as many electrodes as desired. FIG. 8E illustrates an embodiment that provides electrode shielding, and the individual pairs of electrodes can be sampled and then summed and/or subtracted during subsequent analysis, the strongest pair may simply be chosen or the average may be taken of an array of signals. This arrangement can also require 50-60 Hz filtering and higher first stage amplifier gains to keep the signal to noise ratio high. FIG. 8F illustrates an embodiment in which the CPU controls the gain of the first stage amplifier through AGC circuits 167, enabling the system to adjust for poor electrode placement or subjects with weaker ECG signals. These embodiments permit the selection of the strongest pair or best signal from of a multiplicity of pairs of electrodes for analysis. This can be accomplished according to several methodologies in addition to mere signal strength. These include the analysis of all the pairs and combination of the signals or calculation of an average of all of the signals or the identification of the most distorted signal, considering muscle artifact noise or the like, and utilizing it as a filter signal to be subtracted from the identified best signal.

There are multiple sources of noise that can affect the amplified signal that is input into analog to digital converter 160 shown in FIGS. 4, 7 and 8A-F. For example, as described above, mains hum and DC wander noise can effect the signal. In the embodiments shown in FIGS. 4, 7 and 8A-F, this noise is removed using filter 150. In an alternate embodiment, rather than using a hardware solution like filter 150 to remove the 50/60 Hz mains hum and/or DC wander noise from the voltage potential difference signal received from electrodes 105, some or all of this noise can be filtered out of the signal, after being digitized by analog to digital converter 160, using known software techniques implemented in software residing either on CPU 165 forming a part of a body monitoring device or on a separate computer that receives the digitized signal. In this embodiment, filter 150 would be eliminated and only a single amplifier having a gain on the order of 500 to 2500 such as first stage amplifier 115 would be used in circuit 100 or 200. A two stage amplifier may also be utilized, having first stage gain of 50-500 and a second stage gain of 10-50. These steps (in either the hardware or software implementations), in effect remove components of the signal having frequencies that are considered to be too high or too low to constitute a heart related signal, with a typical ECG signal having a frequency in the range of 0.5-4 Hz.

The system is specifically designed to minimize the processing time delays and interruptions created by noise being processed and subtracted or filtered from the primary signal. As noise is processed and consuming processor resources, data must be stored and processed at a later time. It is important to return as quickly as possible to contemporaneous monitoring so as to avoid the build up of a backlog of data. The system utilizes a plurality of measurement techniques, such as described above to quickly identify and extract the primary signal and rapidly return to real time monitoring. Most particularly, the circuitry is designed to minimize DC wander within three beats of the heart.

In addition, another source of noise that may affect the signal input into analog to digital converter 160 is muscle noise caused by the electrical activity of muscles. Electromyography, or EMG, is a measurement of the electrical activity within muscle fibers, which is generally measured actively, but could also be measured passively, according to the method of subtraction or filtering of the most distorted signal described above, because it is affected most by muscle artifact and/or has very little if not any signal relating to the heart related electrical activity. While a subject is in motion, electrodes 105 for measuring ECG may also simultaneously pick up and measure EMG signals. Such contemporaneously measured EMG signals are noise to the ECG signal. Thus, according to an aspect of the present invention, ECG signal measurement can be improved by using separate electrodes to specifically measure an EMG signal, preferably from body locations that have a minimal or difficult to detect ECG signal. This separately measured EMG signal may then be used to reduce or eliminate EMG noise present in the separately and contemporaneously measured ECG signal using various signal processing techniques. In many cases, the EMG signal's amplitude may so overwhelm that ECG signal that either filtering or utilizing the above-described method may not result in a usable ECG signal. In these events, the use of a non-electrode sensor could be utilized in conjunction with electrodes in order to detect the relatively quiet ECG signal. This sensor may even replace the beat detection if it detected ECG peaks when the primary electrical signal clips, gets oversaturated or overwhelmed by the EMG signal. An example sensor is a micro-Doppler system, either as a single pick-up or an array, designed to pick up the mechanical rushing of blood or the like, past the Doppler signal, creating a pulse wave in which the peak could be recognized and timed as a beat. This embodiment could be tuned to a specific location or utilize an array of different sensors tuned to different depths in order to optimize and locate the best signal for each user. This array could also be utilized, through monitoring of different signals and signal strength, to locate the device at the best position on the arm through well known audible or visual feedback mechanisms. The device could also be tuned to certain individual characteristics detected over an introductory period of evaluation or tuned dynamically over a period of time. Under certain high noise circumstances, the mechanical signal might be substituted for the electrical ECG signal as part of the calculations. In order to make the mechanical and electrical wave align, timing and phase shift differences would have to be calculated and factored into the peak or beat recognition algorithm. This system could be also utilized for detection and measurement of pulse transit time, or PTT, of the wearer, as described more fully herein, allowing relative and/or absolute measurement of blood pressure could be derived or calculated.

Pulse transit time, or PTT, is the time that it takes a pulse pressure waveform created by a heart beat to propagate through a given length of the arterial system. The pulse pressure waveform results from the ejection of blood from the left ventricle of the heart and moves through the arterial system with a velocity that is greater than the forward movement of the blood itself, with the waveform traveling along the arteries ahead of the blood. PTT can be determined by measuring the time delay between the peak of a heart beat, detected using the R-wave of an ECG signal and the arrival of the corresponding pressure wave at a location on the body such as the finger, arm, or toe, measured by a device such as a pulse oximeter or other type of pressure detector. As blood pressure increases, more pressure is exerted by the arterial walls and the velocity of the pulse pressure waveform increases. The velocity of the pulse pressure waveform depends on the tension of the arterial walls; The more rigid or contracted the arterial wall, the faster the wave velocity. As a result, for a fixed arterial vessel distance, as PTT increases and pulse pressure waveform velocity decreases, blood pressure decreases, and as PTT decreases and pulse pressure waveform velocity increases, blood pressure increases. Thus, PTT can be measured and used to indicate sudden changes in real-time blood pressure.

In one embodiment, the same armband device includes the ability to detect the ECG signal and in conjunction with a micro Doppler array against the body, together create the PTT measurement. An aspect of the present invention relates to the measurement and monitoring of PTT. Specifically, the time of a heart beat peak can be determined using an ECG signal using electrodes 105 as described herein. The time of the arrival of the corresponding pressure wave at a given location on the body can be measured using any one of a number of pressure sensors. Such pressure sensors may include, but are not limited to, pulse oximeters, Doppler arrays, single piezoelectric sensors, acoustic piezoelectric sensors, fiber optic acoustic sensors, blood volume pressure or BVP sensors, optical plethysmographic sensors, micropower impulse radar detectors, and seismophones. According to a preferred embodiment of the present invention, PTT is measured and monitored to indicate changes in blood pressure using armband body monitoring device 300 that is provided with one or more of the pressure sensors described above. Thus, in this embodiment, PTT is measured in a single device that obtains an ECG signal from the upper arm and that measures the arrival of the pulse pressure waveform at a location on the upper arm. Alternatively, the pressure sensor may be located separately from armband body monitoring device 300 at a different location, such as the finger or wrist, with the information relating to the arrival time being transmitted to armband body monitoring device 300 for calculation. This calculation may also be made at the finger product, or other third product, or shared between any combination of the above. Communication between each device can be provided in a wired or wireless embodiment, or transmitted through the skin of the wearer, as is well known to those skilled in the art.

An alternative embodiment includes the incorporation of third party devices, not necessary worn on the body, collect additional data to be utilized in conjunction with heart parameter data or in support thereof. Examples include portable blood analyzers, glucose monitors, weight scales, blood pressure cuffs, pulse oximeters, CPAP machines, portable oxygen machines, home thermostats, treadmills, cell phones and GPS locators. The system could collect from, or in the case of a treadmill or CPAP, control these devices, and collect data to be integrated into the streams for real time or future derivations of new parameters. An example of this is a pulse oximeter on the user's finger could help measure PTT and therefore serve a surrogate reading for blood pressure. Additionally, a user could utilize one of these other devices to establish baseline readings in order to calibrate the device.

In one specific embodiment, electrodes 105 may be placed on the deltoid muscle and the triceps muscle of the left arm in order to measure an ECG signal, which will likely contain muscle related noise, and separate electrodes 105 may be placed one each on the triceps muscle or one on the triceps muscle and one on the brachialis muscle for collecting an EMG signal having little or no ECG component, according to at least one of the several embodiments of the device more fully described below. This EMG signal may then be used to process and refine the measured ECG signal to remove the EMG noise as described herein. An example of such a configuration is armband body monitoring device 300 described below in connection with the specific alternative embodiments of the device, and more specifically FIG. 15, in which electrodes 105A and 105B would measure an ECG signal likely containing muscle related noise, and electrodes 105C and 105D measure an EMG signal having little or no ECG component.

Although muscle noise can be reduced using separate EMG sensors as just described, it has been found that this noise, to a degree, often ends up remaining in the signal input into analog to digital converter 160 despite efforts to eliminate or reduce such noise. The amplitude of actual heart beat spikes, which comprise the QRS wave portion of the ECG signal, in the collected signal may vary throughout the signal, and the remaining muscle noise may obscure a heart beat spike in the signal or may itself look like one or more heart beat spikes. Thus, an aspect of the present invention relates to various processes and techniques, implemented in software, for identifying and reducing noise that is present in the digital signal output by analog to digital converter 160 and identifying heart beats and heart beat patterns from that signal. In addition, there may be portions of the signal that, despite processing efforts, contain too much noise and therefore no discernable heart related signal. A further aspect of the present invention relates to process and techniques for dealing with such portions and interpolating the data necessary to provide continuous and accurate output.

Figure 9:
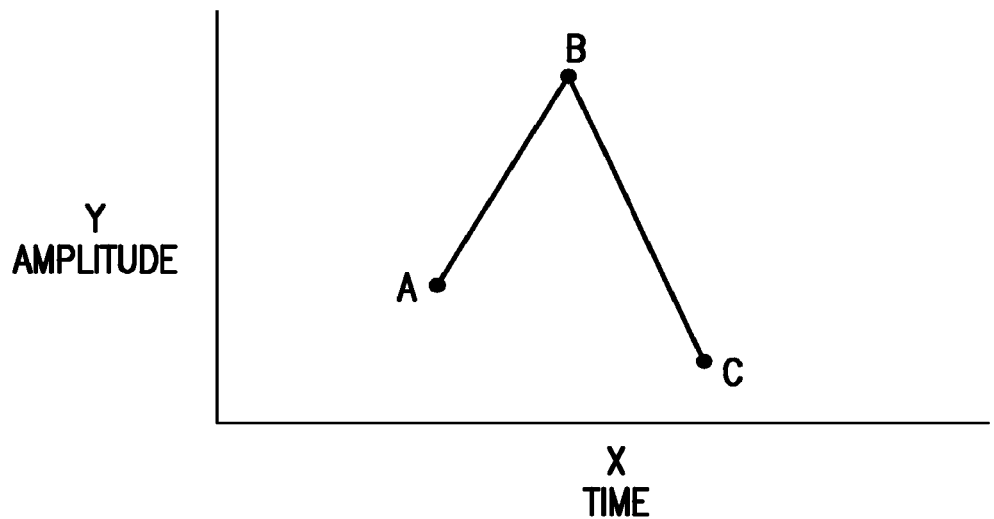
FIG. 9 is a diagram of a typical peak forming a part of the signal generated according to the present invention.

According to a one embodiment of the present invention, the signal that is output by analog to digital converter 160 may first undergo one or more noise reduction steps using software residing on either CPU 165 or on a separate computer to which the signal has been sent. For example, in one possible noise reduction implementation, the signal is first processed to identify each peak in the signal, meaning an increasing amplitude portion followed by a maximum amplitude portion followed by a decreasing amplitude portion. An example of such a peak is shown in FIG. 9 and includes points A, B and C wherein the X axis is time and the Y axis is signal strength or amplitude. For each identified peak, the height of the peak (in units of amplitude) and the width of the peak (in units of time) are then calculated. Preferably, the height for each peak is determined as follows: min (BY–AY, BY–CY), and the width for each peak is determined as follows: (CX–AX). In addition, a standard height and width profile of a heart beat spike, comprising the QRS wave, is established and stored, and identified peaks present in the signal that are outside of the stored profile are eliminated, meaning that those portions of the signal are marked to be ignored by further processing steps because they constitute noise. In a preferred embodiment, the standard height in the stored profile is approximately 400 points when a 128 Hz analog to digital sampling rate is used and a 12-bit encoding of the signal is used and the standard width in the stored profile is approximately 3 to 15 points when a 128 Hz analog to digital sampling rate is used and a 12-bit encoding of the signal is used. In one particular embodiment, the profile may constitute an adaptive height and/or width that is stored and used for identifying spikes in the signal that are to be eliminated, such as a height and/or width based on a percentage of the moving average of previous measurements. In addition, peaks in the signal that hit the maximum and minimum value rails output by analog to digital converter 160 may be eliminated as well. Peaks may also be eliminated from the signal if they would indicate an unlikely heart rate given the surrounding signal context, i.e., other peaks in close proximity that would result in a calculated heart rate that is above a likely maximum value. Finally, noise can be removed based on using additional sensors preferably provided with the body monitoring device that implements circuit 100 shown in FIG. 4 or circuit 200 shown in FIG. 7, including, but not limited to, accelerometers or other motion detecting sensors for detecting either motion or tension, audio sensors, or using time-spectrum signature of muscle noise.

Figure 7B:
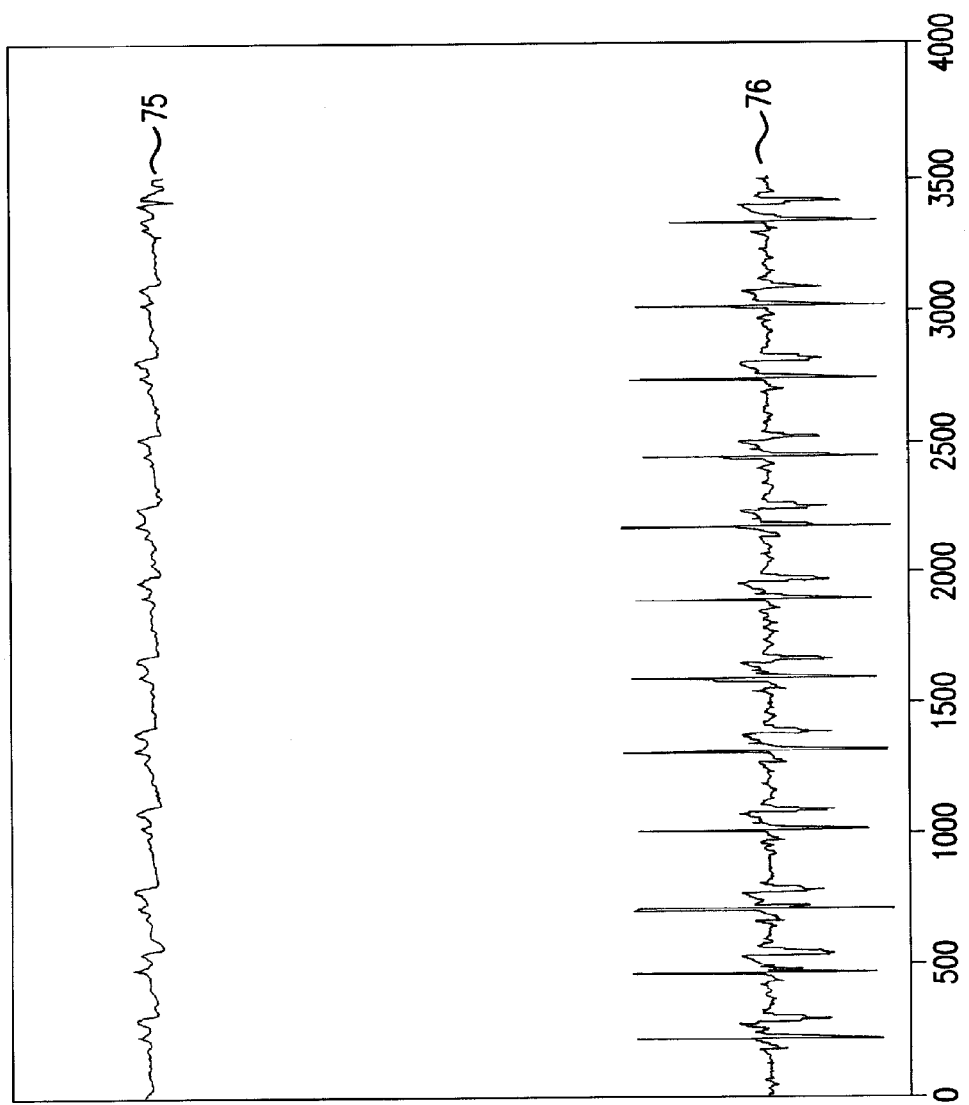
Figure 7C:
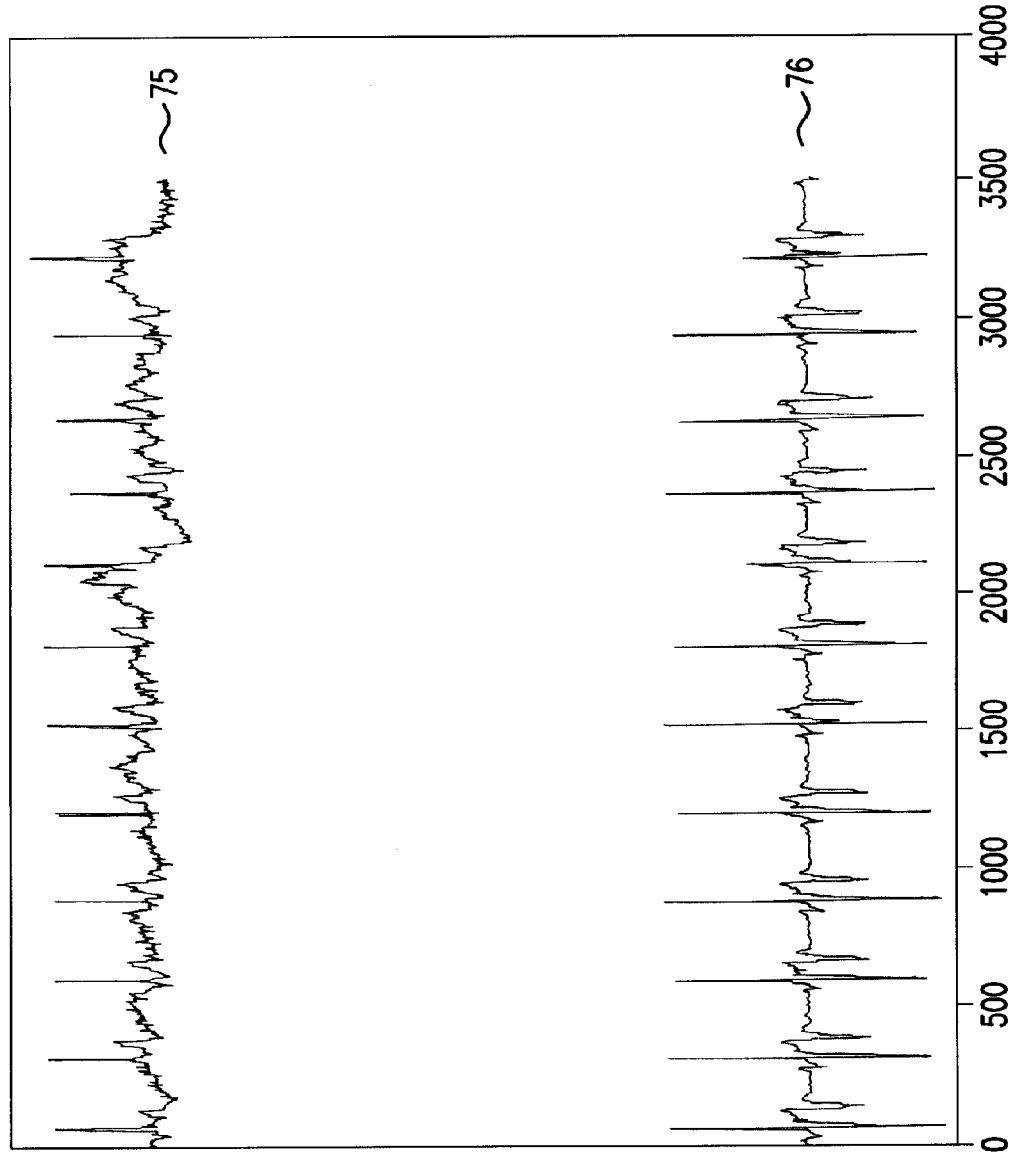
Figure 7D:
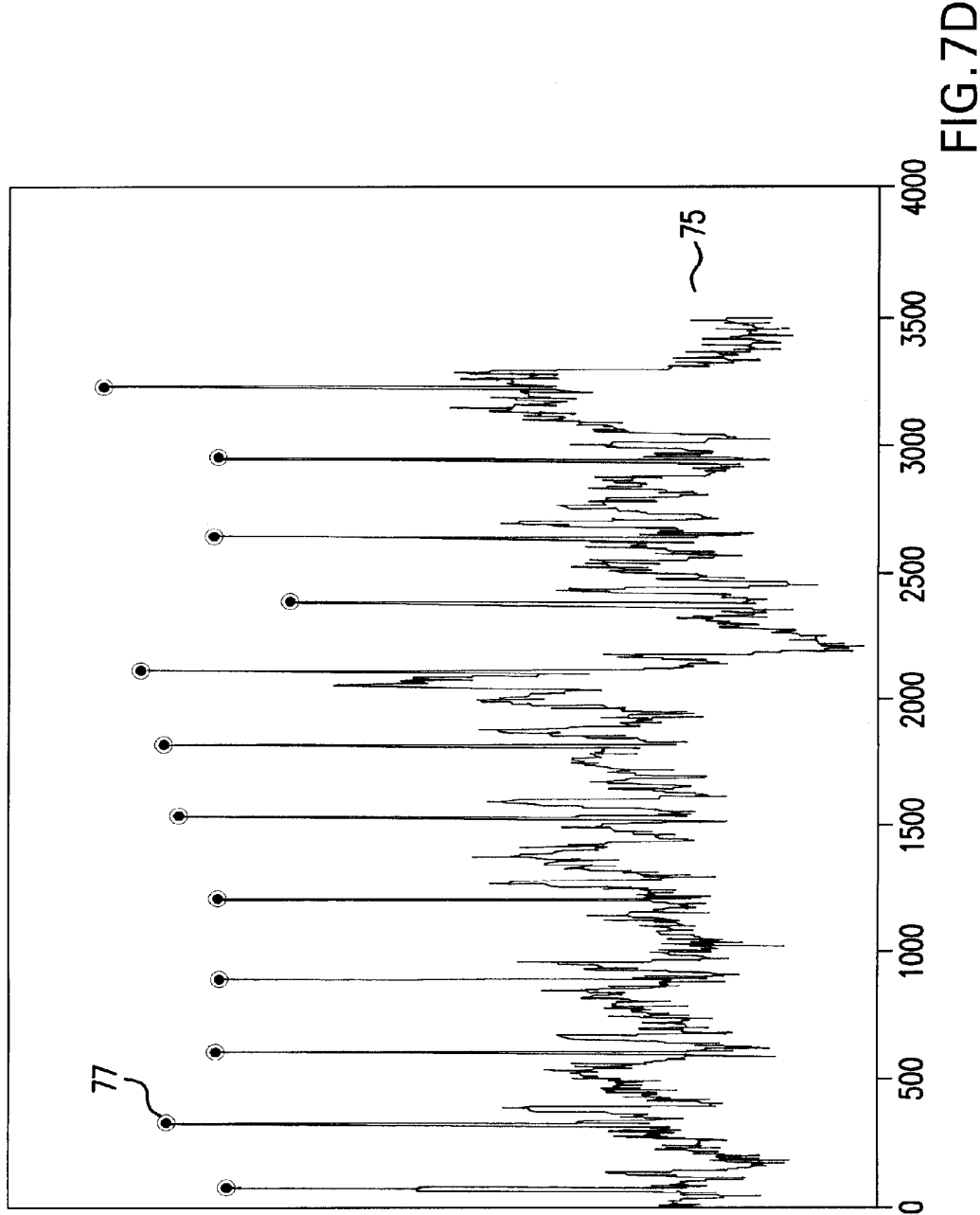

FIGS. 7A through 7D illustrate the progressive steps of obtaining and extracting the ECG data and heart beats from the detected signal. Referring now to FIG. 7A, the detected signal 75 is illustrated in conjunction with a simultaneously recorded reference signal 76 of the same heartbeat by a conventional ECG monitor. The detected signal 75 is essentially without notable features and the entire heart related signal is masked by noise. Most prevalent in FIG. 7A is 60 Hz mains hum 77, which is present in the reference signal as well. FIG. 7B illustrates the same two signals after filtering with a 30 Hz filter. The reference signal 76 reveals an essentially intact and unobscured ECG signal. The detected signal reveals some periodic features, but with minimal amplitude or signal strength. FIG. 7C illustrates the modification of the detected signal 75 after amplification. Reference signal 76 has not been modified. FIG. 7D illustrates only detected signal 75 after additional signal processing and identification of the peaks 77, as described more fully herein.

Figure 7E:
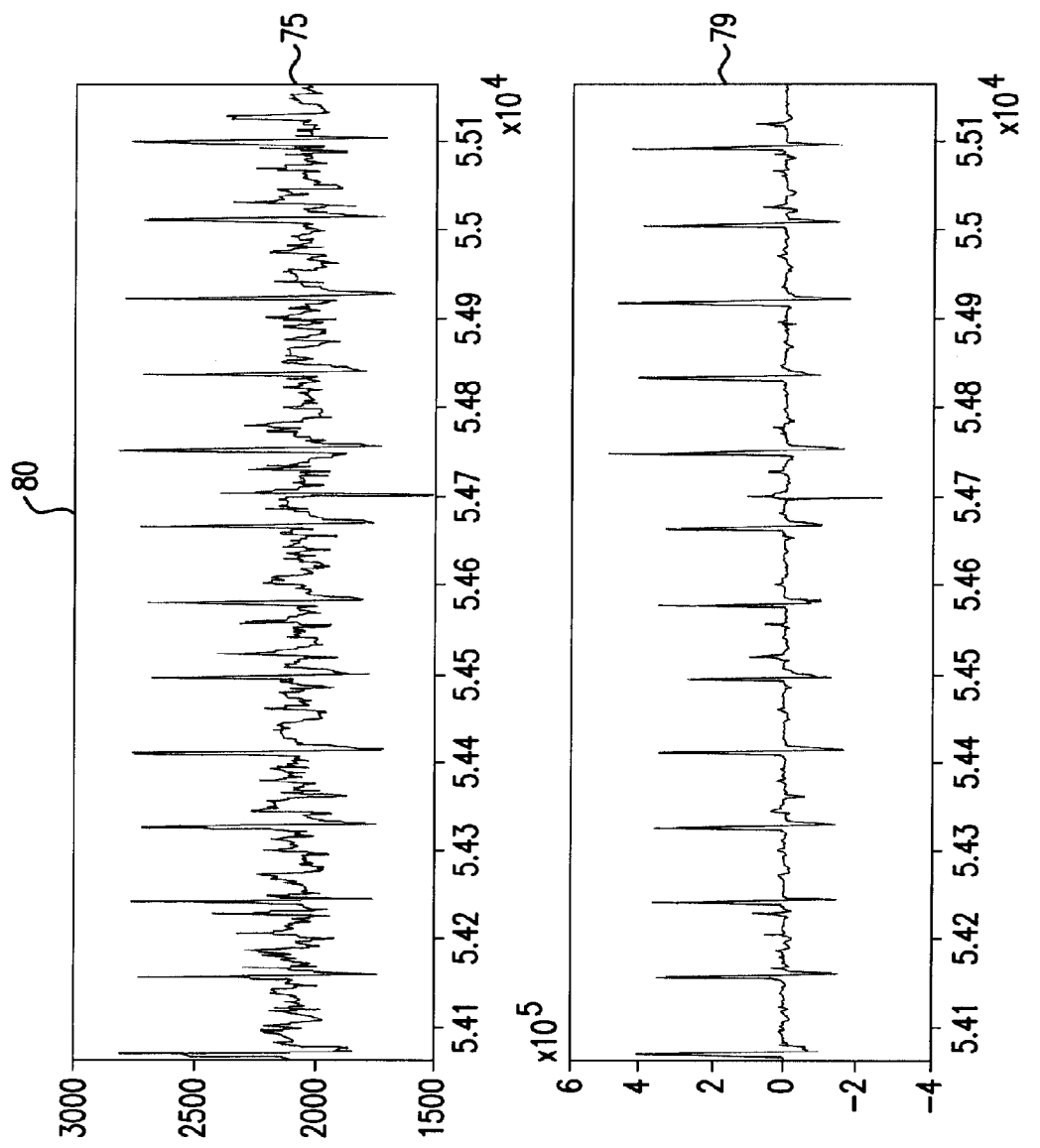

Another method for eliminating noise is that of filtering the signal in software residing either on either CPU 165 or on a separate computer to which the signal has been sent. In the preferred embodiment, this filtering consists of a non-linear filter designed to accentuate differences between noise and heartbeats. FIG. 7E shows the results of applying this filter. Detected signal 75 is illustrated in box 80 in an unfiltered state and in box 79 after filtering.

While these noise reduction steps are likely to remove a significant amount of noise from the signal received from analog to digital converter 160, it is likely that, notwithstanding this processing, there will still be noise remaining in the signal. This noise makes the task of identifying actual heart beat spikes from the signal for purposes of further processing, such as calculating a heart rate or other heart related parameters, difficult. Thus, a further aspect of the present invention relates to various processes and techniques, again implemented in software residing on either CPU 165 or a separate computer, for identifying heart beat spikes from the signal notwithstanding any remaining noise. As will be appreciated, these processes and techniques, while preferably being performed after one or more of the noise reduction steps described above, may also be performed with any prior noise reduction steps having been performed.

As is well-known in the prior art, the Pan-Tompkins method uses a set of signal processing frequency filters to first pass only the signal that is likely to be generated by heart beats, then proceeds to differentiate, square and perform a moving window integration on the passed signal. The Pan-Tompkins method is described in Pan, J. & Tompkins, W. J., "A Real-time QRS Detection Algorithm," IEEE Transactions on Biomedical Engineering, 32, 230-236 (1985), the disclosure of which is incorporated herein by reference.

According to this aspect of the invention, areas in the signal output by analog to digital converter 160 (with or without noise reduction as described above) having excessive noise, i.e., too much noise to practically detect acceptable heart beat spikes from the signal, are first identified and marked to be ignored in the processing. This may be done by, for example, identifying areas in the signal having more than a predetermined number of rail hits or areas in the signal within a predetermined time window, e.g., ¼ of a second, of two or more rail hits. Next, the remaining areas, i.e., those not eliminated due to too much noise being present, referred to herein as the non-noise signal, are processed to identify acceptable heart beat spikes for use in calculating various heart parameters such as heart rate.

In one embodiment of the present invention, acceptable heart beat spikes are identified in the non-noise signal by first identifying and then calculating the height and width of each peak in the non-noise signal as described above. Next, the width of each peak is compared to a predetermined acceptable range of widths, and if the width is determined to be within the acceptable range, the height of the peak is compared to an adaptive threshold height equal to 0.75 of the moving average of the height of the previous peaks. Preferably, the acceptable range of widths is 3 to 15 points when a 128 Hz analog to digital sampling rate is used, and represents a typical range of widths of a QRS portion of an ECG signal. Next, if the width of the current peak is within the acceptable range and if the height of the peak is greater than the adaptive threshold, then that peak is considered a candidate to be an acceptable peak for further processing. Peaks not meeting these requirements are ignored. Next, for candidate acceptable peaks within a predetermined timeframe of one another, preferably 3/16 of a second of one another, the heights of the peaks are compared to one another and the lower peaks in that time frame are ignored. If there is only one candidate acceptable peak within the timeframe, then that peak is considered a candidate acceptable peak. At this point, a number of candidate acceptable peaks will have been identified. Next, for each identified candidate acceptable peak, the area between that peak and the last, being that immediately previous in time, candidate acceptable peak is examined for any other signal peaks having a height that is greater than 0.75 of the height of the current candidate acceptable peak. If there are more than a predetermined number, preferably 2, such peaks identified, then the current candidate acceptable peak is invalidated and ignored for further processing. In addition, if there are any hits of the rail as described above between the last candidate acceptable peak and the current candidate acceptable peak, then the current candidate acceptable peak is invalidated and ignored for further processing. When these steps are completed, a number of acceptable peaks will have been identified in the signal, each one being deemed an acceptable heart beat spike that may be used to calculate heart related parameters therefrom, including, but not limited to, heart rate.

Figure 10:
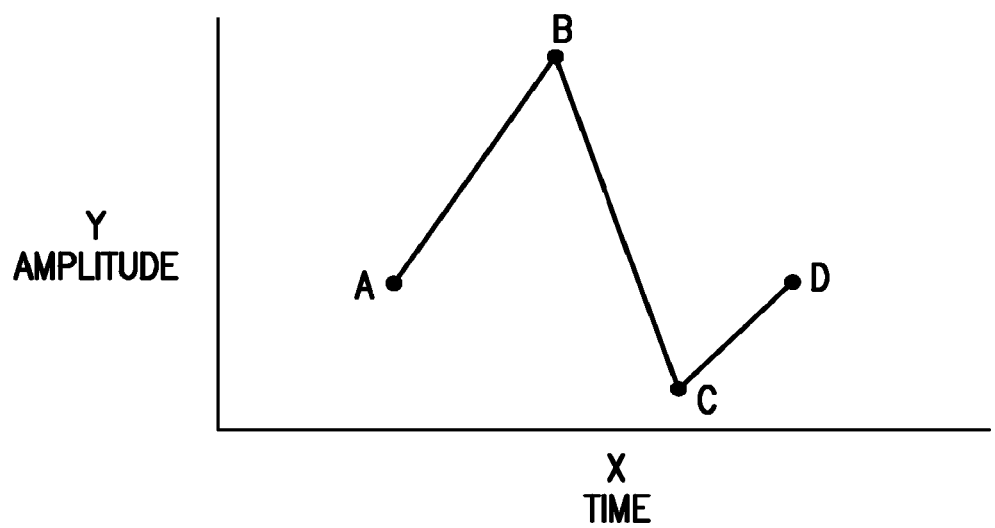
FIG. 10 is a diagram of a typical up-down-up sequence forming a part of the signal generated according to the present invention.

According to an alternate embodiment for identifying acceptable heart beat spikes, each up-down-up sequence, a possible QRST sequence, in the non-noise signal is first identified. As used herein, an up-down-up sequence refers to a sequence on the non-noise signal having an increasing amplitude portion followed by a maximum amplitude portion followed by a decreasing amplitude portion followed by a minimum amplitude portion followed by an increasing amplitude portion. An example of such up-down-up sequence is shown in FIG. 10 and includes points A, B, C, and D wherein the X axis is time and the Y axis is signal strength or amplitude. After each up-down-up sequence is identified, the height, in terms of amplitude, and the width, in terms of time, of each up-down-up sequence is calculated. Preferably, the height for each up-down-up sequence is determined as follows: (BY−

AY)+(BY−CY)+(DY−CY), and the width for each peak is determined as follows: (DX−AX).

Next, the height of each up-down-up sequence is compared to a predetermined threshold value, preferably an adaptive threshold such as some percentage, e.g., 75%, of the moving average of previous heights, and the width of each up-down-up sequence is compared to a predetermined threshold value range, preferably equal to 4 to 20 points when a 128 Hz analog to digital sampling rate is used, which represents a typical range of widths of a QRST sequence of an ECG signal. If the height is greater than the threshold and the width is within than the predetermined threshold value range, then that up-down-up sequence is considered to be a candidate acceptable QRST sequence. Next, for each identified candidate acceptable QRST sequence in the non-noise signal, a surrounding time period window having a predetermined length, preferably 3/16 of a second, is examined and the height of the current candidate acceptable QRST sequence in the time period window is compared to all other identified candidate acceptable QRST sequences in the time period window. The candidate acceptable QRST sequence having the largest height in the time period window, which may or may not be the current candidate acceptable QRST sequence, is validated, and the other candidate acceptable QRST sequences in the time period window, which may include the current candidate acceptable QRST sequence, are invalidated and ignored for further processing. Once this step has been completed, a number of acceptable QRST sequences will have been identified in the non-noise signal. Next, for each acceptable QRST sequence that has been identified, the distance, in terms of time, to the immediately previous in time acceptable QRST sequence and the immediately next in time QRST sequence are measured. Each distance is preferably measured from the R point of one sequence to R point of the other sequence. The R point in each acceptable QRST sequence corresponds to the point B shown in FIG. 10, the highest amplitude point. In addition, two standard deviations are calculated for each acceptable QRST sequence. The first standard deviation is the standard deviation of the amplitude of all of the sampled points between the T point, which corresponds to point D shown in FIG. 10, of the current acceptable QRST sequence and the Q point, which corresponds to point A shown in FIG. 10, of the immediately next in time acceptable QRST sequence. The other standard deviation is the standard deviation of the amplitude of all of the sampled points between the Q point, which corresponds to point A shown in FIG. 10, of the current acceptable QRST sequence to the T point, which corresponds to point D shown in FIG. 10, of the immediately previous in time QRST sequence. Next, the two measured distances, the two standard deviations and the calculated height and width of each acceptable QRST sequence are input into a simple heart beat classifier, which decides whether the acceptable QRST sequence and the surrounding area is a qualifying heart beat or is too noisy. For example, the heart beat classifier may be a decision tree that has been trained using previously obtained and labeled heart beat data. Alternatively, the heart beat classifier may be any known classifier mechanism, including, but not limited to, decision trees, artificial neural networks, support vector machines, Bayesian belief networks, naïve Bayes and decision lists.

Those sequences that are determined to be too noisy are ignored. Thus, upon completion of this step, a set of acceptable QRST sequences will have been identified, the QRS, which corresponds to points A, B and C in FIG. 9, portion of each being deemed an acceptable heart beat spike that may be used to calculate various heart related parameters therefrom, including, but not limited to, heart rate.

Figure 7F:
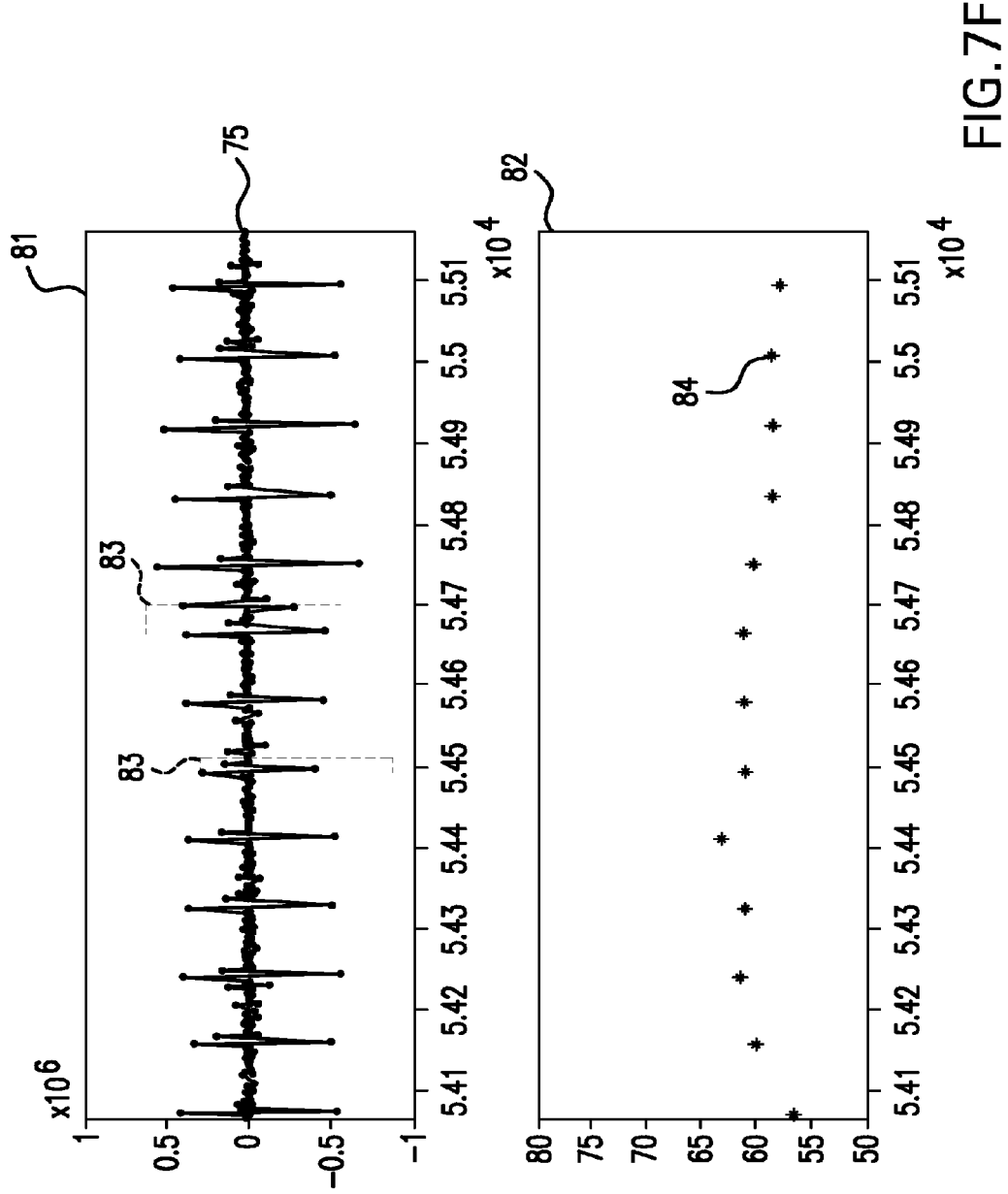

According to an alternate embodiment for identifying acceptable heart beat spikes, each up-down-up sequence, a possible QRST sequence, in the filtered signal is first identified. The heights of the components of the sequence are then calculated. The allowed amplitude of the candidate QRST complexes are required to be at least double the estimated amplitude of signal noise. In addition, the width of the sequence must not exceed 200 milliseconds, an upper limit for believable QRST complexes. Next, if a candidate QRS complex is still viable, the plausibility of the location in time for the complex given the current heart rate estimate is checked. If the change in heart rate implied by the candidate beat is less than fifty percent then the sequence is identified to be a heart beat. FIG. 7F shows this process utilizing detected signal 75, plotted as a series of interconnected data points forming QRST complexes in box 81. Signal boundary boxes 83 identify the two QRST complexes in detected signal 75 which are eliminated because they fail the 50% test described above. Heart beat peak points 84 are illustrated in box 82 which represent the QRST complexes identified as beats from box 81. Note the absence of heart beat peak points at the corresponding locations. Additionally, respiration data, including respiration rate, can be extracted from ECG waveforms. Respiration results in regular and detectable amplitude variations in the observed ECG. In terms of the equivalent dipole model of cardiac electrical activity, respiration induces an apparent modulation in the direction of the mean cardiac electrical axis.

Additional methodologies are presented for the analysis and display of the heart rate data. In each of these methods, the signal is serially segmented into a set of overlapping time slices based on identified QRST sequences. Each time slice is preferably exactly centered on the R point of a sequence and contains a fixed window of time, e.g. 1.5 seconds, on either side of the R point of that sequence. Each time slice may contain more than one QRST sequence, but will contain at least one in the center of the time slice. While the analysis is performed mathematically, a graphical description will provide the clearest understanding to those skilled in the art. Next, for a given point in time, some number of time slices before and after a given time slice are merged together or overlaid on the same graph. In one particular embodiment, 10 time slices before and after a given point are overlaid on the same graph In terms of graphic display, which is how this data may be presented to the user in the form of output, the time slice segments are overlapped, whereby some number of QRST sequences, or time slice segments, are overlaid on the same graph. Each detected primary QRST sequence and the neighboring sequences within the time slice segment, preferably 1.5 seconds, are overlaid on top of the other beats in that window. For example, in FIG. 10A, a series of signals 50 are overlapped with each other with primary beat 55 aligned between the overlapped signals. This is referred to as an AND-based overlapping-beat-graph. The average 60 of all the superimposed beats is also calculated and displayed. At the center of the graph, where primary beats 55 are aligned, the beats look very similar, and a clear signal is discernable. Also note that the neighboring beats 65 are tightly clustered, with some deviation, which is an indicator of beat to beat variability. One skilled in the art will discern that the heart rate for this set of beats is easily extracted from such a graph by looking at the distance between the center QRS complex and the center of the neighboring complexes. When the signal is very clear, as in this example, the utility of this calculation is limited. However, when the signal is noisy and many false beats are detected, this technique can allow for finding a heart rate when the signal itself is too noisy to use simplistic or observational methods.

Figure 10B:
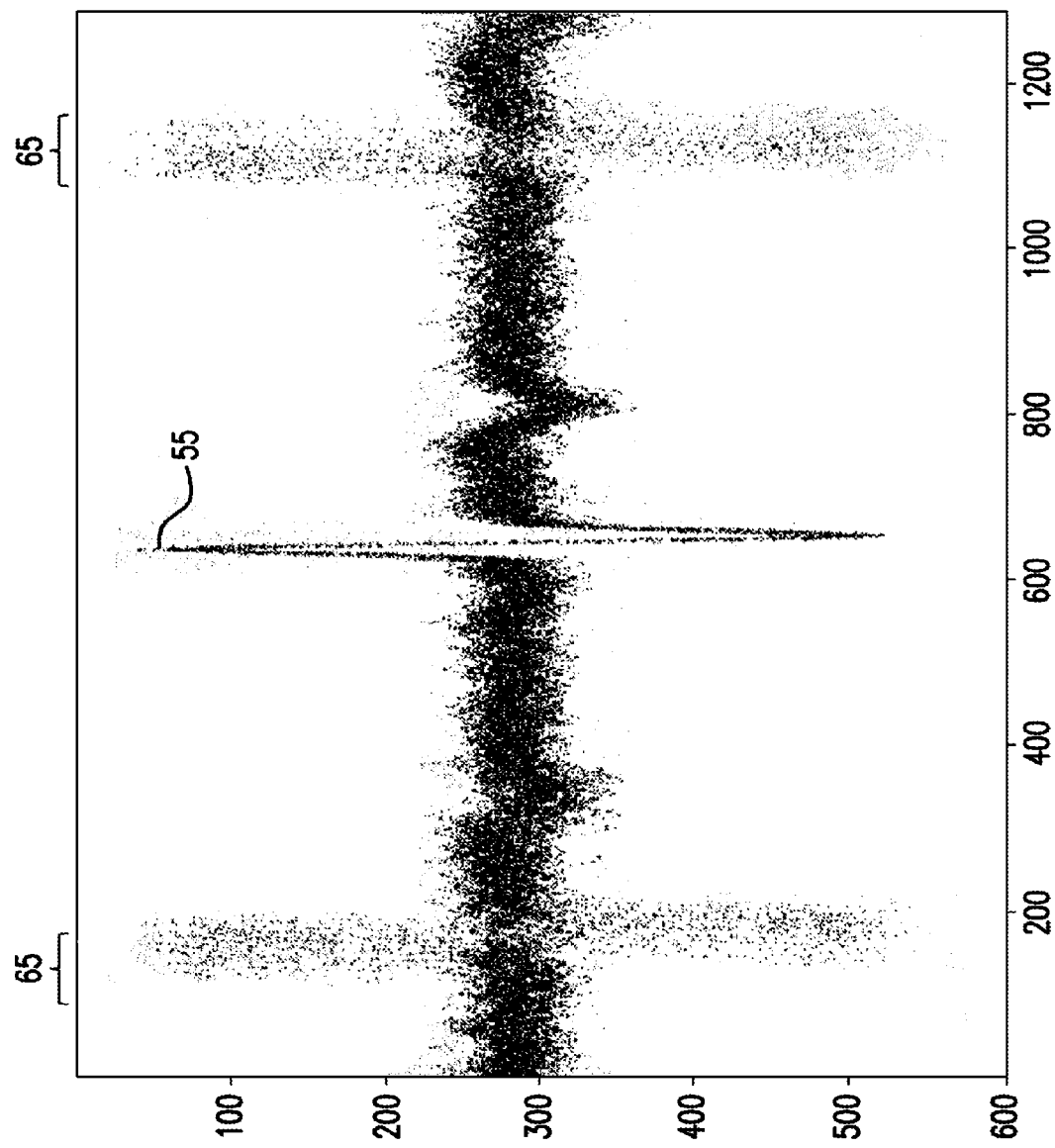

Another embodiment of the overlapping-beat-graph involves using a ADD-based approach to overlaps. In this version, as illustrated in FIG. 10B, when the beats and the neighboring signal overlap, the intensity of the pixel in the resulting graph is increased by the number of overlapping points. FIG. 10B illustrates an example for the ECG signal shown where the base color is black and each signal that overlaps makes the color brighter. Again, primary beat 55 is utilized to align the time slice segments and the neighboring beats 65 are shown as more of a cloud of points than in FIG. 10A. The width of this cloud of points is related to the beat to beat variability of the signal in question. Even though individual beats may not be reliably detected and the overlapped graph may not show a clear pattern in the lines, the average 60, as shown in FIG. 10A may be utilized to identify clear neighboring QRS complexes. From these, a rate can be determined from the distance from the center of the time slice to the center of the cloud of points representing the neighboring QRS sequences. An ADD-graph may be utilized to identify distinct spikes for the neighboring QRS complexes in the presence of significant noise to enhance the capabilities of the system. In an alternate embodiment, the display could be biased more heavily toward those pixels with more overlapping points such that if the number of overlapping points is X at a particular pixel, its intensity could represented as ×1.5, thereby more selectively highlighting the most overlapped points.

A method of establishing a database or other reference for the morphologies of the user's heart beat signal would necessarily include the ability to classify heart beat patterns and to identify certain morphologies. These patterns and morphologies could then be associated with certain activities or conditions. The first step, however, is to identify the morphologies and patterns, as follows.

For example, a set of N ECG wave forms may be selected. The average distance between beats is identified and a time period ½ of the interbeat period before and ½ of the interbeat period after to truncate each waveform. It is specifically noted that other clipping distances are possible and could be variable. As with the descriptions of beat matching above, a graphic description of the process is the most illuminating. N signal wave forms are detected in the clipping mode and are modeled, as with the ADD graphs above, with the signal features being measured by the intensity or brightness. The signal is assigned an intensity or numerical value. The surrounding area has no value. The equator line of each wave form is identified, being that horizontal line such that the areas above and below this line are equal. A meridian line is identified for each wave peak as that vertical line that subdivides the QRS spike into two pieces, split at the peak value of the signal. All N images are overlapped such that all equators are coincident and all meridians are coincident. All intensity or numerical values for each point in the N signals are normalized such that all values are between two known boundary values, such as 0 and 1000. The result is a representation that captures the average heart beat morphology for that person over that period of time including, within the non-coincident areas, signal segments where the wave forms tend to be most coincident, having the highest values and the least coincident, having the lowest values. In addition, each of the N images could be scaled prior to overlap, wherein the height of the R point of each wave forms a constant. Additionally, accuracy may be increased by selecting X segments of X wave forms in row and performing the above analysis with the sequence of X wave forms instead of just with one.

As will be appreciated by those of skill in the art, it is possible that the signal output by analog to digital converter 160 may have its polarity inverted as compared to what is expected from an ECG signal due to the placement of electrodes 150, in which case what would otherwise be peaks in the signal will appear as valleys in the signal. In such a case, the processing described above may be successfully performed on the signal by first inverting its polarity. In one embodiment of the present invention, the signal output by analog to digital converter 160 may be processed twice as described above, first without inverting its polarity and then again after its polarity has been inverted, with the best output being used for further processing as described herein. Additionally, the use of multiple sensors, such as an accelerometer or alternative pairs of electrodes, can be utilized to direct variable gain and dynamic signal thresholds or conditions during the signal processing in order to better adjust the types or nature of the processing to be applied. Additionally, a peak detector circuit may be employed such as that manufactured by Salutron, Fremont, Calif.

In addition, the system may detect known and recognizable contexts or signal patterns that will simply not present an acceptable signal that is discernable by the algorithms for beat and other body potential related feature detection. In these situations, the system simply recognizes this condition and records the data stream, such as when EMG or motion amplitude is at a peak level, the system detects this condition and discontinues attempting to process the signal until the next appropriate signal is received, according to certain preset or dynamically calculated conditions or thresholds. In some cases, the output of other sensors may be utilized to confirm the presence of a condition, such as excessive body motion, which would confirm that the system is operating properly, but lacking a coherent signal, as well as provide a basis for interpolation of the data from the missing segment of time. Under these conditions, a returned value from the system that no heart information could reliably collected is itself of value, relative to returning erroneous heart information.

Once acceptable heart beat spikes have been identified from the signal that is output by analog to digital converter 160 using one of the methods described herein, the acceptable heart beat spikes may be used to calculate heart rate using any of several methods. While merely counting the number of acceptable heart beat spikes in a particular time period, such as a minute, might seem like an acceptable way to calculate heart rate, it will be appreciated that such a method will actually underestimate heart rate because of the fact that a number of beats will likely have been invalidated as noise as described above. Thus, heart rate and other heart related parameters such as beat to beat variability and respiration rate must be calculated in a manner that accounts for invalidated beats. According to one embodiment, heart rate may be calculated from identified acceptable heart beat spikes by determining the distance, in time, between each group of two successive acceptable heart beat spikes identified in the signal and dividing sixty seconds by this time to get a local heart rate for each group of two successive acceptable heart beat spikes. Then, an average, median and/or peak of all of such local heart rates may be calculated in a given time period and used as the calculated heart rate value.

In the event that a period of time is encountered where no signal is available of a minimum level of quality for beat detection, a methodology must be developed by which the events of this time period are estimated. The system provides the ability to produce accurate statements about some heart parameters, including heart rate, for this missing time period. A probability is assigned to the heart beat frequency based upon the prior data which is reliable, by taking advantage of previously learned data and probabilities about how heart rates change through time. This is not limited to the time period immediately prior to the missing time segment, although this may be the best indicator of the missing section. The comparison can also be made to prior segments of time which have been stored and or categorized, or through matching to a database of information relating to heart parameters under certain conditions. The system can also take advantage of other sensors utilized in conjunction with the device in these computations of probability. For example the probability of missing heart beats on the heart beat channels can be utilized given that the variance of the accelerometer sensor is high. This enables very accurate assessments of different rate sequences and allows the calculation of a likely heart rate. This method is most successful when some minimum number of detected beats are present.

An additional method of estimating activity during missing time periods is to first identify candidate beats using one of the methods discussed above. Any detection technique that also produces a strength value can be used. In the preferred embodiment the detector will associate a probability that the located beat is in fact a heart beat. Binary true/false detectors can be used by using as strength value 1 for truth. Next, all pairs of potential beats are combined to give a set of inter-beat gaps. Each inter-beat gap defines a weighting function whose values are based on a combination of the size of the gap, the amount of time which has passed since the gap was detected, the strength of the identification and any meta-parameters needed by the family of weighting functions. In the preferred embodiment this weighting function is the inverse notch function. The inter-beat gap, in units of seconds, determines the location of the notch's peak. The height of the notch is driven by the strength of the identification, the length of time since the gap was identified, as age, and a hyper-parameter referred to as lifetime. The width of the notch is defined by the hyper-parameter width. FIG. 7G shows this inverse notch function including notch peak 87 and notch width 89. The function itself is mathematically expressed as:

In the third step, the individual weighting functions are summed to obtain a total weighting function. Finally, the resulting function is programmatically analyzed to obtain an estimate of heart rate.

Figure 7H:
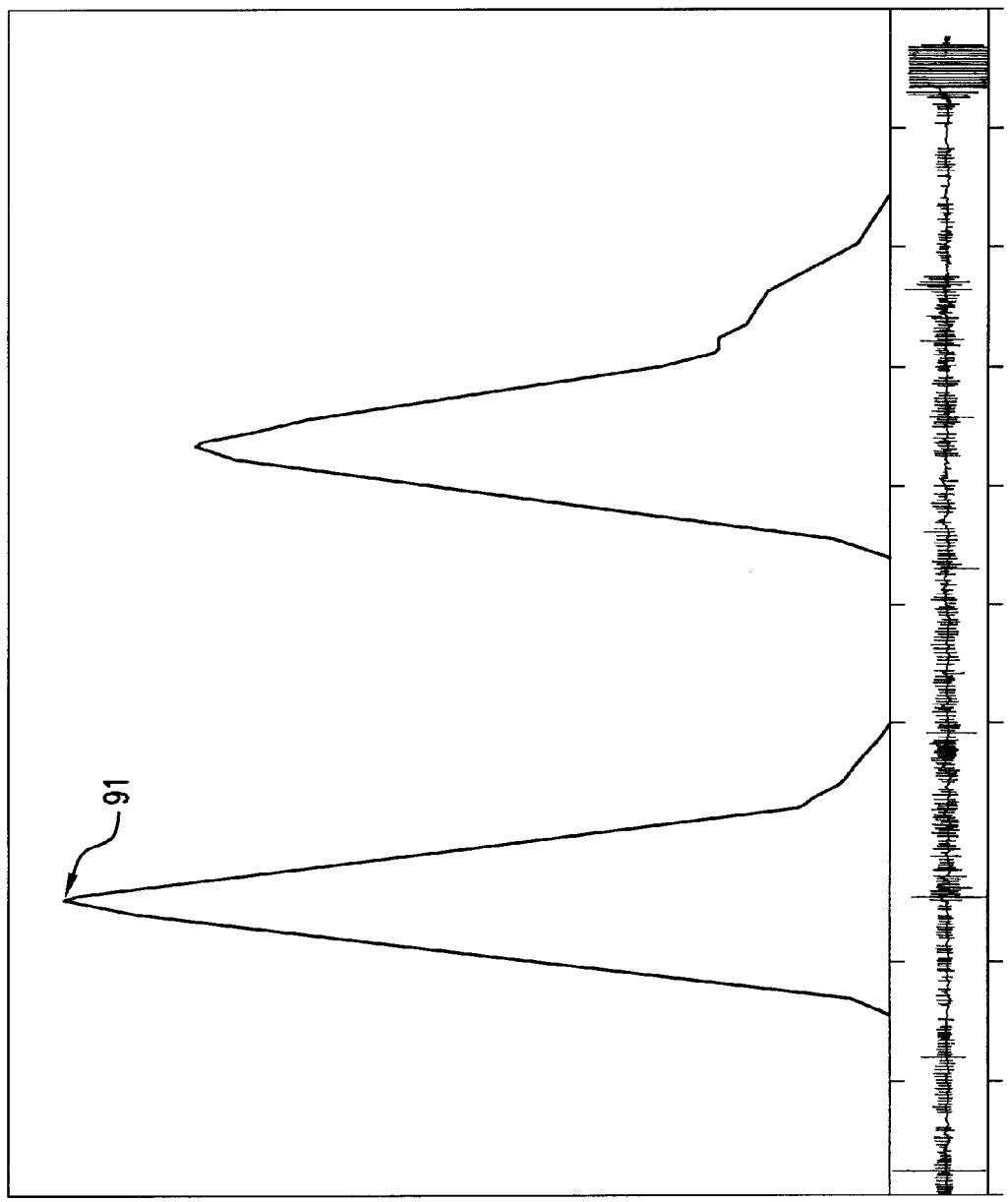

In the preferred embodiment, the estimate of the true inter-beat gap is taken to be the value at which the function reaches its first local maximum. FIG. 7H shows the resulting function and indicates the first local maximum 91. Once the inter-beat gap is selected, the heart rate is determined from the formula HeartRate=60/InterbeatGap.

To minimize the processing load associated with the evaluation of the total weighting function, those individual weighting functions whose inter-beat gaps are either larger or smaller than is physiologically possible are eliminated. In addition, individual functions whose age has exceeded the value of the lifetime hyper parameter are also eliminated.

Another embodiment utilizes probabilistic filters on the allowed inter-beat gaps instead of a hard truncation as described above. These probabilistic filters take as input one or more signals in addition to the ECG signal and determine a probabilistic range for the allowable heart beat. One instantiation of this is to determine the context of the wearer from the non-ECG signals and then, for each context, to apply a particular Gaussian distribution with parameters determined by the context, the wearer's body parameters, as well as the ECG signal itself. Other probability distributions can easily be utilized as well for this biasing. This probability can then be multiplied by the probability of each inter-beat gap to produce a posterior distribution, from which the most likely heart beat can be easily determined.

Another aspect of the present invention is that during times when certain heart parameters are not computable due to noise, these parameters can also be estimated from the set of measured values nearby in time and the sequences of other measurements made on other sensors. One such embodiment of this method is a contextual predictor similar to that used for energy expenditure, but instead used to predict heart rate from accelerometer data, galvanic skin response data, skin temperature and cover temperature data, as well as steps taken and other derived physiological and contextual parameters. This method first identifies the wearer's activity, and then applies an appropriate derivation for that activity. In the preferred embodiment, all derivations for all activities are applied and combined according to the probability of that activity being performed.

An additional aspect of the invention is a method of adaptation over time for a particular user through the use of multiple noisy signals that provide feedback as to the quality of other derived signals. Another way of viewing this is as a method of calibration for a given user. First, a given derived parameter is calculated, representing some physiological state of the wearer. Second, a second derived parameter is calculated, representing the same physiological state. These two derived parameters are compared, and used to adjust one another, according to the confidences calculated for each of the derived metrics. The calculations are designed to accept a feedback signal to allow for training or tuning them. In one embodiment, this consists of merely utilizing gradient descent to tune the parameters based on the admittedly noisy feedback signal. In another embodiment, this involves updating a set of constants utilized in the computation based on a system of probabilistic inference.

According to one aspect of the present invention, an algorithm development process is used to create a wide range of algorithms for generating continuous information relating to a variety of variables from the data received from the plurality of physiological and/or contextual sensors on armband body monitoring device 300, as identified in Table I hereto, including the ECG signal generated using electrodes 105 that is used to calculate heart rate and other heart related parameters, many of which cannot be distinguished by visual recognition from graphical data output and diagnostics alone. These include heart rate variability, heart rate deviation, average heart rate, respiration rate, atrial fibrillation, arrhythmia, inter-beat intervals, inter-beat interval variability and the like. Additionally, continuous monitoring of this type, coupled with the ability to event- or time-stamp the data in real time, provides the ability to titrate the application of drugs or other therapies and observe the immediate and long term effects thereof. Moreover, the ability is presented, through pattern recognition and analysis of the data output, to predict certain conditions, such as cardiac arrhythmias, based upon prior events. Such variables may include, without limitation, energy expenditure, including resting, active and total values; daily caloric intake; sleep states, including in bed, sleep onset, sleep interruptions, wake, and out of bed; and activity states, including exercising, sitting, traveling in a motor vehicle, and lying down. The algorithms for generating values for such variables may be based on data from, for example, an axis or both axes of a 2-axis accelerometer, a heat flux sensor, a GSR sensor, a skin temperature sensor, a near-body ambient temperature sensor, and a heart rate sensor in the embodiments described herein. Additionally, through the pattern detection and prediction capabilities described above, the system may predict the onset of certain events such as syncope, arrhythmia and certain physiological mental health states by establishing a known condition set of parameters during one such episode of such an event and detecting similar pre-event parameters. An alarm or other feedback would be presented to the user upon the reoccurrence of that particular set of parameters matching the prior event.

The monitoring device is capable of generating data indicative of various additional physiological parameters of an individual which would be helpful as part of the predictive and parameter identification functionality described above. This includes, in addition to those parameters described elsewhere, respiration rate, skin temperature, core body temperature, heat flow off the body, galvanic skin response or GSR, EMG, EEG, EOG, blood pressure, body fat, hydration level, activity level, oxygen consumption, glucose or blood sugar level, body position, pressure on muscles or bones, and UV radiation exposure and absorption. In certain cases, the data indicative of the various physiological parameters is the signal or signals themselves generated by the one or more sensors and in certain other cases the data is calculated by the microprocessor based on the signal or signals generated by the one or more sensors. Methods for generating data indicative of various physiological parameters and sensors to be used therefor are well known. Table 1 provides several examples of such well known methods and shows the parameter in question, the method used, the sensor device used, and the signal that is generated. Table 1 also provides an indication as to whether further processing based on the generated signal is required to generate the data.

TABLE 1

| Parameter | Example Method | Example Sensor | Signal | Further Processing |
|---|---|---|---|---|
| Heart Rate | EKG | 2 Electrodes | DC Voltage | Yes |
| Pulse Rate | BVP | LED Emitter and Optical Sensor | Change in Resistance | Yes |
| Beat-to-Beat Variability | Heart Rate | 2 Electrodes | DC Voltage | Yes |
| EKG | Skin Surface Potentials | 3-10 Electrodes | DC Voltage | No |
| Respiration Rate | Chest Volume Change | Strain Gauge | Change in Resistance | Yes |
| Skin Temperature | Surface Temperature Probe | Thermistors | Change in Resistance | Yes |
| Core Temperature | Esophageal or Rectal Probe | Thermistors | Change in Resistance | Yes |
| Heat Flow | Heat Flux | Thermopile | DC Voltage | Yes |
| Galvanic Skin Response | Skin Conductance | 2 Electrodes | Change in Resistance | No |
| EMG | Skin Surface Potentials | 3 Electrodes | DC Voltage | No |
| EEG | Skin Surface Potentials | Multiple Electrodes | DC Voltage | Yes |
| EOG | Eye Movement | Thin Film Piezoelectric Sensors | DC Voltage | Yes |
| Blood Pressure | Non-Invasive Korotkuff Sounds | Electronic Sphygromarometer | Change in Resistance | Yes |
| Body Fat | Body Impedance | 2 Active Electrodes | Change in Impedance | Yes |
| Activity in Interpreted G Shocks per Minute | Body Movement | Accelerometer | DC Voltage, Capacitance Changes | Yes |
| Oxygen Consumption | Oxygen Uptake | Electro-chemical | DC Voltage Change | Yes |
| Glucose Level | Non-Invasive | Electro-chemical | DC Voltage Change | Yes |
| Body Position (e.g. supine, erect, sitting) | N/A | Mercury Switch Array | DC Voltage Change | Yes |
| Muscle Pressure | N/A | Thin Film Piezoelectric Sensors | DC Voltage Change | Yes |
| UV Radiation Absorption | N/A | UV Sensitive Photo Cells | DC Voltage Change | Yes |

It is to be specifically noted that a number of other types and categories of sensors may be utilized alone or in conjunction with those given above, including but not limited to relative and global positioning sensors for determination of motion or location of the user; torque & rotational acceleration for determination of orientation in space; blood chemistry sensors; interstitial fluid chemistry sensors; bio-impedance sensors; and several contextual sensors, such as: pollen, humidity, ozone, acoustic, body and ambient noise and sensors adapted to utilize the device in a biofingerprinting scheme.

The types of data listed in Table 1 are intended to be examples of the types of data that can be generated by the monitoring device. It is to be understood that other types of data relating to other parameters can be generated without departing from the scope of the present invention. Additionally, certain information may be derived from the above data, relating to an individual's physiological state. Table 2 provides examples of the type of information that can be derived and indicates some of the tunes of data that can be used therefor.

TABLE 2

| Derived Information | Example of Data Used |
| --- | --- |
| Ovulation | Skin temperature, core temperature, oxygen consumption |
| Sleep onset/wake | Beat-to-beat variability, heart rate, pulse rate, respiration rate, skin temperature, core temperature, heat flow, galvanic skin response, EMG, EEG, EOG, blood pressure, oxygen consumption |
| Calories burned | Heart rate, pulse rate, respiration rate, heat flow, activity, oxygen consumption |
| Basal metabolic rate | Heart rate, pulse rate, respiration rate, heat flow, activity, oxygen consumption |
| Basal temperature | Skin temperature, core temperature |
| Activity level | Heart rate, pulse rate, respiration rate, heat flow, activity, oxygen consumption |
| Stress level | EKG, beat-to-beat variability, heart rate, pulse rate, respiration rate, skin temperature, heat flow, galvanic skin response, EMG, EEG, blood pressure, activity, oxygen consumption |
| Relaxation level | EKG, beat-to-beat variability, heart rate, pulse rate, respiration rate, skin temperature, heat flow, galvanic skin response, EMG, EEG, blood pressure, activity, oxygen consumption |
| Maximum oxygen consumption rate | EKG, heart rate, pulse rate, respiration rate, heat flow, blood pressure, activity, oxygen consumption |
| Rise time or the time it takes to rise from a resting rate to 85% of a target maximum | Heart rate, pulse rate, heat flow, oxygen consumption |
| Time in zone or the time heart rate was above 85% of a target maximum | Heart rate, pulse rate, heat flow, oxygen consumption |
| Recovery time or the time it takes heart rate to return to a resting rate after heart rate was above 85% of a target maximum | Heart rate, pulse rate, heat flow, oxygen consumption |

Additionally, the device may also generate data indicative of various contextual parameters such as activity states or other data relating to the environment surrounding the individual. For example, air quality, sound level/quality, light quality or ambient temperature near the individual, or even the global positioning of the individual.

In order to derive information from the sensors and data types herein, a series of algorithms are developed for predicting user characteristics, continual measurements, durative contexts, instantaneous events, and cumulative conditions. User characteristics include permanent and semi-permanent parameters of the wearer, including aspects such as weight, height, and wearer identity. An example of a continual measurement is energy expenditure, which constantly measures, for example on a minute by minute basis, the number of calories of energy expended by the wearer. Durative contexts are behaviors that last some period of time, such as sleeping, driving a car, or jogging. Instantaneous events are those that occur at a fixed or over a very short time period, such as a heart attack or falling down. Cumulative conditions are those where the person's condition can be deduced from their behavior over some previous period of time. For example, if a person hasn't slept in 36 hours and hasn't eaten in 10 hours, it is likely that they are fatigued. Table 3 below shows numerous examples of specific personal characteristics, continual measurements, durative measurements, instantaneous events, and cumulative conditions.

TABLE 3

| Example personal characteristics | age, sex, weight, gender, athletic ability, conditioning, disease, height, susceptibility to disease, activity level, individual detection, handedness, metabolic rate, body composition |
| --- | --- |

TABLE 3-continued

| Example continual measurements | mood, beat-to-beat variability of heart beats, respiration, energy expenditure, blood glucose levels, level of ketosis, heart rate, stress levels, fatigue levels, alertness levels, blood pressure, readiness, strength, endurance, amenability to interaction, steps per time period, stillness level, body position and orientation, cleanliness, mood or affect, approachability, caloric intake, TEF, XEF, 'in the zone'-ness, active energy expenditure, carbohydrate intake, fat intake, protein intake, hydration levels, truthfulness, sleep quality, sleep state, consciousness level, effects of medication, |
| --- | --- |

TABLE 3-continued

| | |
|---|---|
| | dosage prediction, water intake, alcohol intake, dizziness, pain, comfort, remaining processing power for new stimuli, proper use of the armband, interest in a topic, relative exertion, location, blood-alcohol level |
| Example durative measurements | exercise, sleep, lying down, sitting, standing, ambulation, running, walking, biking, stationary biking, road biking, lifting weights, aerobic exercise, anaerobic exercise, strength-building exercise, mind-centering activity, periods of intense emotion, relaxing, watching TV, sedentary, REM detector, eating, in-the-zone, interruptible, general activity detection, sleep stage, heat stress, heat stroke, amenable to teaching/learning, bipolar decompensation, abnormal events (in heart signal, in activity level, measured by the user, etc), startle level, highway driving or riding in a car, airplane travel, helicopter travel, boredom events, sport detection (football, baseball, soccer, etc), studying, reading, intoxication, effect of a drug |
| Example instantaneous events | falling, heart attack, seizure, sleep arousal events, PVCs, blood sugar abnormality, acute stress or disorientation, emergency, heart arrhythmia, shock, vomiting, rapid blood loss, taking medication, swallowing |
| Example cumulative conditions | Alzheimer's, weakness or increased likelihood of falling, drowsiness, fatigue, existence of ketosis, ovulation, pregnancy, disease, illness, fever, edema, anemia, having the flu, hypertension, mental disorders, acute dehydration, hypothermia, being-in-the-zone |

It will be appreciated that the present invention may be utilized in a method for doing automatic journaling of a wearer's physiological and contextual states. The system can automatically produce a journal of what activities the user was engaged in, what events occurred, how the user's physiological state changed over time, and when the user experienced or was likely to experience certain conditions. For example, the system can produce a record of when the user exercised, drove a car, slept, was in danger of heat stress, or ate, in addition to recording the user's hydration level, energy expenditure level, sleep levels, and alertness levels throughout a day. These detected conditions can be utilized to time- or event-stamp the data record, to modify certain parameters of the analysis or presentation of the data, as well as trigger certain delayed or real time feedback events.

According to the algorithm development process, linear or non-linear mathematical models or algorithms are constructed that map the data from the plurality of sensors to a desired variable. The process consists of several steps. First, data is collected by subjects wearing armband body monitoring device 300 who are put into situations as close to real world situations as possible, with respect to the parameters being measured, such that the subjects are not endangered and so that the variable that the proposed algorithm is to predict can, at the same time, be reliably measured using, for example, highly accurate medical grade lab equipment. This first step provides the following two sets of data that are then used as inputs to the algorithm development process: (i) the raw data from armband body monitoring device 300, and (ii) the data consisting of the verifiably accurate data measurements and extrapolated or derived data made with or calculated from the more accurate lab equipment. This verifiable data becomes a standard against which other analytical or measured data is compared. For cases in which the variable that the proposed algorithm is to predict relates to context detection, such as traveling in a motor vehicle, the verifiable standard data is provided by the subjects themselves, such as through information input manually into armband body monitoring device 300, a PC, or otherwise manually recorded. The collected data, i.e., both the raw data and the corresponding verifiable standard data, is then organized into a database and is split into training and test sets.

Next, using the data in the training set, a mathematical model is built that relates the raw data to the corresponding verifiable standard data. Specifically, a variety of machine learning techniques are used to generate two types of algorithms: 1) algorithms known as features, which are derived continuous parameters that vary in a manner that allows the prediction of the lab-measured parameter for some subset of the data points. The features are typically not conditionally independent of the lab-measured parameter e.g. VO2 level information from a metabolic cart, douglas bag, or doubly labeled water, and 2) algorithms known as context detectors that predict various contexts, e g, running, exercising, lying down, sleeping or driving, useful for the overall algorithm. A number of well known machine learning techniques may be used in this step, including artificial neural nets, decision trees, memory-based methods, boosting, attribute selection through cross-validation, and stochastic search methods such as simulated annealing and evolutionary computation.

After a suitable set of features and context detectors are found, several well known machine learning methods are used to combine the features and context detectors into an overall model. Techniques used in this phase include, but are not limited to, multilinear regression, locally weighted regression, decision trees, artificial neural networks, stochastic search methods, support vector machines, and model trees. These models are evaluated using cross-validation to avoid over-fitting.

At this stage, the models make predictions on, for example, a minute by minute basis. Inter-minute effects are next taken into account by creating an overall model that integrates the minute by minute predictions. A well known or custom windowing and threshold optimization tool may be used in this step to take advantage of the temporal continuity of the data. Finally, the model's performance can be evaluated on the test set, which has not yet been used in the creation of the algorithm. Performance of the model on the test set is thus a good estimate of the algorithm's expected performance on other unseen data. Finally, the algorithm may undergo live testing on new data for further validation.

Further examples of the types of non-linear functions and/or machine learning method that may be used in the present invention include the following: conditionals, case statements, logical processing, probabilistic or logical inference, neural network processing, kernel based methods, memory-based lookup including kNN and SOMs, decision lists, decision-tree prediction, support vector machine prediction, clustering, boosted methods, cascade-correlation, Boltzmann classifiers, regression trees, case-based reasoning, Gaussians, Bayes nets, dynamic Bayesian networks, HMMs, Kalman filters, Gaussian processes and algorithmic predictors, e.g. learned by evolutionary computation or other program synthesis tools.

Although one can view an algorithm as taking raw sensor values or signals as input, performing computation, and then producing a desired output, it is useful in one preferred embodiment to view the algorithm as a series of derivations that are applied to the raw sensor values. Each derivation produces a signal referred to as a derived channel. The raw sensor values or signals are also referred to as channels, specifically raw channels rather than derived channels. These derivations, also referred to as functions, can be simple or complex but are applied in a predetermined order on the raw values and, possibly, on already existing derived channels.

The first derivation must, of course, only take as input raw sensor signals and other available baseline information such as manually entered data and demographic information about the subject, but subsequent derivations can take as input previously derived channels. Note that one can easily determine, from the order of application of derivations, the particular channels utilized to derive a given derived channel. Also note that inputs that a user provides on an Input/Output, or I/O, device or in some fashion can also be included as raw signals which can be used by the algorithms. For example, the category chosen to describe a meal can be used by a derivation that computes the caloric estimate for the meal. In one embodiment, the raw signals are first summarized into channels that are sufficient for later derivations and can be efficiently stored. These channels include derivations such as summation, summation of differences, and averages. Note that although summarizing the high-rate data into compressed channels is useful both for compression and for storing useful features, it may be useful to store some or all segments of high rate data as well, depending on the exact details of the application. In one embodiment, these summary channels are then calibrated to take minor measurable differences in manufacturing into account and to result in values in the appropriate scale and in the correct units. For example, if, during the manufacturing process, a particular temperature sensor was determined to have a slight offset, this offset can be applied, resulting in a derived channel expressing temperature in degrees Celsius.

For purposes of this description, a derivation or function is linear if it is expressed as a weighted combination of its inputs together with some offset. For example, if G and H are two raw or derived channels, then all derivations of the form $A*G+B*H+C$, where A, B, and C are constants, is a linear derivation. A derivation is non-linear with respect to its inputs if it can not be expressed as a weighted sum of the inputs with a constant offset. An example of a nonlinear derivation is as follows: if $G>7$ then return $H*9$, else return $H*3.5+912$. A channel is linearly derived if all derivations involved in computing it are linear, and a channel is nonlinearly derived if any of the derivations used in creating it are nonlinear. A channel nonlinearly mediates a derivation if changes in the value of the channel change the computation performed in the derivation, keeping all other inputs to the derivation constant.

Figure 11:
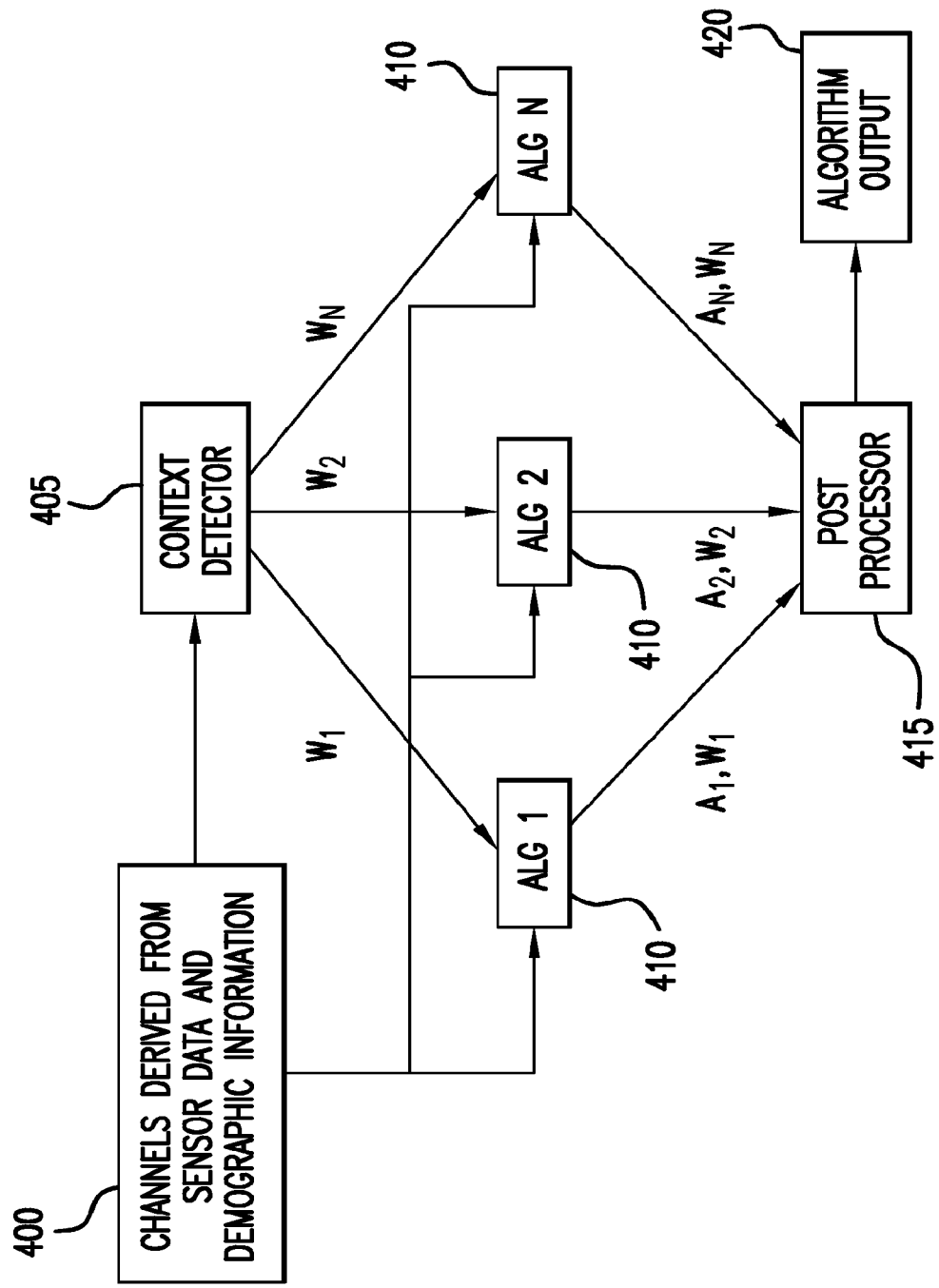
FIG. 11 is a block diagram showing the format of algorithms that are developed according to an aspect of the present invention.

According to a preferred embodiment of the present invention, the algorithms that are developed using this process will have the format shown conceptually in FIG. 11. Specifically, the algorithm will take as inputs the channels derived from the sensor data collected by armband body monitoring device 300 from the various sensors, including the heart rate and other heart related parameters calculated from the ECG signal generated using electrodes 105 and demographic information for the individual as shown in box 400. The algorithm includes at least one context detector 405 that produces a weight, shown as W1 through WN, expressing the probability that a given portion of collected data, such as is collected over a minute, was collected while the wearer was in each of several possible contexts. Such contexts may include whether the individual was at rest or active. In addition, for each context, a regression algorithm 410 is provided where a continuous prediction is computed taking raw or derived channels as input. The individual regressions can be any of a variety of regression equations or methods, including, for example, multivariate linear or polynomial regression, memory based methods, support vector machine regression, neural networks, Gaussian processes, arbitrary procedural functions and the like. Each regression is an estimate of the output of the parameter of interest in the algorithm, for example, energy expenditure. Finally, the outputs of each regression algorithm 410 for each context, shown as A1 through AN, and the weights W1 through WN are combined in a post-processor 415 which outputs the parameter of interest being measured or predicted by the algorithm, shown in box 420. In general, the post-processor 415 can consist of any of many methods for combining the separate contextual predictions, including committee methods, boosting, voting methods, consistency checking, or context based recombination.

Figure 12:
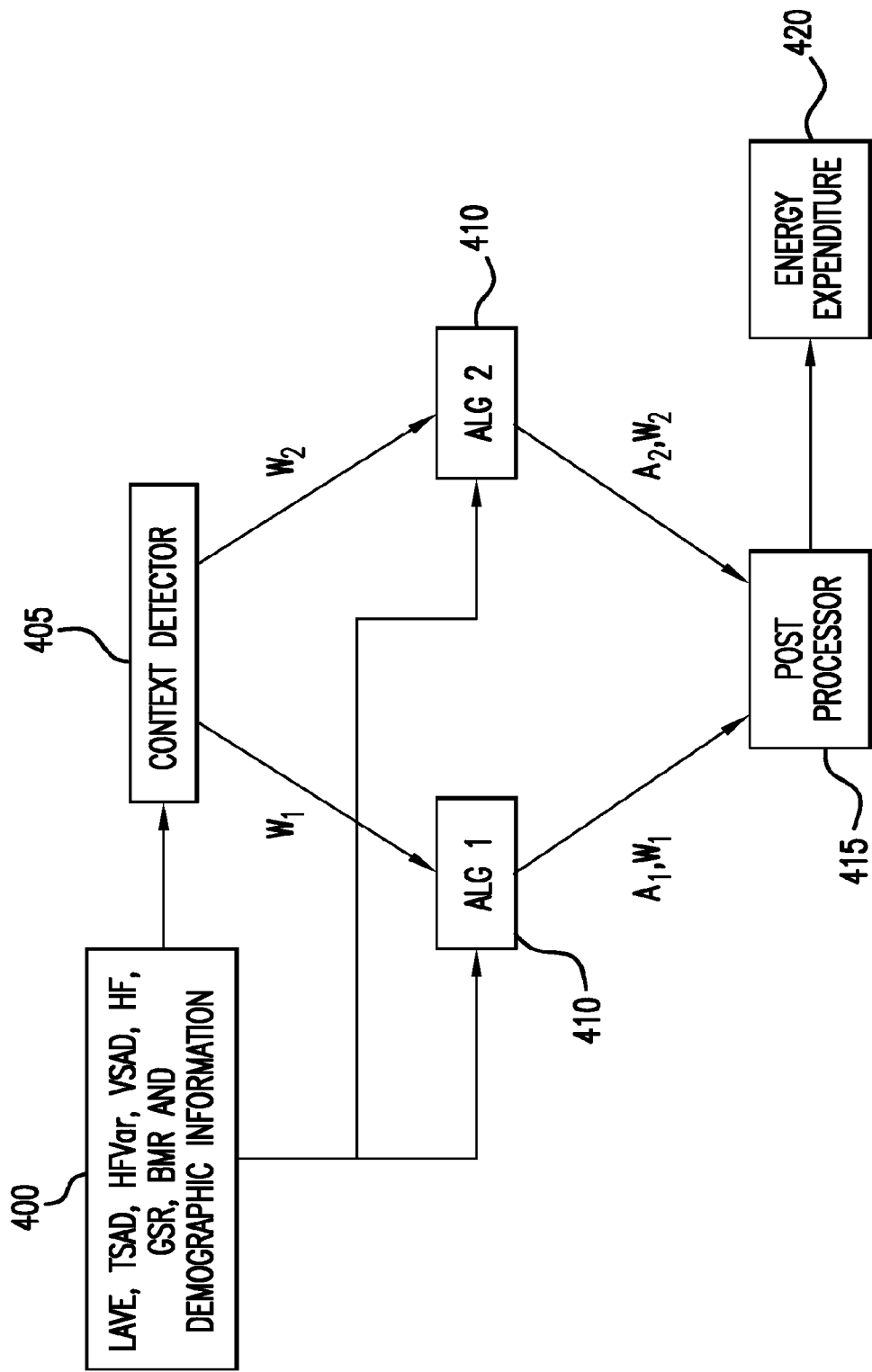
FIG. 12 is a block diagram illustrating an example algorithm for predicting energy expenditure according to an aspect of the present invention.

Referring to FIG. 12, an example algorithm for measuring energy expenditure of an individual is shown. This example algorithm may be run on armband body monitoring device 300 having at least an accelerometer, a heat flux sensor and a GSR sensor, or an I/O device that receives data from such an armband body monitoring device as is disclosed in co-pending U.S. patent application Ser. No. 10/682,759, the specification of which is incorporated herein by reference. In this example algorithm, the raw data from the sensors is calibrated and numerous values based thereon, i.e., derived channels, are created. In particular, the following derived channels, shown at 400 in FIG. 12, are computed from the raw signals and the demographic information: (1) longitudinal accelerometer average, or LAVE, based on the accelerometer data; (2) transverse accelerometer sum of average differences, or TSAD, based on the accelerometer data; (3) heat flux high gain average variance, or HFvar, based on heat flux sensor data; (4) vector sum of transverse and longitudinal accelerometer sum of absolute differences or SADs, identified as VSAD, based on the accelerometer data; (5) galvanic skin response, or GSR, in both low and combined gain embodiments; and (6) Basal Metabolic Rate or BMR, based on demographic information input by the user. Context detector 405 consists of a naïve Bayesian classifier that predicts whether the wearer is active or resting using the LAVE, TSAD, and HFvar derived channels. The output is a probabilistic weight, W1 and W2 for the two contexts rest and active. For the rest context, the regression algorithm 410 is a linear regression combining channels derived from the accelerometer, the heat flux sensor, the user's demographic data, and the galvanic skin response sensor. The equation, obtained through the algorithm design process, is $A*VSAD+B*HFvar+C*GSR+D*BMR+E$, where A, B, C, D and E are constants. The regression algorithm 410 for the active context is the same, except that the constants are different. The post-processor 415 for this example is to add together the weighted results of each contextual regression. If A1 is the result of the rest regression and A2 is the result of the active regression, then the combination is just $W1*A1+W2*A2$, which is energy expenditure shown at 420. In another example, a derived channel that calculates whether the wearer is motoring, that is, driving in a car at the time period in question might also be input into the post-processor 415. The process by which this derived motoring channel is computed is algorithm 3. The post-processor 415 in this case might then enforce a constraint that when the wearer is predicted to be driving by algorithm 3, the energy expenditure is limited for that time period to a value equal to some factor, e.g. 1.3 times their minute by minute basal metabolic rate.

As another example, an algorithm having the format shown conceptually in FIG. 11 may be developed for measuring energy expenditure of an individual that utilizes as inputs the channels derived from the sensor data collected by armband body monitoring device 300 from the 2-axis accelerometer and the electrodes 105, from which heart rate and/or other heart related parameters are calculated. The parameters derived from these motion and heart rate sensor types are largely orthogonal and are very descriptive of a user's activities. The combination of these two sensors in an algorithm having the format shown conceptually in FIG. 11 provides the ability to easily distinguish between different activity classes that might be confusing to a single sensor, such as stressful events, some of which could be identified by high heart rate and low motion, vehicular motion events, some of which could be identified by low heart rate and high motion and exercise events, some of which could be identified by high heart rate and high motion. As shown in FIG. 11, in this embodiment, the channels derived from the sensor data from these two sensors are first used to detect the context of the user. The appropriate function or functions are then used to predict energy expenditure based on both heart rate and motion data. As a further alternative, channels derived from additional sensors forming a part of armband body monitoring device 300, such as a heat flux sensor may also be used as additional inputs into the algorithm. Using heart rate in an algorithm for predicting energy expenditure can result in a better, more accurate prediction for a number of reasons. For example, some low motion exercises such as biking or weight lifting pose issues for an energy expenditure algorithm that uses arm motion from an accelerometer as a sole input. Also, clothing may adversely affect measurements made by a heat flux sensor, which in turn may adversely effect energy expenditure predictions. Incorporating heart rate or other heart related parameters into an algorithm helps to alleviate such problems. Obviously, there is considerable utility in the mere detection, analysis and reporting of the heart rate and other heart related parameters alone, other than for use in such algorithms. Moreover, heart rate generally slows when someone falls asleep, and rises during REM periods. Thus, algorithms for predicting whether someone is sleeping and what stage of sleep they are in may be developed in accordance with the present invention that utilize as an input, along with other sensor data, data collected by armband body monitoring device 300 from the electrodes 105 from which heart rate and/or other heart related parameters are calculated as well as the other detected data types identified herein. Such heart related data may also be used in algorithms for detecting various sleep disorders, such as sleep apnea. Similarly, when under stress, a person's heart rate often rises without an accompanying increase in motion or body heat. Day to day or time period to time period comparisons of such data for an individual will assist in identifying certain patterns or conditions which may be used for both further pattern detection or prediction. Algorithms for detecting stress may be developed in accordance with the present invention that utilize data collected from the electrodes 105, from which heart rate and/or other heart related parameters are calculated, along with other sensor data such as data from an accelerometer. While the applicability of recognizing stress is most likely in the context of reviewing past activity and attempting to correlate the detected and derived parameters with life activities or other non-detectable events, the ability to detect stress may be effective as a contemporaneous measurement to identify a condition that may be masked from the wearer by external conditions or merely preoccupation. This is especially true in the event that the heart is undergoing stress in the absence of physical exertion or activity.

Other important feedback embodiments include the ability to detect REM sleep through the heart related parameters and to maximize the wearer's opportunity to engage in such sleep. Rather than the conventional alarm waking the user at a preappointed time, the alarm could wake the wearer after a preset amount of REM sleep, and further at an appropriate endpoint of such sleep or during or just after some particular sleep stage.

This algorithm development process may also be used to create algorithms to enable armband body monitoring device 300 to detect and measure various other parameters, including, without limitation, the following: (i) when an individual is suffering from duress, including states of unconsciousness, fatigue, shock, drowsiness, heat stress and dehydration; and (ii) an individual's state of readiness, health and/or metabolic status, such as in a military environment, including states of dehydration, under-nourishment and lack of sleep. In addition, algorithms may be developed for other purposes, such as filtering, signal clean-up and noise cancellation for signals measured by a sensor device as described herein. As will be appreciated, the actual algorithm or function that is developed using this method will be highly dependent on the specifics of the sensor device used, such as the specific sensors and placement thereof and the overall structure and geometry of the sensor device. Thus, an algorithm developed with one sensor device will not work as well, if at all, on sensor devices that are not substantially structurally identical to the sensor device used to create the algorithm.

It is to be specifically understood that the method for creation of algorithms described above can be applied utilizing the detected signal from the apparatus as input to provide a methodology for beat detection. The detected signal is treated as a channel, as described above and the same techniques are applied.

Another aspect of the present invention relates to the ability of the developed algorithms to handle various kinds of uncertainty. Data uncertainty refers to sensor noise and possible sensor failures. Data uncertainty is when one cannot fully trust the data. Under such conditions, for example, if a sensor, for example an accelerometer, fails, the system might conclude that the wearer is sleeping or resting or that no motion is taking place. Under such conditions it is very hard to conclude if the data is bad or if the model that is predicting and making the conclusion is wrong. When an application involves both model and data uncertainties, it is very important to identify the relative magnitudes of the uncertainties associated with data and the model. An intelligent system would notice that the sensor seems to be producing erroneous data and would either switch to alternate algorithms or would, in some cases, be able to fill the gaps intelligently before making any predictions. When neither of these recovery techniques are possible, as was mentioned before, returning a clear statement that an accurate value can not be returned is often much preferable to returning information from an algorithm that has been determined to be likely to be wrong. Determining when sensors have failed and when data channels are no longer reliable is a non-trivial task because a failed sensor can sometimes result in readings that may seem consistent with some of the other sensors and the data can also fall within the normal operating range of the sensor.

Clinical uncertainty refers to the fact that different sensors might indicate seemingly contradictory conclusions. Clinical uncertainty is when one cannot be sure of the conclusion that is drawn from the data. For example, the accelerometers might indicate that the wearer is motionless, leading toward a conclusion of a resting user, the galvanic skin response sensor might provide a very high response, leading toward a conclusion of an active user, the heat flow sensor might indicate that the wearer is still dispersing substantial heat, leading toward a conclusion of an active user, and the heart rate sensor might indicate that the wearer has an elevated heart rate, leading toward a conclusion of an active user. An inferior system might simply try to vote among the sensors or use similarly unfounded methods to integrate the various readings. The present invention weights the important joint probabilities and determines the appropriate most likely conclusion, which might be, for this example, that the wearer is currently performing or has recently performed a low motion activity such as stationary biking.

This same algorithm development process was used to develop the algorithms disclosed above for detecting heart beats, for determining heart rate, and for estimating heart rate in the presence of noise. It will be clear to one skilled in the art that this same process could be utilized to both incorporate other sensors to improve the measurement of heart related parameters or to incorporate heart related parameters into the measurement of other physiological parameters such as energy expenditure.

According to a further aspect of the present invention, a sensor device such as armband body monitoring device 300 may be used to automatically measure, record, store and/or report a parameter Y relating to the state of a person, preferably a state of the person that cannot be directly measured by the sensors. State parameter Y may be, for example and without limitation, calories consumed, energy expenditure, sleep states, hydration levels, ketosis levels, shock, insulin levels, physical exhaustion and heat exhaustion, among others. The sensor device is able to observe a vector of raw signals consisting of the outputs of certain of the one or more sensors, which may include all of such sensors or a subset of such sensors. As described above, certain signals, referred to as channels same potential terminology problem here as well, may be derived from the vector of raw sensor signals as well. A vector X of certain of these raw and/or derived channels, referred to herein as the raw and derived channels X, will change in some systematic way depending on or sensitive to the state, event and/or level of either the state parameter Y that is of interest or some indicator of Y, referred to as U, wherein there is a relationship between Y and U such that Y can be obtained from U. According to the present invention, a first algorithm or function f1 is created using the sensor device that takes as inputs the raw and derived channels X and gives an output that predicts and is conditionally dependent, expressed with the symbol $\Pi$, on (i) either the state parameter Y or the indicator U, and (ii) some other state parameter(s) Z of the individual. This algorithm or function f1 may be expressed as follows:

$$f1(X) \not\Pi U+Z$$

or $$f1(X) \not\Pi Y+Z$$

According to the preferred embodiment, f1 is developed using the algorithm development process described elsewhere herein which uses data, specifically the raw and derived channels X, derived from the signals collected by the sensor device, the verifiable standard data relating to U or Y and Z contemporaneously measured using a method taken to be the correct answer, for example highly accurate medical grade lab equipment, and various machine learning techniques to generate the algorithms from the collected data. The algorithm or function f1 is created under conditions where the indicator U or state parameter Y, whichever the case may be, is present. As will be appreciated, the actual algorithm or function that is developed using this method will be highly dependent on the specifics of the sensor device used, such as the specific sensors and placement thereof and the overall structure and geometry of the senor device. Thus, an algorithm developed with one sensor device will not work as well, if at all, on sensor devices that are not substantially structurally identical to the sensor device used to create the algorithm or at least can be translated from device to device or sensor to sensor with known conversion parameters.

Next, a second algorithm or function f2 is created using the sensor device that takes as inputs the raw and derived channels X and gives an output that predicts and is conditionally dependent on everything output by f1 except either Y or U, whichever the case may be, and is conditionally independent, indicated by the symbol $\Pi$, of either Y or U, whichever the case may be. The idea is that certain of the raw and derived channels X from the one or more sensors make it possible to explain away or filter out changes in the raw and derived channels X coming from non-Y or non-U related events. This algorithm or function f2 may be expressed as follows:

$$f2(X) \Pi Z \text{ and } (f2(X) \Pi Y \text{ or } f2(X) \Pi U$$

Preferably, f2, like f1, is developed using the algorithm development process referenced above. f2, however, is developed and validated under conditions where U or Y, whichever the case may be, is not present. Thus, the gold standard data used to create f2 is data relating to Z only measured using highly accurate medical grade lab equipment.

Thus, according to this aspect of the invention, two functions will have been created, one of which, f1, is sensitive to U or Y, the other of which, f2, is insensitive to U or Y. As will be appreciated, there is a relationship between f1 and f2 that will yield either U or Y, whichever the case may be. In other words, there is a function f3 such that f3 (f1, f2)=U or f3 (f1, f2)=Y. For example, U or Y may be obtained by subtracting the data produced by the two functions (U=f1−f2 or Y=f1−f2). In the case where U, rather than Y, is determined from the relationship between f1 and f2, the next step involves obtaining Y from U based on the relationship between Y and U. For example, Y may be some fixed percentage of U such that Y can be obtained by dividing U by some factor.

One skilled in the art will appreciate that in the present invention, more than two such functions, e.g. (f1, f2, f3, . . . f_n−1) could be combined by a last function f_n in the manner described above. In general, this aspect of the invention requires that a set of functions is combined whose outputs vary from one another in a way that is indicative of the parameter of interest. It will also be appreciated that conditional dependence or independence as used here will be defined to be approximate rather than precise. For example, it is known that total body metabolism is measured as total energy expenditure, or TEE, according to the following equation:

$$TEE=BMR+AE+TEF+AT,$$

wherein BMR is basal metabolic rate, which is the energy expended by the body during rest such as sleep, AE is activity energy expenditure, which is the energy expended during physical activity, TEF is thermic effect of food, which is the energy expended while digesting and processing the food that is eaten, and AT is adaptive thermogenesis, which is a mechanism by which the body modifies its metabolism to extreme temperatures. It is estimated that it costs humans about 10% of the value of food that is eaten to process the food. TEF is therefore estimated to be 10% of the total calories consumed. Thus, a reliable and practical method of measuring TEF would enable caloric consumption to be measured without the need to manually track or record food related information. Specifically, once TEF is measured, caloric consumption can be accurately estimated by dividing TEF by 0.1 (TEF=0.1*Calories Consumed; Calories Consumed=TEF/0.1).

According to a specific embodiment of the present invention relating to the automatic measurement of a state parameter Y as described above, a sensor device as described above may be used to automatically measure and/or record calories consumed by an individual. In this embodiment, the state parameter Y is calories consumed by the individual and the indicator U is TEF. First, the sensor device is used to create f1, which is an algorithm for predicting TEE. f1 is developed and validated on subjects who ate food, in other words, subjects who were performing activity and who were experiencing a TEF effect. As such, f1 is referred to as EE(gorge) to represent that it predicts energy expenditure including eating effects. The verifiable standard data used to create f1 is a VO2 machine. The function f1, which predicts TEE, is conditionally dependent on and predicts the item U of interest, which is TEF. In addition, f1 is conditionally dependent on and predicts Z which, in this case, is BMR+AE+AT. Next, the sensor device is used to create f2, which is an algorithm for predicting all aspects of TEE except for TEF. f2 is developed and validated on subjects who fasted for a period of time prior to the collection of data, preferably 4-6 hours, to ensure that TEF was not present and was not a factor. Such subjects will be performing physical activity without any TEF effect. As a result, f2 is conditionally dependent to and predicts BMR+AE+AT but is conditionally independent of and does not predict TEF. As such, f2 is referred to as EE(fast) to represent that it predicts energy expenditure not including eating effects. Thus, f1 so developed will be sensitive to TEF and f2 so developed will be insensitive to TEF. As will be appreciated, in this embodiment, the relationship between f1 and f2 that will yield the indicator U, which in this case is TEF, is subtraction. In other words, EE (gorge)–EE (fast)=TEF.

In the most preferred embodiment, armband body monitoring device 300 includes and/or is in communication with a body motion sensor such as an accelerometer adapted to generate data indicative of motion, a skin conductance sensor such as a GSR sensor adapted to generate data indicative of the resistance of the individual's skin to electrical current, a heat flux sensor adapted to generate data indicative of heat flow off the body, a electrodes for generating an ECG signal from which data indicative of the rate or other characteristics of the heart beats of the individual may be generated, and a temperature sensor adapted to generate data indicative of a temperature of the individual's skin. In this preferred embodiment, these signals, in addition the demographic information about the wearer, make up the vector of signals from which the raw and derived channels X are derived. Most preferably, this vector of signals includes data indicative of motion, resistance of the individual's skin to electrical current, heat flow off the body, and heart rate.

Another specific instantiation where the present invention can be utilized relates to detecting when a person is fatigued. Such detection can either be performed in at least two ways. A first way involves accurately measuring parameters such as their caloric intake, hydration levels, sleep, stress, and energy expenditure levels using a sensor device and using the two function (f1 and f2) approach to provide an estimate of fatigue. A second way involves directly attempting to model fatigue using the direct derivational approach described in connection with FIGS. 11 and 12. The first way illustrates that complex algorithms that predict the wearer's physiologic state can themselves be used as inputs to other more complex algorithms. One potential application for such an embodiment of the present invention would be for first-responders, e.g. firefighters, police, soldiers, where the wearer is subject to extreme conditions and performance matters significantly. For example, if heat flux is too low for too long a period of time but skin temperature continues to rise, the wearer is likely to experience severe heat distress. Additionally, the ability to detect the wearer's hydration level and the impact of the deterioration of that level is quite useful, and may be derived utilizing the multiple sensors and parameters detected by the system. When a person becomes dehydrated, they typically experience an initially high level of perspiration, which then drops off. The body loses its ability to cool, and heat flux changes are detected. Additionally, the body temperature rises. At this point the cardiovascular system becomes less efficient at transporting oxygen and heart rate increases to compensate, possibly as much as 10-20%, necessitating an increase in respiration. At later stages, the user experiences peripheral vascular shutdown which reduces blood pressure and results in degradation in activity, awareness and performance. The monitoring system, which would be capable of measuring and tracking the hydration level, works in conjunction with the ECG detection, which, by measuring the relative changes in amplitude over time, in conjunction with expended energy, will recognize and confirm that amplitude changes are unexpected, or expected because of the events to current time.

It will be appreciated that algorithms can use both calibrated sensor values and complex derived algorithms. This is effective in predicting endpoints to or thresholds of certain physiological conditions and informing the wearer or other observer of an approximate measure of time or other activity until the endpoint is likely to be reached.

Another application of the current invention is as a component in an apparatus for doing wearer fingerprinting and authentication. A 128-Hz heart-rate signal is a rich signal, and personal characteristics such as resting heart rate, beat to beat variability, response to stimuli, and fitness will show up in the signal. These identifying personal characteristics can be used to verify that the wearer is indeed the approved wearer for the device or to identify which of a range of possible approved wearers is currently wearing the device. In one embodiment of this aspect of the invention, only the 128-hz signal and derived parameters from that signal are utilized for identification. In another, all of the sensors in the monitor are used together as inputs for the identification algorithm.

In another application of this aspect of the invention, an authentication armband can be utilized in a military or first responder system as a component in a friend or foe recognition system.

Interaction with other devices is also contemplated. The system can augment the senses and also the intelligence of other products and computer systems. This allows the associated devices to collectively know more about their user and be able to react appropriately, such as automatically turning the thermostat in the house up or down when asleep or turning the lights on when awakened. In the entertainment context, the detection of certain stress and heart related parameters may be utilized to affect sound, light and other effects in a game, movie or other type of interactive entertainment. Additionally, the user's condition may be utilized to alter musical programming, such as to increase the tempo of the music coincident with the changing heart rate of the user during exercise or meditation. Further examples include turning the car radio down when the person gets stressed while they drive because they're looking for an address; causing an appliance to prepare a caffeinated drink when the person is tired; matching up people in a social environment in the same mood or with the same tastes; utilizing alertness and stress indicators to tune teaching systems such as intelligent tutors or flight simulators, to maximize the student's progress; removing a person's privileges or giving a person privileges based on their body state, for example not letting a trucker start up his truck again until he has had 8 hours of sleep; providing automatic login to systems such as the wearer's personal computer based on biometric fingerprinting; and creating new user interfaces guided in part or in whole by gross body states for impaired individuals such as autistic children.

Moreover, new human-computer interactions can be envisioned that use bio-states to adjust how the computer reacts to the person. For example, a person is tele-operating a robotic arm. The system can see he is tired and so smoothes out some of his motion to adjust for some expected jerkiness due to his fatigue.

Individuals with suspected heart rhythm irregularities will often undergo some type of home or ambulatory ECG monitoring. Quite often, the individual's symptoms appear infrequently and irregularly, such as one a day, once a week, once a month, or even less often. In such cases, it is unlikely that the symptoms will be detected during a visit to the doctor in which classic ECG measurements are taken. Thus the need for home or ambulatory ECG monitoring to attempt to capture such infrequent episodes. The most common home or ambulatory ECG monitoring methods are Holter monitoring, event recording, and continuous loop recording, as described above.

Figure 12A:
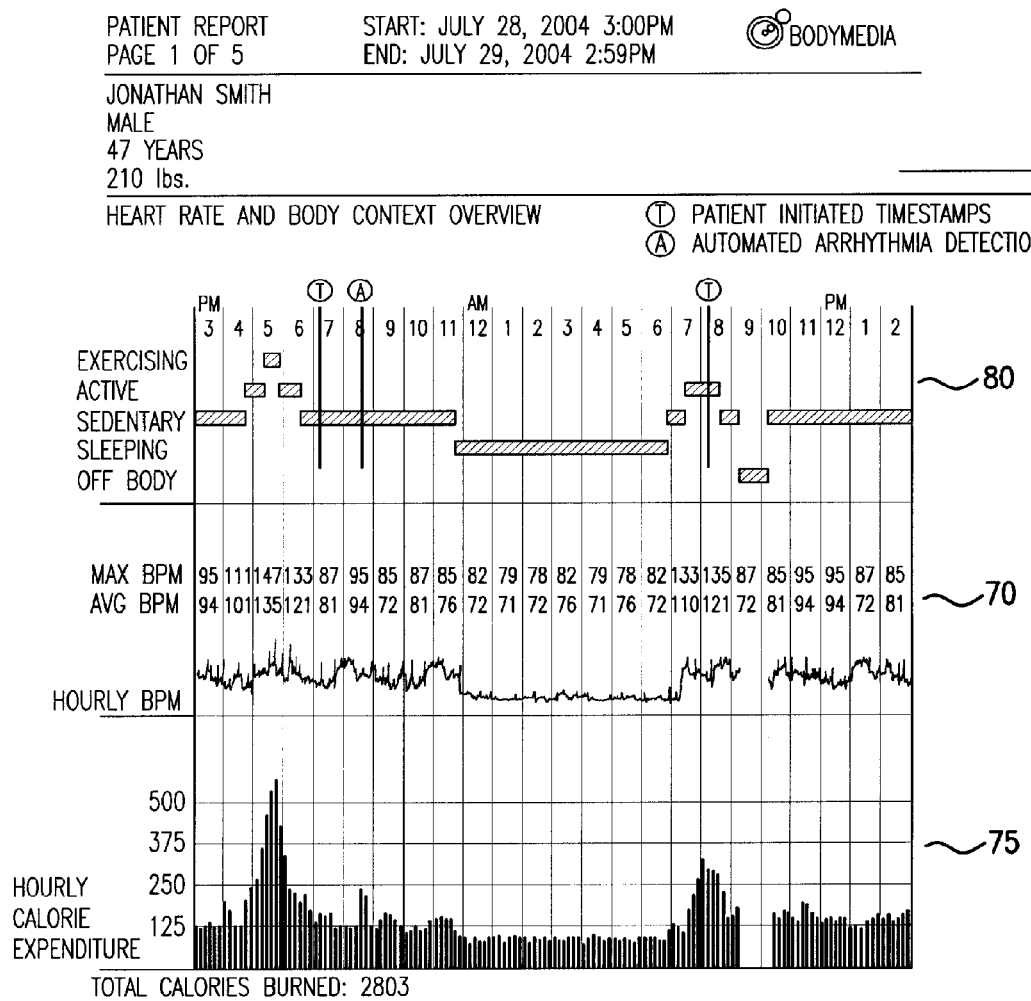

According to another aspect of the present invention, a device as described herein that measures an ECG signal may be adapted and configured to perform the functionality of a Holter monitor, an event recorder, or a continuous loop recorder. Preferably, such a device may be armband body monitoring device 300 as illustrated and described herein. Such a device may be comfortably worn for extended periods of time, unlike a Holter monitor or an event recorder on a convenient location on a limb, such as the upper arm in the case of armband body monitoring device 300. In addition, the recorded ECG signals may be combined with other data that is contemporaneously measured by such a device in accordance with other aspects of the present invention described herein, including the various physiological parameters and/or contexts that may be predicted and measured using the algorithms described herein, to provide automatically context and/or parameter annotated heart related information. For example, as shown in FIG. 12A, a measured ECG signal 70 for a period of time may be mapped or presented along with measured parameters such as energy expenditure 75 or even raw sensor values and detected contexts 80 such as walking, driving and resting for the same period of time. This annotated view of the ECG signal would be useful to a health care provider because it will identify what the individual was doing while certain heart symptoms were occurring and will provide certain other physiological parameters that may assist with diagnosis and treatment. This may be accomplished, for example, by downloading the measured ECG signal, the measured parameter or parameters and the detected contexts to a computing device such as a PC which in turn creates an appropriate display.

It is also well known that there is a circadian pattern to certain arrhythmias or conditions which lead to heart related stress. Sudden cardiac arrest, for example, has a high incidence in early morning. It is therefore anticipated that the detection might be enhanced during certain time periods, or that other devices could be cued by the monitoring system to avoid certain coincident or inappropriate activities or interactions. A pacemaker, for example could raise pace according to a preset protocol as the wearer comes out of sleep or waking the user calmly at the end of a REM stage of sleep.

The system is further applicable in diagnostic settings, such as the calibration of drug therapies, post-surgical or rehabilitative environments or drug delivery monitoring, with immediate and real time effects of these medical applications and procedures being monitored continuously and non-invasively.

This type of application may also be utilized in a mass emergency or other crisis situation, with victims being collected in one location (for example a gymnasium) and are being seen by nurses, EMTs, physicians, volunteers—where this staff is basically short staffed for this type of situation and diagnosing or keeping watchful monitoring over all the victims now patients (some quite injured and others under observation in case the injury or shock are delayed in terms of physical/tactile/visual symptoms). A system having diagnostic heart related capabilities and, optionally, hydration, hypothermia, stress or shock could be distributed upon each victim's entrance for monitoring. The design of the system, which alleviates the need to remove most clothing for monitoring, would both speed and ease the ability of the caregivers to apply the devices. This system could send the alerts to a central system in the facility where the serial number is highlighted, and the attendant is alerted that a condition has been triggered, the nature of the condition as well as the priority. Within this collaborative armband scenario, all the armbands around the condition sensing/triggering armband could also beep or signal differently to focus the attention of an attendant to that direction more easily. Additionally, certain techniques, as described below, would allow all of the armbands to interactively coordinate and validate their relative location continuously with the surrounding armbands, allowing the central monitoring station to locate where in the facility the location of any particular armband is located and where specifically are the individuals who need the most immediate attention.

More specifically, the device could be designed to be part of a network of devices solving as a network of devices the exact or relative locations of each device in the network. In this embodiment each device would have one or more mechanisms for determining the relative position of itself to another device in the network. Examples of how this could be done include the sending of RF, IR, or acoustic signals between the devices and using some technique such as time of flight and/or phase shifts to determine the distance between the devices. It is a known problem that methods such as these are prone to errors under real world circumstances and in some cases, such as the phase shift method, give the receiving device an infinite number of periodic solutions to the relative distance question. It is also typical that such devices, because of power limitations, occasional interference from the environment and the like, would lose and then later regain contact with other devices in the networks so that at any one time each device might only have communication with a subset of the other devices in the network.

Given this ability to establish at each moment in time a relative distance between each pair of devices, and the ability of the devices to share what they know with all other devices in the network, for a network for N devices, there are a total of $(N*(N-1))/2$ distances to be measured and it is practical that every device could, by passing on all they know to all the devices they can communicate with at that moment in time, arrive at a state where all devices in the network have all available relative distances that could be measured, which would be some subset of the $(N*(N-1))/2$ possible distances to be measured, and could have updates to this list of numbers quite often, e.g. several times per minute, relative to the speed at which the wearers are changing relative to each other.

Once each device has a list of these distances, each device effectively has a system of equations and unknowns. For example: A is approximately X meters from B, B is approximately Y meters from C, C is approximately Z meters from A, A is U meters from D, B is T meters from D, C is V meters from D. Alternatively, under the phase shift only model, these equations could be as follows: A is some integer multiple of six inches from B, B is some integer multiple of eight inches from C, C is some integer multiple of one foot from D, and D is some integer multiple of seven inches from A. To the extent there is redundant information in the network, as in the examples just given, and with the possible additional assumptions about the topology on which the wearers are situated, such as a flat area, a hill that rises/falls no faster than a grade of 6% or the like, each device can solve this system of equations and unknowns or equations and inaccurate values to significantly refine the estimates of the distance between each pair of devices. These results can be then shared between devices so that all devices have the most accurate, up-to-date information and all agree, at each moment in time, what their relative positions are. This solving of equations can be done through a process such as dynamic programming or a matrix solution form such as singular value decomposition. The previous values each wearer's device has for its distance to all the other devices can be included in these calculations as follows to take advantage for things such as if A was ten feet from B five seconds ago, it is highly unlikely that A is now two hundred feet from B even if that is one of the possible solutions to the system of equations and unknowns.

An alternative embodiment involves utilizing probabilistic reasoning to keep track of a probabilistic estimate of the relative location of each wearer and for taking into account possible sensor noise and expected motion. Kalman filters are an example of this sort of reasoning often applied in tracking a single moving entity; extensions to multiple interacting entities are available.

If these devices are also equipped with ability to know or be told, from time to time, their actual or approximate global location, such as through an embedded GPS chip, then this information could also be shared with all the other devices in the network so that, adjusting for their relative distances, each device will then know its global location.

To aid in this process, it is preferred that there be provided at least one interval where the relative positions are known for the entire network. This, along with frequent updates, relative to the rate they move relative to each other, to the relative distances of the devices, reduces the possibly solutions for these systems of equations and thereby improves the accuracy of the process. This synchronization of the devices could be accomplished for example, for having them together in the identical location for a moment before each devices sets out on its own for a time.

Figure 13:
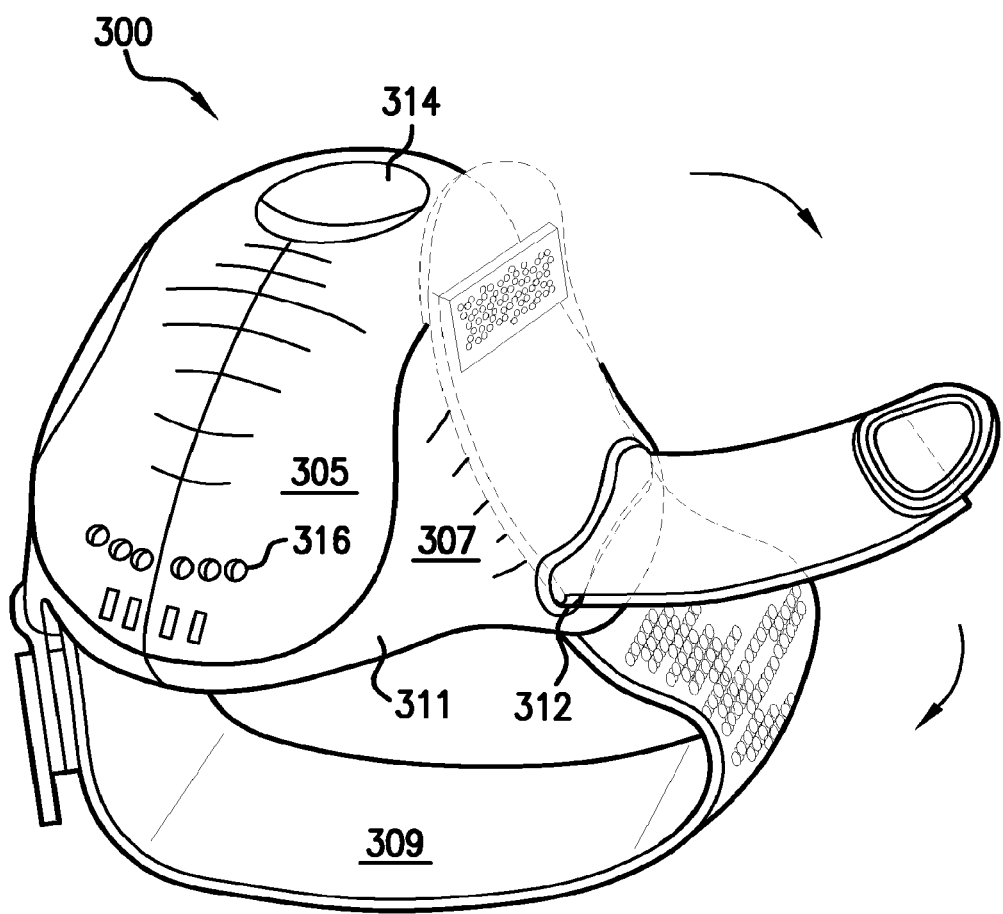
FIG. 13 is an isometric view of an armband body monitoring device.

Referring to FIG. 13, specific embodiment of a sensor device is shown which is in the form of an armband adapted to be worn by an individual on his or her upper arm, between the shoulder and the elbow, which, for convenience, be referred to as armband body monitoring device 300. Armband sensor device 300 includes housing 305, flexible wing body 307, and, elastic strap 309. Housing 305 and flexible wing body 307 are preferably made of a flexible urethane material or an elastomeric material such as rubber or a rubber-silicone blend by a molding process. Flexible wing body 307 includes first and second wings 311 each having a thru-hole 312 located near the ends thereof. First and second wings 311 are adapted to wrap around a portion of the wearer's upper arm.

Elastic strap 309 is used to removably affix armband body monitoring device 300 to the individual's upper arm. The surface of elastic strap is provided with velcro loops along a portion thereof. Each end of elastic strap 309 is provided with a velcro hook patch on the bottom surface and a pull tab. A portion of each pull tab extends beyond the edge of each end 427.

An activation button 314 is provided for appropriate user input, while LED output indicators 316 provide context-sensitive output. In particular, circuit 200 is provided inside housing 305 of armband body monitoring device 300, and the various electrodes and sensors identified herein are electrically connected thereto, as will be apparent to one skilled in the art. CPU 165 of circuit 200 would, in this embodiment, preferably be the processing unit forming part of the armband body monitoring device circuitry described in U.S. Pat. No. 6,605,038 and U.S. application Ser. No. 10/682,293, the specifications of both which are hereby incorporated by reference.

Figure 14:
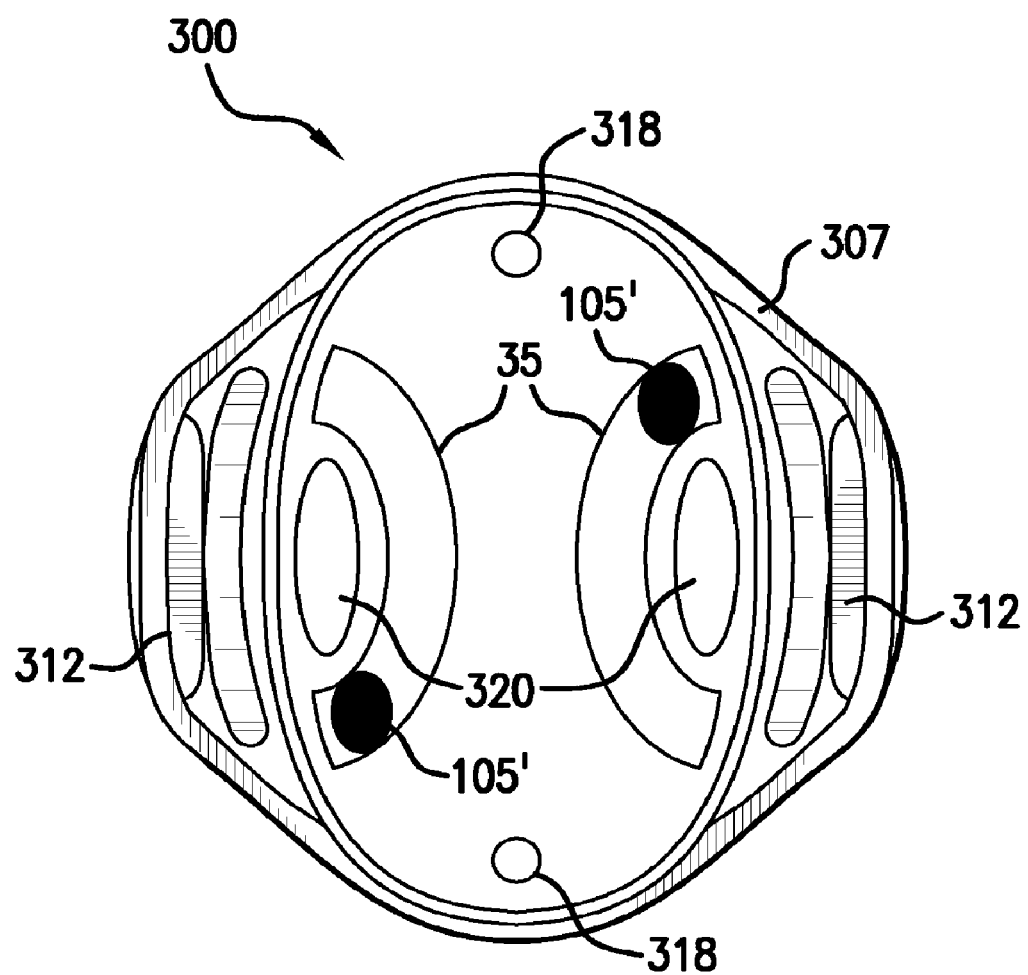
FIG. 14 is a bottom plan view of one embodiment of the armband body monitoring device.
Figure 15:
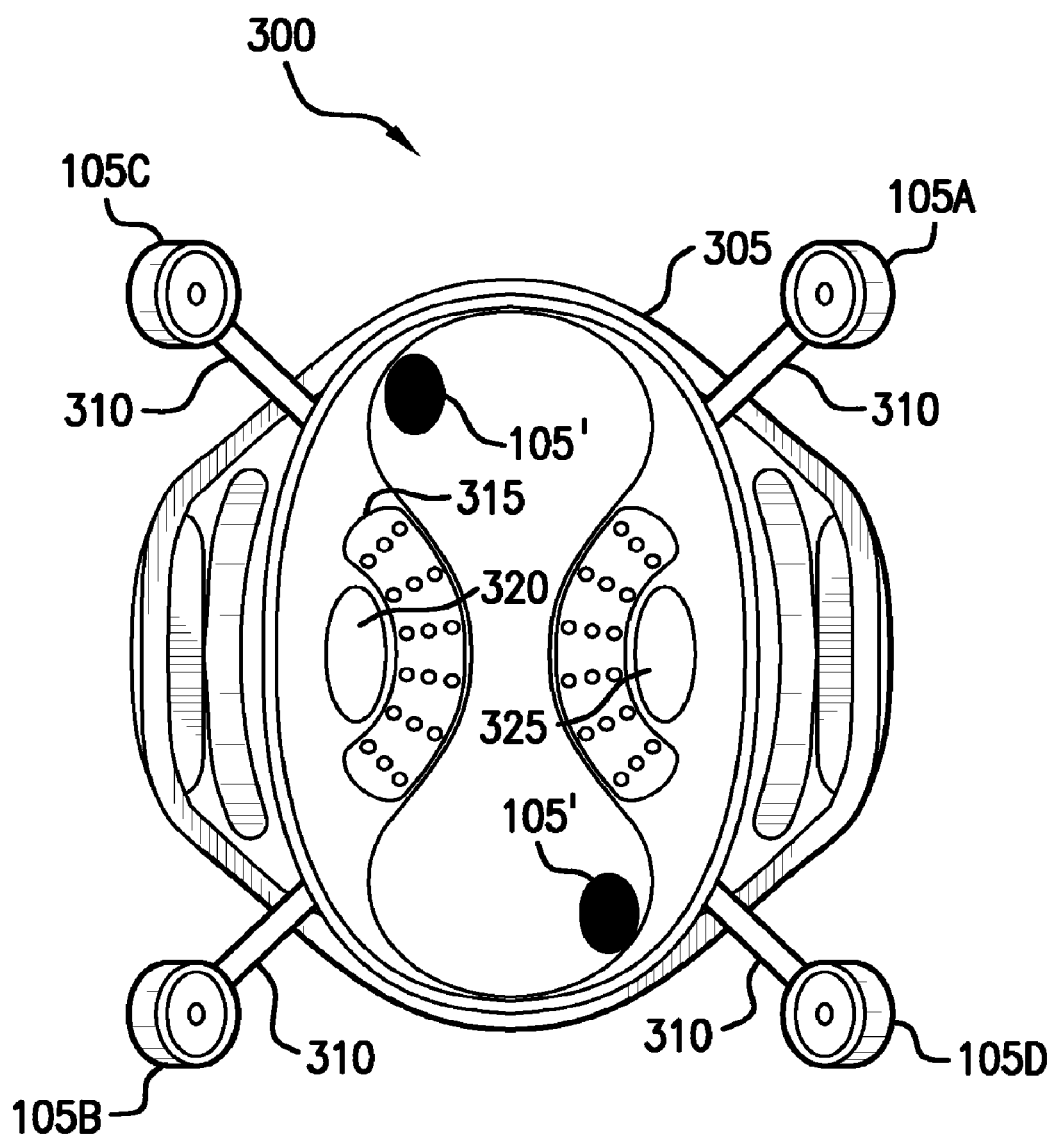
FIG. 15 is a bottom plan view of a second embodiment of the armband body monitoring device.
Figure 18:
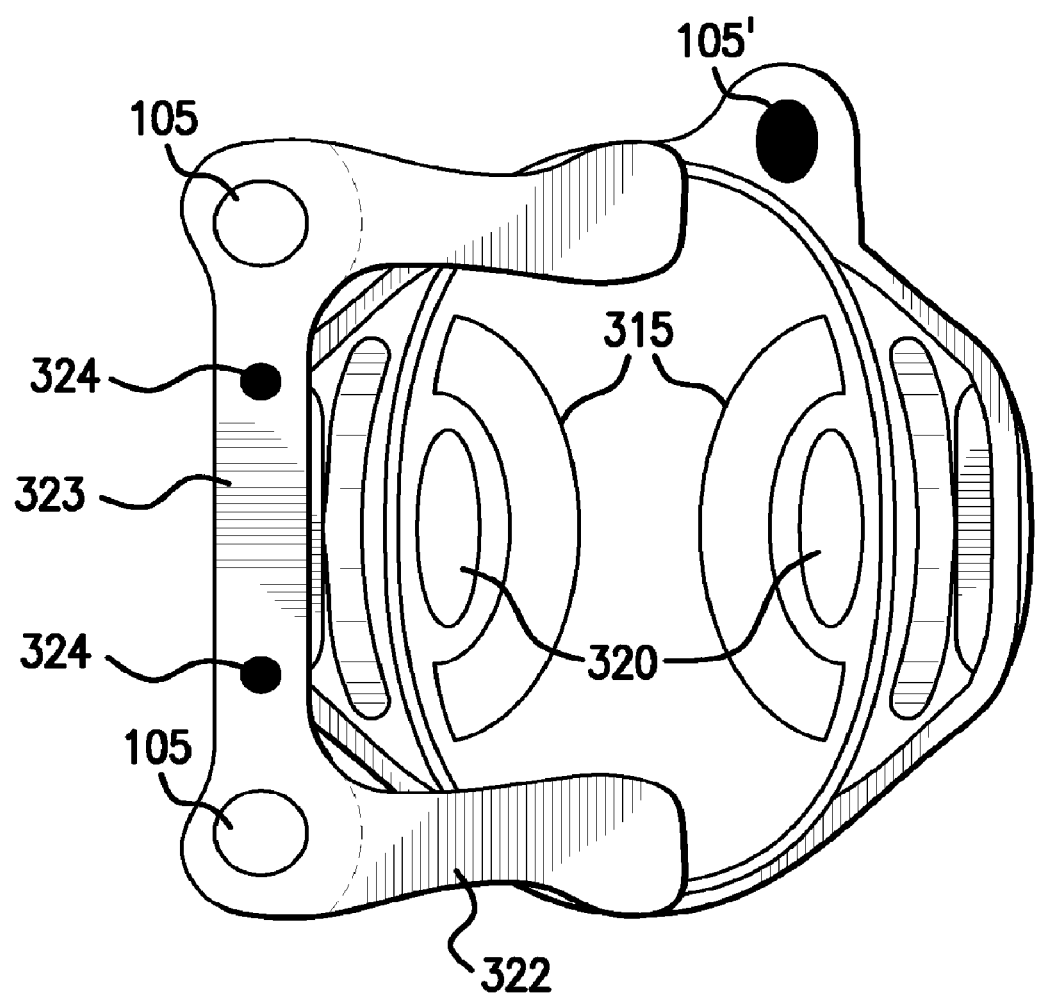
FIG. 18 is a bottom plan view of a fifth embodiment of the armband body monitoring device.

Referring now to FIGS. 14 and 15, armband body monitoring device 300 is provided with additional physiological and/or contextual sensors for sensing various physiological and/or contextual parameters of the wearer, including, but not limited to, GSR sensors 315 for measuring the resistance of the skin to electrical current, a heat flux sensor in thermal communication with heat flux skin interface component 320 for measuring heat flow off of the body, a skin temperature sensor in thermal communication with skin temperature skin interface component 325 for measuring skin temperature, a body motion sensor such as an accelerometer (not shown) for measuring data relating to body movement, and an ambient temperature sensor (not shown) for measuring the near-body temperature of the wearer. Referring to FIG. 14, at least one, and preferably two electrode support connectors 318 are provided for the temporary and removable attachment of any one of a series of electrode support modules. Referring to FIG. 15, circuit 200 including electrodes 105A through 105D may be provided as part of an armband body monitoring device 300 such as are described in the aforementioned U.S. Pat. No. 6,605,038 and U.S. application Ser. No. 10/682,293, owned by the assignee of the present invention (see, e.g., sensor devices 400, 800 and 1201 described in the '038 patent and/or the '293 application), connected to housing 305 and circuit 200 through insulated wires 310. Electrodes 105' are illustrated in FIGS. 14, 15 and 18 at alternative locations at various locations on the housing or support members. It is to be specifically noted that electrodes may be placed at any appropriate location on or associated with the housing for the purpose of engaging the corresponding appropriate locations on the body for detecting a signal of appropriate strength and aspect. With respect to FIG. 14, the alternative electrodes 105' are located within GSR sensors 315. With respect to FIG. 15, alternative electrodes 105' are mounted directly within housing 305.

Armband body monitoring device 300 is designed to be worn on the back of the upper arm, in particular on the triceps muscle of the upper arm, most preferably the left arm. Referring to the specific embodiment shown in FIG. 15, when worn on the upper left arm, electrode 105A is in contact with the deltoid muscle, electrode 105B is in contact with the triceps muscle, electrode 105C and electrode 105D are in contact with an area of the muscle which may not produce a detectable heart related signal but permits the detection of baseline EMG noise. Preferably, first and second imaginary diagonal lines connect electrode 105A to electrode 105B and electrode 105C to electrode 105D, respectively, at angles of approximately 31 degrees from vertical. In this embodiment, electrodes 105A and 105B may be paired with one another to detect a first signal and electrodes 105C and 105D may be paired with one another to detect a second signal as described above, which signals are summed together by summation circuit 170 of circuit 200.

Figure 16:
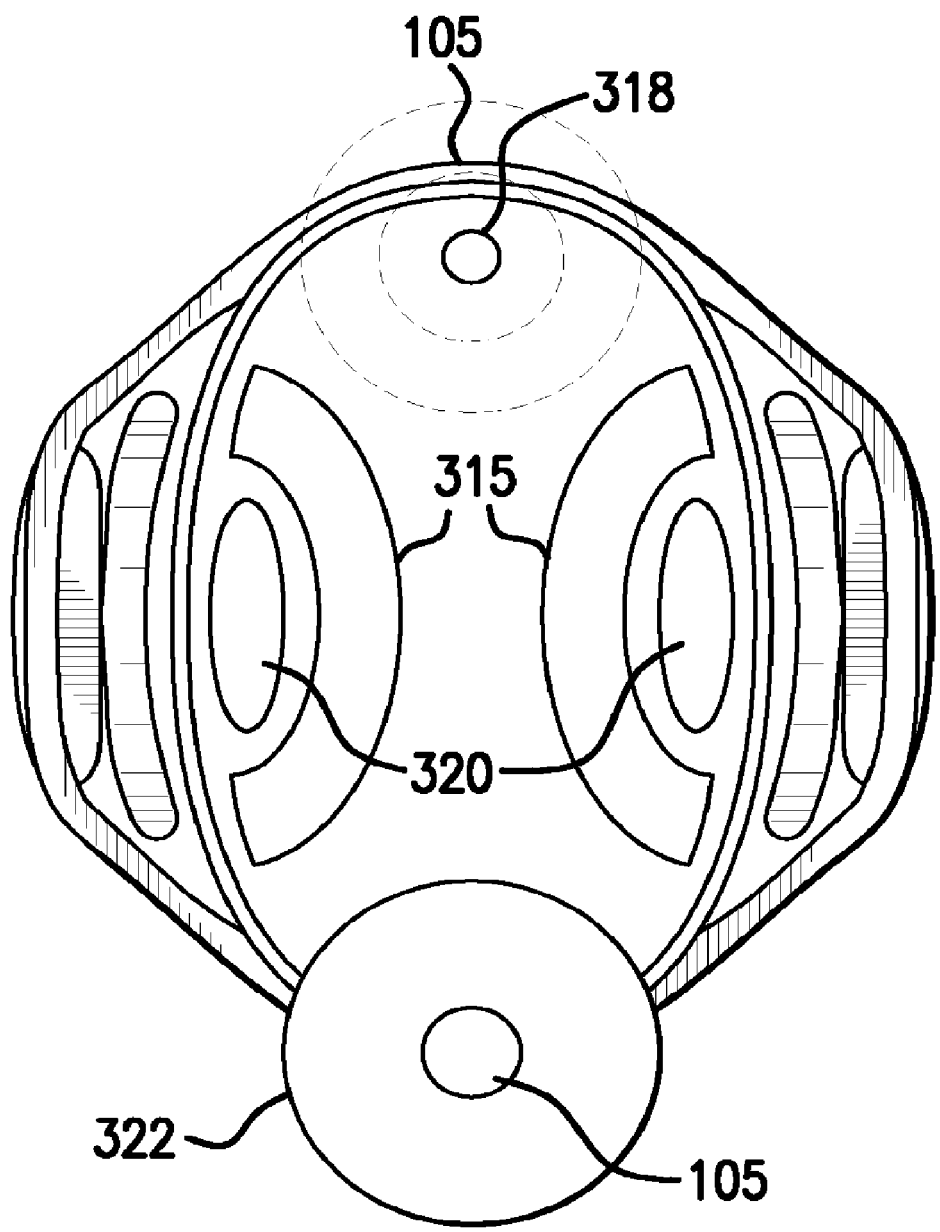
FIG. 16 is a bottom plan view of a third embodiment of the armband body monitoring device.

Referring now to FIG. 16, an alternative embodiment of the device illustrated in FIG. 15 is shown. Electrode support connector 318 is provided for the purpose of physically supporting a sensor or sensor support housing as well as establishing electrical communication therewith. Electrode support connector 318 may be a plug-in or snap-in connector of the pin type which will provide good physical support while allowing some degree of movement or rotation of the sensor or sensor housing while mounted on the body. Preferably, the device and sensor or sensor support, as appropriate, are integrated for best physical and electrical connection. A multichannel electrical connection is also provided according to conventional means, typically utilizing multiple independently insulated segments of the supporting connector. A sensor support housing 322 may be provided for the support and positioning of electrode 105, as shown in FIG. 16, or the electrode 105 or other sensor may be directly and independently mounted to electrode support connector 318. In this embodiment, the support housing 322, is entirely substituted by the electrode 105 itself in an identical physical arrangement. The electrode 105 may be positioned at any point on the surface of support housing 322, and need not be located at the center, as shown in FIG. 16. Additionally, sensors need not be a point source of information, as they are conventionally applied and utilized. The sensor may further be comprised of a broad segment of sensitive material which covers a substantial portion of the housing surface in order to maximize the location of the appropriate point for signal detection within the surface area of the sensor. In the event that a support housing 322 is utilized, a flexible material is utilized to permit the housing to conform to the surface of the arm upon which it is mounted to ensure good contact with the skin and underlying tissue. This is equally applicable to the embodiment shown in FIG. 15. It is also to be specifically noted that each of the sensor, electrode and support housing embodiments described and illustrated herein are interchangeable, with certain shapes or other physical parameters being selected for particular applications. Additionally, it is to be understood that the number and arrangement of the sensors, electrodes and support housings are not limited by the embodiments shown in the Figures, but may be interchanged as well. Lastly, in order to establish a particular geometry of sensors, electrodes or an array of the same, the housing 305 of the device may be modified to be elongated or diminished in any particular dimension for the purpose of improving the signal, as described above.

Figure 17:
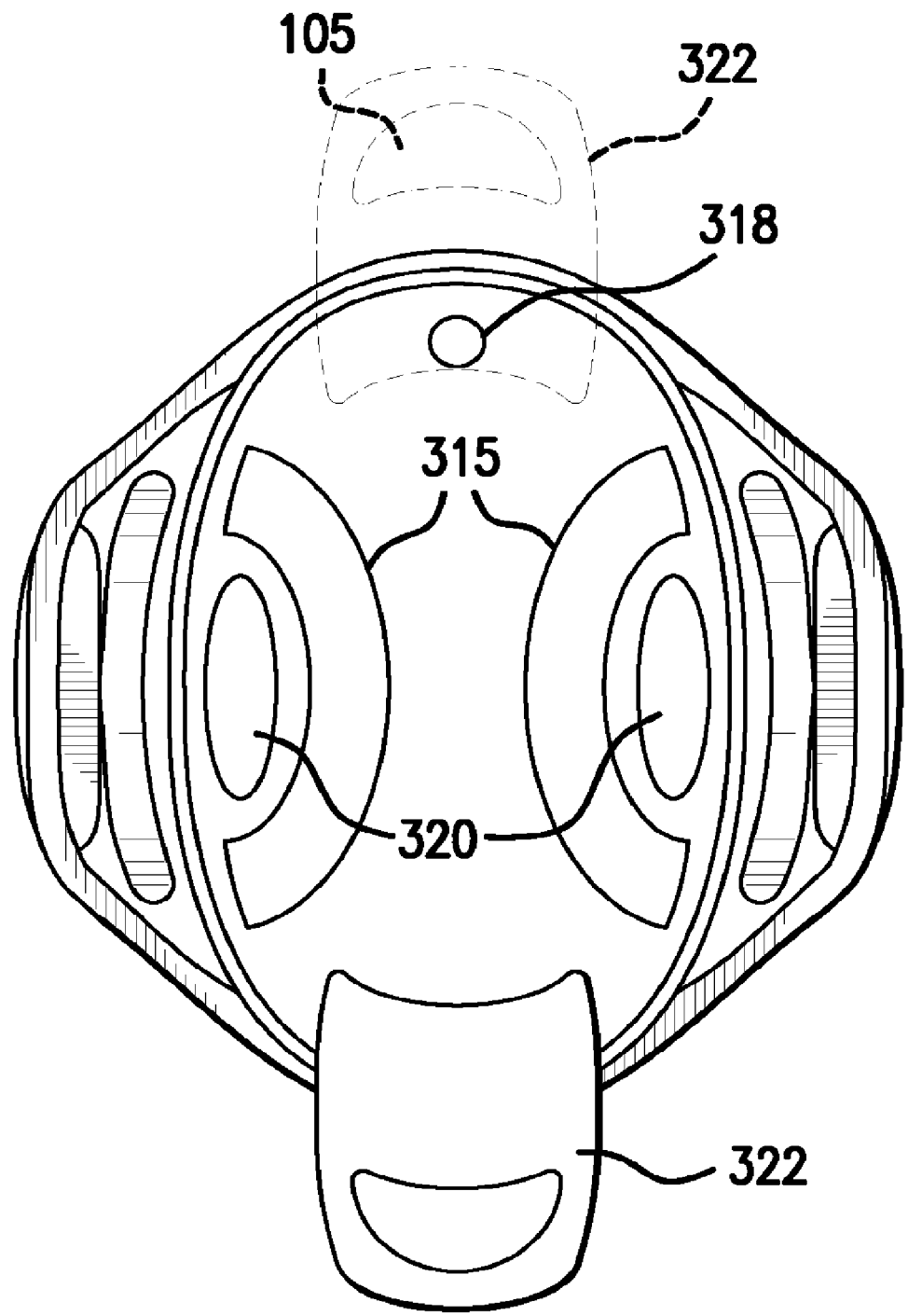
FIG. 17 is a bottom plan view of a fourth embodiment of the armband body monitoring device.

With reference to FIG. 17, an additional alternative embodiment is illustrated which provides a similar orientation of electrodes as that illustrated in FIG. 16, with the support housing 322 having a more elongated geometry. Typically, more elongated or outboard electrode placements will necessitate the use of more firm materials for the support housing 322, in order to maintain good skin contact. It is to be specifically noted that any of the housing embodiments shown and illustrated may further comprise a flexible or partly flexible housing section which is pre-molded in a curved embodiment in order to exert pressure against the skin.

FIG. 18 illustrates an asymmetrical arrangement of the support housing 322 having a lateral support arm 323 which is intended to specifically place the upper and lower electrodes 105 adjacent to the deltoid and brachialis sections of the tricep muscle, respectively, of the human upper arm. Lateral support arm 323 may also be separated from support housing 322 along the chain line sections indicated in the figure and affixed to wings 311 by restraints 324. Housing 305 or wings 311 may further be extended beyond the generally ovoid shape illustrated in the figures hereto into any particular shape necessary to engage the appropriate locations on the body. More particularly, irregular extensions of housing 305 or wings 311 are contemplated to mount alternative electrodes 105'.

Figure 19:
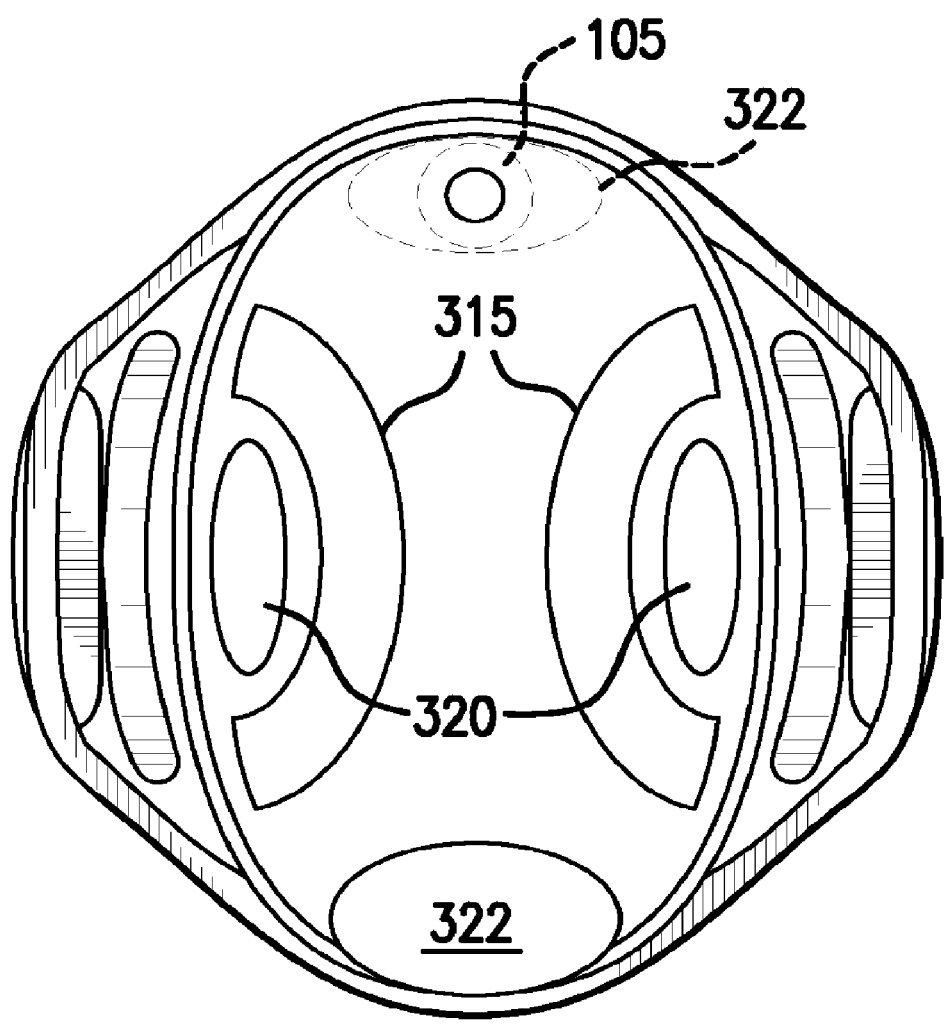
FIG. 19 is a bottom plan view of a sixth embodiment of the armband body monitoring device.

FIG. 19 illustrates support housing 322 having a particular ovoid shape.

Figure 20:
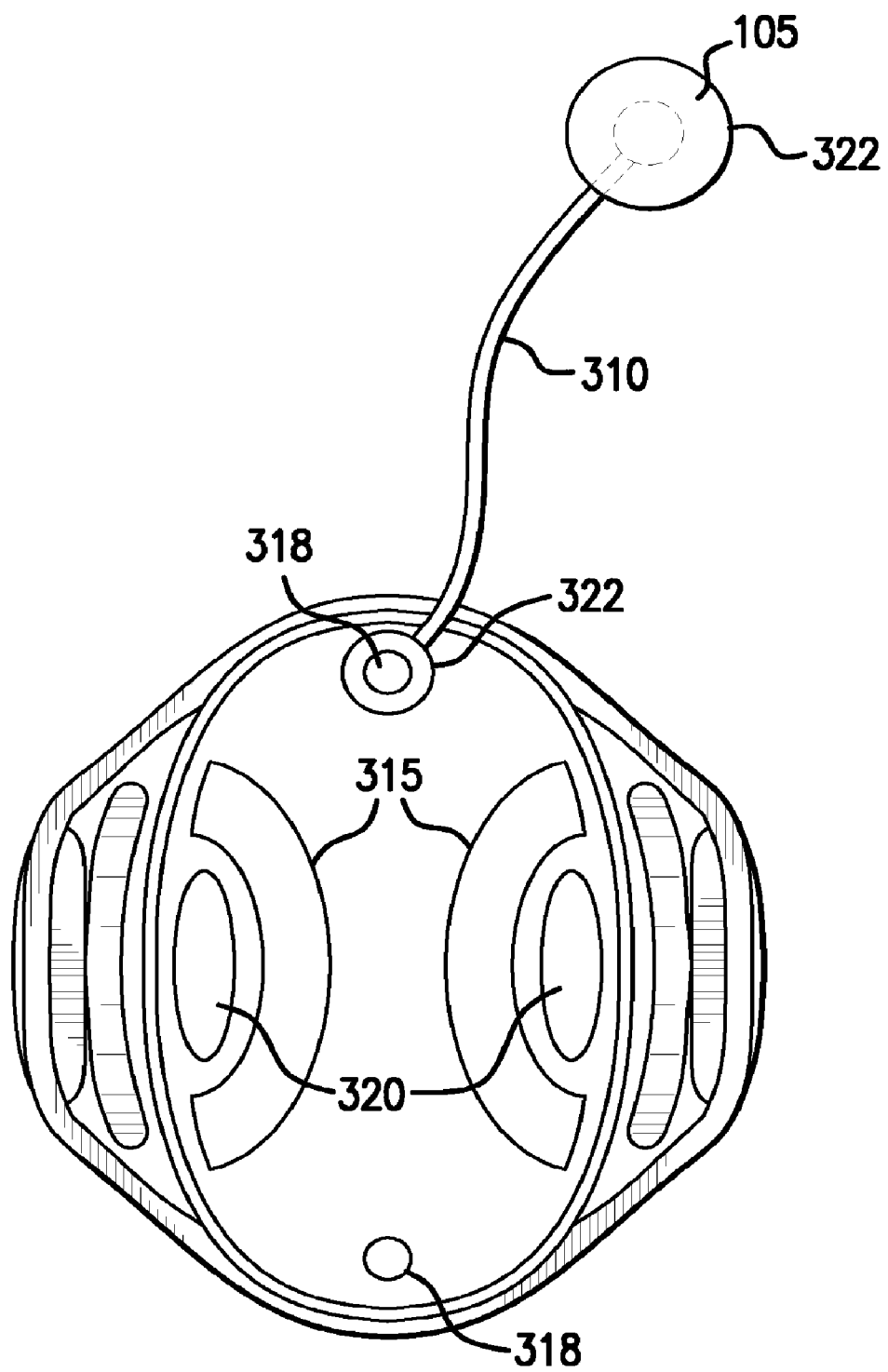
FIG. 20 is a bottom plan view of a seventh embodiment of the armband body monitoring device.
Figure 21:
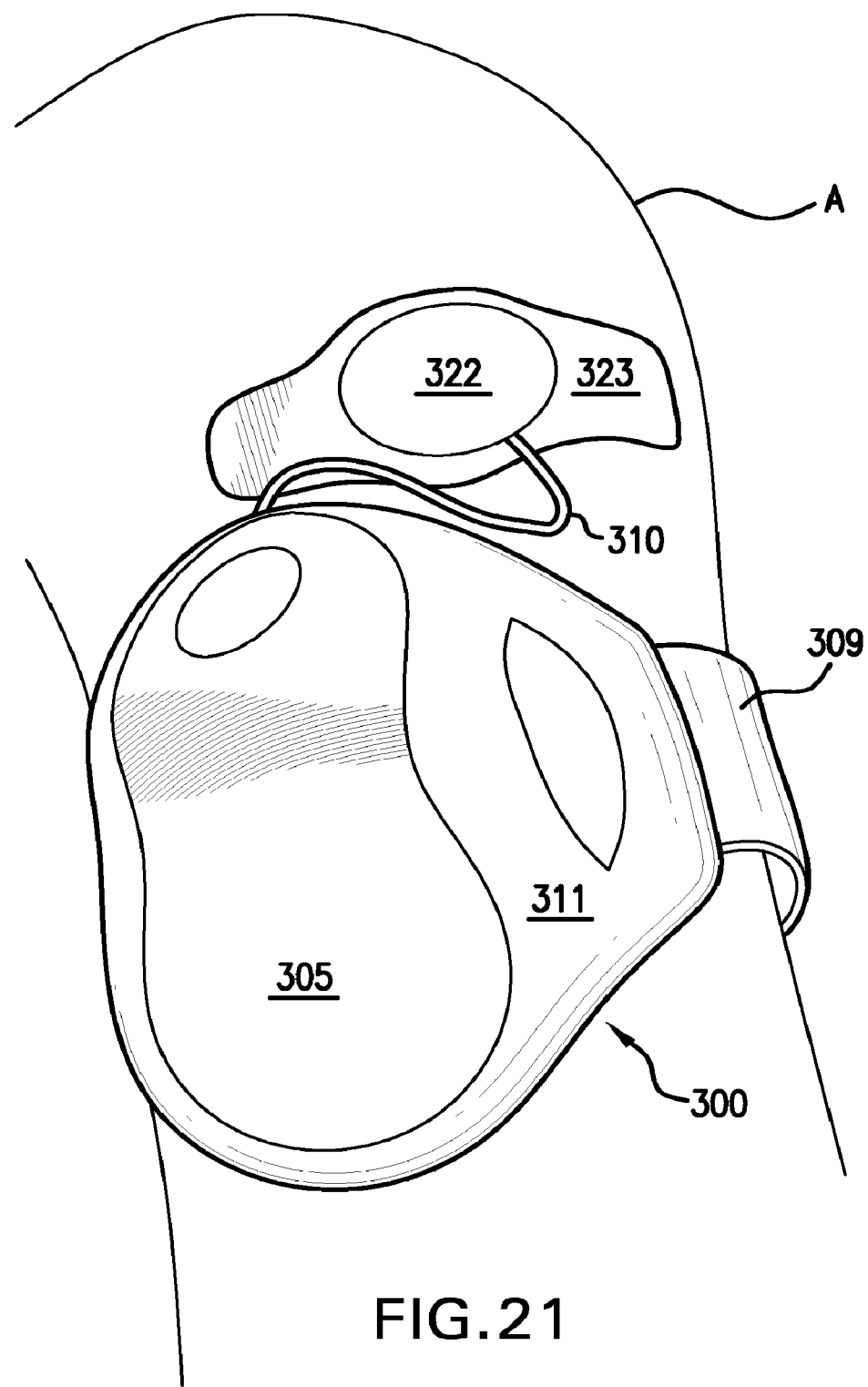
FIG. 21 is an isometric view of the seventh embodiment of the armband body monitoring device mounted upon a human arm.

FIG. 20 illustrates an alternative embodiment similar to that illustrated in FIG. 15, however only one outboard or external electrode 105 is utilized, which is provided with electrical communication through insulated wire 310. Any of the previously identified electrode geometries may be utilized for affixation to the second electrode support connector 318. The use of the outboard electrode 105 connected to insulated wire 310, sometimes identified as a fly lead, is adapted for particular location on a remote section of the body which renders the creation of an integrated housing 305 of armband body monitoring device 300 impractical. FIG. 21 illustrates the embodiment of FIG. 20 mounted upon a human upper arm A. Armband body monitoring device 300 is placed adjacent the skin at an appropriate position and the elastic strap 309 encircles the arm and is pulled tight enough to firmly secure the housing without reducing blood flow. Sensor support housing 322 supports electrode 105 (not shown) and is held in place by adhesive support 323 which mounts support housing 322 to the skin. It is to be specifically noted that the location of the support housing is not limited to the location illustrated in FIG. 21, but may extend to any part of the body, including the other arm of the wearer. The most preferred embodiment seeks to minimize the use and length of insulated wires 310.

Figure 22:
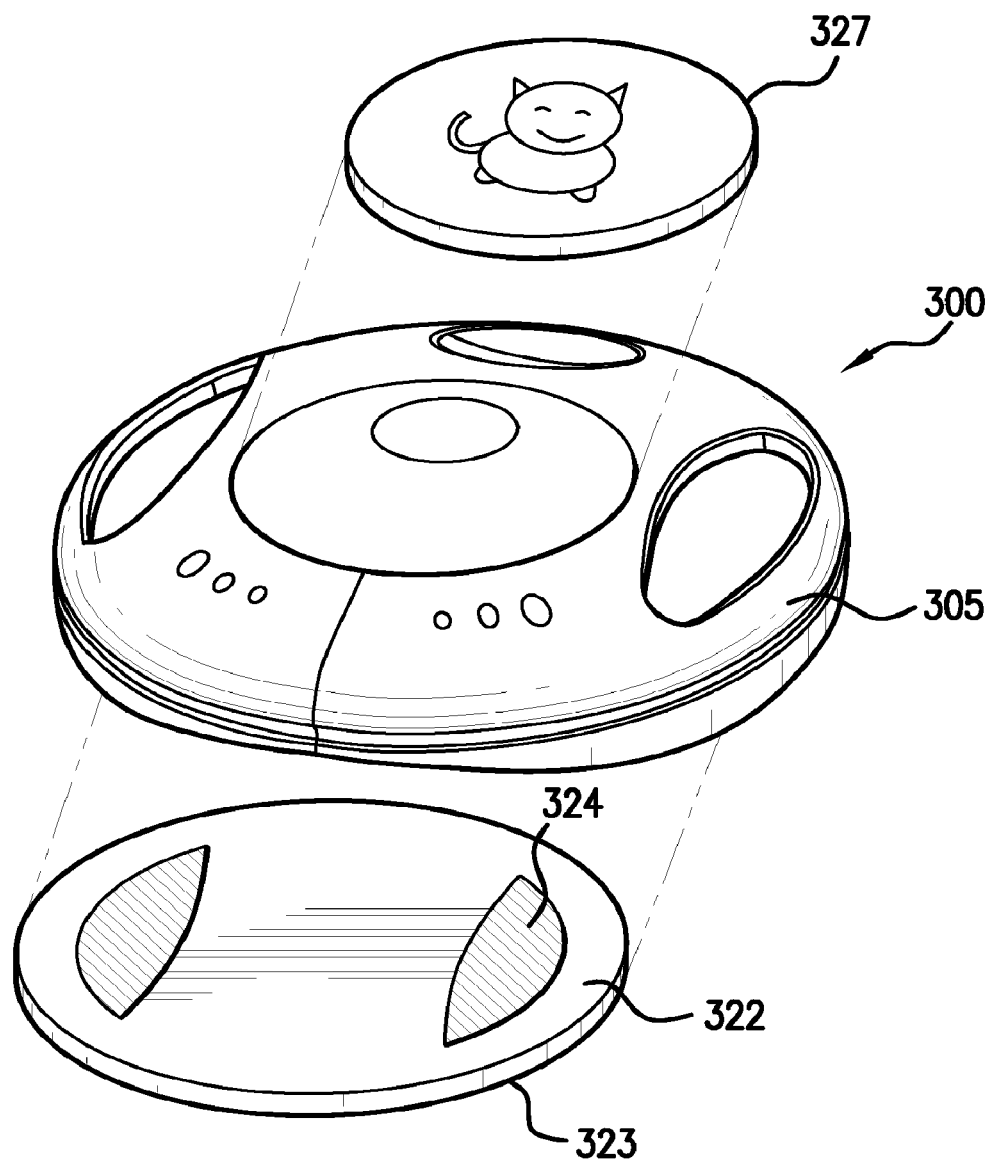
FIG. 22 is an isometric view of an eighth embodiment of the armband body monitoring device.

FIG. 22 illustrates an alternative embodiment which presents a more modular approach to the interface between the electrodes 105, support housing 322 and housing 305. Housing 305 is provided with a similar skin engagement face (not shown) as illustrated in FIG. 14. An integrated removable support housing 322, which may be disposable, comprises both the support material for exerting the appropriate force upon the electrodes (not shown) on the underside of the support housing 322 against the skin, the electrodes themselves, as well as the electronic connections between the electrodes and the housing 305. Support housing is provided with at least one electrode contact 324 for electronic engagement with the housing, and may be suited for engagement with either electrode support connectors 318 or GSR sensors 315 which have been specifically adapted to communicate with electrodes 105 in conjunction with support housing 324. An optional adhesive support 323 may also be provided on the underside of support housing 322. In an alternative embodiment, adhesive support 323 may provide the sole means for retention of housing 305 on the user's arm. Support housing 322 may also be supported on the skin solely by the force of the housing 305 as restrained on the arm by elastic strap 309, or in conjunction with other housing or garment support devices as described in U.S. patent application Ser. No. 10/227,575, the specification of which is incorporated by reference herein. An output screen 327 is illustrated herein on the upper surface of housing 305 for displaying certain performance or other status information to the user. It is to be specifically noted that the output screen may be of any type, including but not limited to an electrochemical or LCD screen, may be disposable, and may further be provided on any of the embodiments illustrated herein.

Figure 23C:
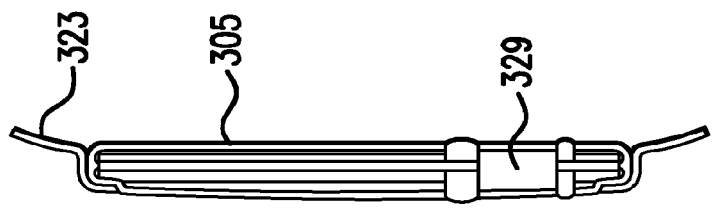
FIG. 23C is a sectional view of the embodiment of FIG. 23B taken along line A-A.
Figure 23B:
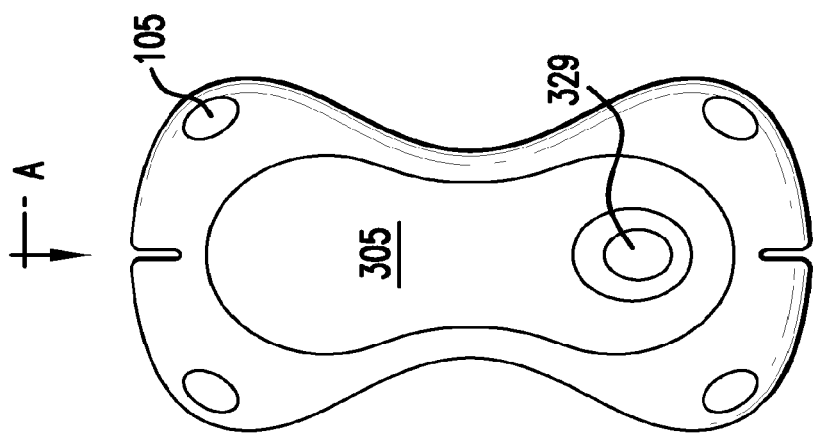
FIG. 23B is a bottom plan view of a ninth embodiment of the armband body monitoring device.
Figure 23A:
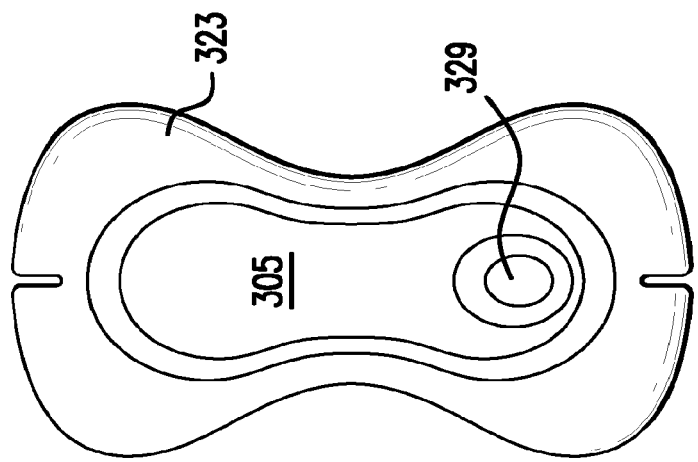
FIG. 23A is a top plan view of a ninth embodiment of the armband body monitoring device.

FIGS. 23A-C illustrate yet another embodiment of the device which incorporates a slimmer housing 305, which is provided with aperture 329 for functionality which is not relevant hereto. An adhesive support 323 is mounted semi-equatorially and may contain electrodes 105, which may also be mounted on the underside of housing 305. In operation, the housing is affixed to the body through the use of the adhesive provided on adhesive support 323, which maintains a consistent contact between housing 305 and/or electrodes 105 and/or any other relevant sensors contained within housing 305 and the body. It is to be specifically noted that this adhesive embodiment may be mounted at any point on the human body and is not limited to any particular appendage or location.

An additional aspect of the embodiments illustrated herein is the opportunity to select certain aspects of each device and place the same in disposable segments of the device, as illustrated with particularity in FIG. 22. This may be utilized in conjunction with a permanent, or durable housing 305 which contains the remaining aspects of the device's functionality. Additionally, the entire device could be rendered in a disposable format, which anticipates a limited continuous wearing time for each system. In this embodiment, as mentioned previously, the entire device might be rendered in a patch-like flexible housing, polymer, film, textile or other support envelope, all of which could be spring-like and which may be mounted anywhere on the body. This includes a textile material which has the electrodes and other electronics interwoven within the material itself, and which exerts sufficient force against the body to maintain appropriate contact for the reception of the signals. Fabrics such as Aracon, a metal clad textile with the strength characteristics of Kevlar, both manufactured by DuPont, are capable of carrying an electrical current or signal therethrough. ElekTex from Eleksen Ltd is a soft textile appropriate for use in clothing or bedding which contains electrodes and/or sensors which can detect movement or pressure. These fabrics could be utilized in combination with the device components in a wearable shirt or other garment which could both sense the appropriate signals as well as provide a network for the interconnection of the various electrical components which could be located at various convenient places within the garment.

The ECG wave form collected from inside any of the equivalence class regions will not necessarily have the shape of a standard ECG wave form. When this is the case, a mapping can be created between a ECG wave form taken within a single equivalence class region and ECG wave forms taken between equivalence class regions. This can be done using the algorithm development process described above, creating a function that warps the within equivalence class region to be clearer when displayed as a standard ECG wave form.

Although particular embodiments of the present invention have been illustrated in the accompanying drawings and described in the foregoing detailed description, it is to be further understood that the present invention is not to be limited to just the embodiments disclosed, but that they are capable of numerous rearrangements, modifications and substitutions, as identified in the following claims.

What is claimed is:

1. An apparatus to determine physiological status of an individual, comprising:
   a. a wearable sensor device adapted to be worn in an equivalence region of said individual's body;
   b. at least two electrodes attached to said wearable sensor device, said electrodes adapted to be mounted within said equivalence region and to detect a heart-related signal; and
   c. a processor in electronic communication with said at least two electrodes and programmed to determine a heart-related status parameter from said heart-related signal, and to determine said individual's physiological status based on said heart-related signal.

2. The apparatus of claim 1, further comprising at least one sensor mounted to said wearable sensor device, said at least one sensor selected from the group consisting of a heat flux sensor, a galvanic skin response sensor, a skin temperature sensor, and an accelerometer.

3. The apparatus of claim 2, wherein said processor is further programmed to determine said individual's physiological status from data detected by said at least one sensor.

4. The apparatus of claim 1, wherein said individual's physiological status is at least one of fatigue, heat distress, dehydration, shock, and peripheral vascular shutdown.

5. The apparatus of claim 2, wherein said individual's physiological status is at least one of fatigue, heat distress, dehydration, hypothermia, and peripheral vascular shutdown.

6. The apparatus of claim 1, wherein said device is adapted to be in electronic communication with separate wearable sensor devices.

7. The apparatus of claim 6, wherein said processor is further programmed to determine said device's distance from at least one of said separate wearable sensor devices.

8. The apparatus of claim 6, wherein said devices communicates said physiological status to at least one of said separate wearable device.

9. The apparatus of claim 1, wherein said wearable sensor device is adapted to be worn on a left upper arm of said individual.

10. The apparatus of claim 2, wherein said processor is further programmed to determine said individual's contextual status from data detected by said at least one sensor.

* * * * *